US012514644B1

(12) United States Patent
Casey et al.

(10) Patent No.: US 12,514,644 B1
(45) Date of Patent: Jan. 6, 2026

(54) POSTERIOR FIXATION SYSTEMS FOR SPINAL TREATMENTS

(71) Applicant: Carlsmed, Inc., Carlsbad, CA (US)

(72) Inventors: Niall Patrick Casey, Carlsbad, CA (US); Sarah Jauregui, San Diego, CA (US); Jeremy Winston, San Diego, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 19/015,447

(22) Filed: Jan. 9, 2025

(51) Int. Cl.
*A61B 34/10* (2016.01)
*A61B 34/00* (2016.01)
*A61F 2/44* (2006.01)

(52) U.S. Cl.
CPC .............. *A61B 34/10* (2016.02); *A61B 34/25* (2016.02); *A61F 2/44* (2013.01); *A61B 2034/105* (2016.02); *A61B 2034/107* (2016.02); *A61B 2034/108* (2016.02)

(58) Field of Classification Search
CPC ...................................................... A61B 34/10
See application file for complete search history.

(56) References Cited

U.S. PATENT DOCUMENTS

| | | | |
|---|---|---|---|
| 4,704,686 | A | 11/1987 | Aldinger |
| 4,936,862 | A | 6/1990 | Walker et al. |
| 5,431,562 | A | 7/1995 | Andreiko et al. |
| 5,514,180 | A | 5/1996 | Heggeness et al. |
| D420,995 | S | 2/2000 | Imamura |
| D436,580 | S | 1/2001 | Navano |
| 6,315,553 | B1 | 11/2001 | Sachdeva |

(Continued)

FOREIGN PATENT DOCUMENTS

| | | | |
|---|---|---|---|
| CN | 104318009 | A | 1/2015 |
| CN | 104353121 | A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Samuel S Hanna
(74) *Attorney, Agent, or Firm* — Perkins Coie LLP

(57) ABSTRACT

Systems and methods for designing and implementing patient-specific surgical procedures and/or medical devices are disclosed. In some embodiments, a method includes selecting a design process protocol for designing a patient-specific implant system based on a target correction for a patient. The patient-specific implant system can select a set of parameters for designing each component of the patient-specific implant system based on patient anatomy and the correction for the patient. An implant designer graphical user interface (GUI) can display the set of parameters for the design process protocol, values for the respective parameters, and a planned anatomy of the patient. The patient-specific implant system can generate a design for a group of patient-specific implants such that the patient-specific implants cooperate to provide anatomical correction to the patient based on the target anatomical correction.

26 Claims, 34 Drawing Sheets

(56) References Cited

U.S. PATENT DOCUMENTS

| | | | |
|---|---|---|---|
| 6,540,512 | B1 | 4/2003 | Sachdeva |
| 6,696,073 | B2 | 2/2004 | Boyce et al. |
| 6,772,026 | B2 | 8/2004 | Bradbury |
| 6,932,842 | B1 | 8/2005 | Litschko et al. |
| 6,978,188 | B1 | 12/2005 | Christensen |
| 6,988,241 | B1 | 1/2006 | Guttman |
| 7,174,282 | B2 | 2/2007 | Hollister et al. |
| 7,187,790 | B2 | 3/2007 | Sabol et al. |
| D548,242 | S | 8/2007 | Viegers |
| D614,191 | S | 4/2010 | Takano |
| 7,731,734 | B2 | 6/2010 | Clement et al. |
| 7,747,305 | B2 | 6/2010 | Dean et al. |
| 7,756,314 | B2 | 7/2010 | Karau et al. |
| 7,763,054 | B2 | 7/2010 | Clement et al. |
| 7,799,077 | B2 | 9/2010 | Lang |
| 7,862,593 | B2 | 1/2011 | Clement et al. |
| D633,514 | S | 3/2011 | Tokunaga |
| 8,114,139 | B2 | 2/2012 | Sournac et al. |
| D656,153 | S | 3/2012 | Imamura |
| 8,147,556 | B2 | 4/2012 | Louis et al. |
| 8,211,109 | B2 | 7/2012 | Groiso |
| 8,246,680 | B2 | 8/2012 | Betz |
| 8,246,685 | B2 | 8/2012 | Sournac et al. |
| 8,265,949 | B2 | 9/2012 | Haddad |
| 8,275,594 | B2 | 9/2012 | Lin |
| 8,308,775 | B2 | 11/2012 | Clement et al. |
| 8,337,507 | B2 | 12/2012 | Lang |
| 8,394,142 | B2 | 3/2013 | Bertagnoli |
| 8,457,930 | B2 | 6/2013 | Shroeder |
| 8,506,632 | B2 | 8/2013 | Ganem et al. |
| 8,532,806 | B1 | 9/2013 | Masson |
| 8,556,983 | B2 | 10/2013 | Bojarski et al. |
| 8,644,568 | B1 | 2/2014 | Hoffman |
| 8,735,773 | B2 | 5/2014 | Lang |
| 8,758,357 | B2 | 6/2014 | Frey |
| 8,775,133 | B2 | 7/2014 | Schroeder |
| 8,781,557 | B2 | 7/2014 | Dean |
| 8,801,786 | B2 | 8/2014 | Bernard et al. |
| 8,828,083 | B2 | 9/2014 | Sournac et al. |
| 8,843,229 | B2 | 9/2014 | Vanasse |
| 8,855,389 | B1 | 10/2014 | Hoffman |
| 8,870,889 | B2 | 10/2014 | Frey |
| 8,926,673 | B2 | 1/2015 | Clement et al. |
| 8,956,416 | B2 | 2/2015 | McCarthy |
| 8,998,962 | B2 | 4/2015 | Birch |
| 9,020,788 | B2 | 4/2015 | Lang |
| 9,034,037 | B2 | 5/2015 | Fiere et al. |
| D735,231 | S | 7/2015 | Omiya |
| D737,309 | S | 8/2015 | Kito |
| 9,144,440 | B2 | 9/2015 | Aminian |
| 9,192,412 | B2 | 11/2015 | Meyrat et al. |
| 9,198,678 | B2 | 12/2015 | Frey et al. |
| 9,208,558 | B2 | 12/2015 | Dean |
| 9,314,275 | B2 | 4/2016 | Clement et al. |
| 9,320,612 | B2 | 4/2016 | Sournac et al. |
| D757,025 | S | 5/2016 | Kim |
| 9,358,051 | B2 | 6/2016 | Sournac et al. |
| D761,842 | S | 7/2016 | Johnson |
| 9,381,093 | B1 | 7/2016 | Morris et al. |
| 9,387,015 | B2 | 7/2016 | Taylor |
| 9,408,642 | B2 | 8/2016 | Wong et al. |
| 9,411,939 | B2 | 8/2016 | Furrer |
| 9,445,907 | B2 | 9/2016 | Meridew |
| 9,452,050 | B2 | 9/2016 | Miles et al. |
| D774,076 | S | 12/2016 | Fuller |
| 9,510,864 | B2 | 12/2016 | Devito |
| 9,542,525 | B2 | 1/2017 | Arisoy et al. |
| 9,561,113 | B2 | 2/2017 | Howard |
| 9,642,633 | B2 | 5/2017 | Frey et al. |
| 9,642,718 | B2 | 5/2017 | Sournac et al. |
| 9,693,831 | B2 | 7/2017 | Mosnier et al. |
| 9,707,058 | B2 | 7/2017 | Bassett |
| 9,715,563 | B1 | 7/2017 | Schroeder |
| D797,760 | S | 9/2017 | Tsujimura |
| D797,766 | S | 9/2017 | Ibsies |

| | | | |
|---|---|---|---|
| D798,312 | S | 9/2017 | Tsujimura |
| 9,757,245 | B2 | 9/2017 | O'Neil et al. |
| D798,894 | S | 10/2017 | Ibsies |
| 9,775,680 | B2 | 10/2017 | Bojarski et al. |
| 9,782,228 | B2 | 10/2017 | Mosnier et al. |
| D812,628 | S | 3/2018 | Okado |
| 9,987,048 | B2 | 6/2018 | Mosnier et al. |
| 9,993,341 | B2 | 6/2018 | Vanasse |
| 10,034,676 | B2 | 7/2018 | Donner |
| D825,605 | S | 8/2018 | Jann |
| D826,977 | S | 8/2018 | Nakajima |
| 10,089,413 | B2 | 10/2018 | Wirx-Speetjens et al. |
| 10,143,495 | B2 | 12/2018 | Sournac et al. |
| D841,675 | S | 2/2019 | Hoffman |
| 10,213,311 | B2 | 2/2019 | Mafhouz |
| D845,973 | S | 4/2019 | Jaycobs |
| D845,974 | S | 4/2019 | Cooperman |
| D847,165 | S | 4/2019 | Kolbenheyer |
| 10,245,079 | B2 | 4/2019 | Sournac et al. |
| D848,468 | S | 5/2019 | Ng |
| D849,029 | S | 5/2019 | Cooperman |
| D849,773 | S | 5/2019 | Jiang |
| 10,292,770 | B2 | 5/2019 | Ryan |
| 10,299,863 | B2 | 5/2019 | Grbic et al. |
| 10,318,655 | B2 | 6/2019 | Mosnier et al. |
| D854,560 | S | 7/2019 | Field |
| D854,561 | S | 7/2019 | Field |
| 10,390,958 | B2 | 8/2019 | Maclennan |
| D860,237 | S | 9/2019 | Li |
| D860,238 | S | 9/2019 | Bhardwaj |
| 10,426,521 | B2 | 10/2019 | Mosnier et al. |
| 10,456,211 | B2 | 10/2019 | McAfee |
| D866,577 | S | 11/2019 | Eisert |
| D867,379 | S | 11/2019 | Ang |
| D867,389 | S | 11/2019 | Jamison |
| 10,463,433 | B2 | 11/2019 | Turner et al. |
| 10,470,802 | B2 | 11/2019 | Sournac et al. |
| D870,762 | S | 12/2019 | Mendoza |
| 10,512,546 | B2 | 12/2019 | Kamer et al. |
| 10,517,681 | B2 | 12/2019 | Roh et al. |
| D872,117 | S | 1/2020 | Kobayashi |
| D872,756 | S | 1/2020 | Howell |
| D874,490 | S | 2/2020 | Dodsworth |
| D875,761 | S | 2/2020 | Heffernan |
| D876,454 | S | 2/2020 | Knowles |
| D876,462 | S | 2/2020 | Li |
| D877,167 | S | 3/2020 | Knowles |
| D879,112 | S | 3/2020 | Hejazi |
| 10,588,589 | B2 | 3/2020 | Bregman-Amitai et al. |
| 10,603,055 | B2 | 3/2020 | Donner et al. |
| D880,513 | S | 4/2020 | Wang |
| D881,908 | S | 4/2020 | Sunil |
| D881,910 | S | 4/2020 | Lin |
| 10,621,289 | B2 | 4/2020 | Schroeder |
| 10,624,677 | B2 | 4/2020 | Mosnier et al. |
| 10,631,988 | B2 | 4/2020 | Arnold et al. |
| D884,008 | S | 5/2020 | Thornberg |
| 10,646,236 | B2 | 5/2020 | Donner et al. |
| 10,646,258 | B2 | 5/2020 | Donner et al. |
| 10,736,698 | B2 | 8/2020 | Bohl |
| 10,751,188 | B2 | 8/2020 | Guo et al. |
| D896,825 | S | 9/2020 | Abel |
| D896,828 | S | 9/2020 | Linares |
| D898,054 | S | 10/2020 | Everhart |
| D899,438 | S | 10/2020 | Crafts |
| 10,806,597 | B2 | 10/2020 | Sournac et al. |
| 10,902,944 | B1 | 1/2021 | Casey et al. |
| 10,918,422 | B2 | 2/2021 | Mosnier et al. |
| D916,868 | S | 4/2021 | Evangeliou |
| D916,879 | S | 4/2021 | Mitsumori |
| D918,253 | S | 5/2021 | Choe |
| 11,000,334 | B1 | 5/2021 | Young |
| D921,675 | S | 6/2021 | Kmak |
| D921,677 | S | 6/2021 | Kmak |
| D921,687 | S | 6/2021 | Kmak |
| D924,909 | S | 7/2021 | Nasu |
| D925,567 | S | 7/2021 | Hayamizu |
| D927,528 | S | 8/2021 | Heisler |
| 11,083,586 | B2 | 8/2021 | Cordonnier |

(56) References Cited

U.S. PATENT DOCUMENTS

| | | | |
|---|---|---|---|
| 11,112,770 | B2 | 9/2021 | Roh et al. |
| D933,692 | S | 10/2021 | Smith |
| 11,166,764 | B2 | 11/2021 | Roh et al. |
| 11,185,369 | B2 | 11/2021 | Ryan |
| D937,870 | S | 12/2021 | Pinto |
| D937,876 | S | 12/2021 | Harvey |
| D938,461 | S | 12/2021 | Hoffman |
| D938,986 | S | 12/2021 | Grossberg |
| D940,178 | S | 1/2022 | Ang |
| D946,022 | S | 3/2022 | Nuttbrown |
| D946,023 | S | 3/2022 | Nuttbrown |
| D946,024 | S | 3/2022 | Vogler-Ivashchanka |
| D946,616 | S | 3/2022 | Tsai |
| D958,151 | S | 7/2022 | Casey et al. |
| 11,376,076 | B2 | 7/2022 | Casey et al. |
| 11,432,943 | B2 | 9/2022 | Casey et al. |
| 11,439,514 | B2 | 9/2022 | Casey et al. |
| 11,443,838 | B1 | 9/2022 | Cordonnier |
| 11,497,559 | B1 | 11/2022 | Roh et al. |
| 11,612,436 | B2 | 3/2023 | McAfee et al. |
| 11,678,938 | B2 | 6/2023 | Casey et al. |
| 11,779,351 | B2 | 10/2023 | Buttin et al. |
| 11,877,801 | B2 | 1/2024 | Mosnier et al. |
| 11,984,205 | B2 | 5/2024 | Cordonnier |
| 12,089,857 | B2 | 9/2024 | Buttin et al. |
| 2002/0016595 | A1 | 2/2002 | Michelson |
| 2004/0104512 | A1 | 6/2004 | Eidenschink |
| 2004/0210314 | A1 | 10/2004 | Michelson |
| 2005/0234555 | A1 | 10/2005 | Sutton et al. |
| 2005/0273170 | A1 | 12/2005 | Navarro et al. |
| 2007/0272747 | A1 | 11/2007 | Woods et al. |
| 2007/0276369 | A1 | 11/2007 | Allard et al. |
| 2007/0276501 | A1 | 11/2007 | Betz |
| 2008/0089566 | A1 | 4/2008 | Node-Langlois |
| 2008/0227047 | A1 | 9/2008 | Lowe |
| 2009/0062739 | A1 | 3/2009 | Anderson |
| 2010/0191088 | A1 | 7/2010 | Anderson et al. |
| 2010/0298942 | A1 | 11/2010 | Hansell |
| 2010/0324692 | A1 | 12/2010 | Uthgenannt |
| 2011/0196451 | A1 | 8/2011 | Hill |
| 2012/0150243 | A9 | 6/2012 | Crawford et al. |
| 2012/0322018 | A1 | 12/2012 | Lowe |
| 2013/0323669 | A1 | 12/2013 | Lowe |
| 2014/0072608 | A1 | 3/2014 | Karagkiozaki |
| 2014/0074438 | A1 | 3/2014 | Furrer |
| 2014/0081659 | A1 | 3/2014 | Nawana et al. |
| 2014/0086780 | A1 | 3/2014 | Miller |
| 2014/0100886 | A1 | 4/2014 | Woods |
| 2014/0164022 | A1 | 6/2014 | Reed |
| 2014/0263674 | A1 | 9/2014 | Cerveny |
| 2014/0277487 | A1 | 9/2014 | Davenport et al. |
| 2014/0350614 | A1 | 11/2014 | Frey |
| 2015/0079533 | A1 | 3/2015 | Lowe |
| 2015/0089590 | A1 | 3/2015 | Krishnan et al. |
| 2015/0105891 | A1 | 4/2015 | Golway et al. |
| 2015/0199488 | A1 | 7/2015 | Falchuk |
| 2015/0213225 | A1 | 7/2015 | Amarasingham |
| 2015/0324490 | A1 | 11/2015 | Page |
| 2015/0328004 | A1 | 11/2015 | Mafhouz |
| 2015/0332018 | A1 | 11/2015 | Rosen |
| 2016/0001039 | A1 | 1/2016 | Armour et al. |
| 2016/0015465 | A1 | 1/2016 | Steines et al. |
| 2016/0030067 | A1 | 2/2016 | Frey et al. |
| 2016/0074048 | A1 | 3/2016 | Pavlovskaia |
| 2016/0081810 | A1 | 3/2016 | Reiley et al. |
| 2016/0117817 | A1 | 4/2016 | Seel |
| 2016/0143744 | A1 | 5/2016 | Bojarski et al. |
| 2016/0184054 | A1 | 6/2016 | Lowe |
| 2016/0210374 | A1 | 7/2016 | Mosnier et al. |
| 2016/0217268 | A1 | 7/2016 | Otto |
| 2016/0242857 | A1 | 8/2016 | Scholl |
| 2016/0300026 | A1 | 10/2016 | Bogoni et al. |
| 2016/0354039 | A1 | 12/2016 | Soto et al. |
| 2016/0354161 | A1 | 12/2016 | Deitz |
| 2016/0354213 | A1 | 12/2016 | Cowan |
| 2016/0378919 | A1 | 12/2016 | McNutt et al. |
| 2017/0000566 | A1 | 1/2017 | Gordon |
| 2017/0014169 | A1 | 1/2017 | Dean |
| 2017/0020679 | A1 | 1/2017 | Maclennan |
| 2017/0035514 | A1 | 2/2017 | Fox et al. |
| 2017/0061375 | A1 | 3/2017 | Laster |
| 2017/0068792 | A1 | 3/2017 | Reiner |
| 2017/0112548 | A1 | 4/2017 | Alamin et al. |
| 2017/0135706 | A1 | 5/2017 | Frey et al. |
| 2017/0143494 | A1 | 5/2017 | Mahfouz |
| 2017/0143831 | A1 | 5/2017 | Varanasi et al. |
| 2017/0196499 | A1 | 7/2017 | Hunter |
| 2017/0216047 | A1 | 8/2017 | Hawkes et al. |
| 2017/0220740 | A1 | 8/2017 | D'Urso |
| 2017/0252107 | A1 | 9/2017 | Turner et al. |
| 2017/0262595 | A1 | 9/2017 | Vorhis |
| 2017/0340447 | A1 | 11/2017 | Mahfouz |
| 2017/0354510 | A1 | 12/2017 | O'Neil et al. |
| 2017/0367645 | A1 | 12/2017 | Klinder |
| 2018/0008349 | A1 | 1/2018 | Gillman |
| 2018/0113992 | A1 | 4/2018 | Eltorai et al. |
| 2018/0116727 | A1 | 5/2018 | Caldwell et al. |
| 2018/0168499 | A1 | 6/2018 | Bergold |
| 2018/0168731 | A1 | 6/2018 | Reid |
| 2018/0185075 | A1 | 7/2018 | She |
| 2018/0233222 | A1 | 8/2018 | Daley |
| 2018/0233225 | A1 | 8/2018 | Experton |
| 2018/0250075 | A1 | 9/2018 | Cho |
| 2018/0303552 | A1 | 10/2018 | Ryan |
| 2018/0303616 | A1 | 10/2018 | Bhattacharyya et al. |
| 2018/0308569 | A1 | 10/2018 | Luellen |
| 2018/0318100 | A1 | 11/2018 | Altarac |
| 2018/0338841 | A1 | 11/2018 | Miller et al. |
| 2019/0065685 | A1 | 2/2019 | Pickover |
| 2019/0069956 | A1 | 3/2019 | Ryan et al. |
| 2019/0099221 | A1 | 4/2019 | Schmidt et al. |
| 2019/0201106 | A1 | 7/2019 | Siemionow |
| 2019/0262084 | A1 | 8/2019 | Roh et al. |
| 2019/0266597 | A1 | 8/2019 | Mohtar |
| 2019/0328929 | A1 | 10/2019 | Kugler et al. |
| 2019/0333622 | A1 | 10/2019 | Levin |
| 2019/0354693 | A1 | 11/2019 | Yoon |
| 2019/0380792 | A1 | 12/2019 | Poltaretskyi et al. |
| 2019/0388131 | A1 | 12/2019 | Mehl et al. |
| 2020/0021570 | A1 | 1/2020 | Lin |
| 2020/0078180 | A1 | 3/2020 | Casey et al. |
| 2020/0085509 | A1 | 3/2020 | Roh et al. |
| 2020/0138523 | A1 | 5/2020 | Greenwald |
| 2020/0170802 | A1 | 6/2020 | Casey et al. |
| 2020/0246162 | A1 | 8/2020 | Schultz et al. |
| 2020/0258605 | A1 | 8/2020 | Blechman |
| 2020/0261156 | A1 | 8/2020 | Schmidt |
| 2020/0289288 | A1 | 9/2020 | Müller et al. |
| 2020/0315708 | A1 | 10/2020 | Mosnier et al. |
| 2020/0323654 | A1 | 10/2020 | Marrapode |
| 2021/0059822 | A1 | 3/2021 | Casey et al. |
| 2021/0064605 | A1 | 3/2021 | Balint |
| 2021/0085482 | A1 | 3/2021 | Flickinger et al. |
| 2021/0145519 | A1 | 5/2021 | Mosnier et al. |
| 2021/0169576 | A1 | 6/2021 | Ryan et al. |
| 2021/0192759 | A1 | 6/2021 | Lang |
| 2021/0210189 | A1 | 7/2021 | Casey et al. |
| 2021/0287770 | A1 | 9/2021 | Anderson |
| 2021/0382457 | A1 | 12/2021 | Roh et al. |
| 2022/0000625 | A1 | 1/2022 | Cordonnier |
| 2022/0006642 | A1 | 1/2022 | Maj et al. |
| 2022/0013211 | A1 | 1/2022 | Steinberg et al. |
| 2022/0039965 | A1 | 2/2022 | Casey et al. |
| 2022/0047402 | A1 | 2/2022 | Casey et al. |
| 2022/0110686 | A1 | 4/2022 | Roh et al. |
| 2022/0130509 | A1 | 4/2022 | Buttin et al. |
| 2022/0160405 | A1 | 5/2022 | Casey et al. |
| 2022/0160518 | A1 | 5/2022 | Casey et al. |
| 2022/0387191 | A1 | 12/2022 | Cordonnier |
| 2022/0401150 | A1 | 12/2022 | Cordonnier |
| 2022/0409140 | A1 | 12/2022 | Cordonnier |
| 2022/0409279 | A1 | 12/2022 | Benson et al. |
| 2023/0000560 | A1 | 1/2023 | Roh et al. |
| 2023/0014384 | A1 | 1/2023 | Cordonnier |

(56) References Cited

U.S. PATENT DOCUMENTS

| | | | |
|---|---|---|---|
| 2023/0023440 | A1 | 1/2023 | Casey et al. |
| 2023/0034731 | A1 | 2/2023 | Cordonnier |
| 2023/0052263 | A1 | 2/2023 | Casey et al. |
| 2023/0067537 | A1 | 3/2023 | Casey et al. |
| 2023/0086886 | A1 | 3/2023 | Casey et al. |
| 2023/0088477 | A1 | 3/2023 | Roussouly et al. |
| 2023/0092357 | A1 | 3/2023 | Benson et al. |
| 2023/0136813 | A1 | 5/2023 | Cordonnier |
| 2023/0218308 | A1 | 7/2023 | Roussouly et al. |
| 2023/0263541 | A1 | 8/2023 | Roussouly |
| 2023/0277246 | A1 * | 9/2023 | Casey ................. G06F 21/6245 |
| 2024/0197400 | A1 | 6/2024 | Benson et al. |
| 2024/0277412 | A1 | 8/2024 | Benson et al. |
| 2024/0346191 | A1 | 10/2024 | Mosnier et al. |

FOREIGN PATENT DOCUMENTS

| | | | |
|---|---|---|---|
| CN | 204468348 | U | 7/2015 |
| CN | 105796214 | A | 7/2016 |
| CN | 106202861 | | 12/2016 |
| CN | 107220933 | | 9/2017 |
| CN | 108670506 | A | 10/2018 |
| CN | 110575289 | A | 12/2019 |
| CN | 111281613 | A | 6/2020 |
| CN | 112155792 | A | 1/2021 |
| CN | 113643790 | | 11/2021 |
| EP | 2716262 | B1 | 5/2015 |
| EP | 3120796 | A1 | 1/2017 |
| EP | 3982856 | A1 | 4/2022 |
| EP | 3565491 | A1 | 5/2023 |
| ES | 2299016 | T3 | 5/2008 |
| ES | 2337697 | T3 | 4/2010 |
| ES | 2393431 | T3 | 12/2012 |
| ES | 2414313 | T3 | 7/2013 |
| ES | 2477965 | T3 | 7/2014 |
| ES | 2547652 | T3 | 10/2015 |
| ES | 2547891 | T3 | 10/2015 |
| ES | 2625265 | T3 | 7/2017 |
| FR | 2978347 | B1 | 8/2013 |
| FR | 3022449 | B1 | 5/2019 |
| FR | 3093422 | B1 | 9/2020 |
| FR | 3093286 | B1 | 3/2021 |
| FR | 3082115 | B1 | 7/2022 |
| FR | 3078883 | B1 | 6/2023 |
| WO | 9507509 | A1 | 3/1995 |
| WO | 2004110309 | A2 | 12/2004 |
| WO | 2010151564 | A1 | 12/2010 |
| WO | 2012154534 | A1 | 11/2012 |
| WO | 2014180972 | A2 | 11/2014 |
| WO | 2016172694 | A1 | 10/2016 |
| WO | 2017116346 | A1 | 7/2017 |
| WO | 2019018013 | A1 | 1/2019 |
| WO | 2019112917 | A1 | 6/2019 |
| WO | 2019148154 | A1 | 8/2019 |
| WO | 2019165152 | A1 | 8/2019 |
| WO | 2019241167 | A1 | 12/2019 |
| WO | 2020055874 | A1 | 3/2020 |
| WO | 2022045956 | A1 | 3/2022 |
| WO | 2022109097 | A1 | 5/2022 |
| WO | 2022261171 | A1 | 12/2022 |
| WO | 2022266313 | A1 | 12/2022 |
| WO | 2023034405 | A1 | 3/2023 |

OTHER PUBLICATIONS

International Search Report and Written Opinion for International Application No. PCT/US22/32624, mailed Oct. 28, 2022, 16 pages.
International Search Report and Written Opinion for International Application No. PCT/US22/33775, mailed Sep. 8, 2022, 17 pages.
International Search Report and Written Opinion for International Patent Application No. PCT/US21/59837, mailed Feb. 7, 2022, 19 pages.
International Search Report and Written Opinion for International Application No. PCT/US24/10202, mailed Jul. 16, 2024, 14 pages.
Materialise Mimics, “Efficiently turn scans into accurate virtual 3D models,” Retrieved on Nov. 1, 2019 at www.materialize.com/en/medical/software/mimics, 1 page.
Pimenta, Dr. Luiz, “Current Surgical Strategies to Restore Proper Sagittal Alignment,” Journal of Spine 2015, vol. 4, Issue 4, 2 pages.

* cited by examiner

400

| PATIENT | |
|---|---|
| **PT. ID** | JDoe |
| **Metric** | **Value** |
| Age | 58 |
| Gender | M |
| BMI | 32 |
| LL | 40 |
| PI | 55 |
| Levels | 4 |

*FIG. 4A*

410a 410

412 Study Group X

| PT. ID | X123 | Y456 | Z789 | A246 |
|---|---|---|---|---|
| Metric | Value | Value | Value | Value |
| Age | 56 | 66 | 63 | 73 |
| Gender | F | F | M | M |
| BMI | 38 | 38 | 30 | 30 |
| LL | 36 | 41 | 39 | 40 |
| PI | 51 | 52 | 50 | 48 |
| Levels | 3 | 4 | 4 | 5 |
| Outcome | | | | |
| Fused | Y | Y | Y | N |
| HRQL | A | B | A | D |
| Complications | 0 | 0 | 1 | 0 |
| Surg. Intervention | | | | |
| Imp. design | Stock | Stock | Stock | Stock |
| Imp placemt | A | A | B | B |
| Surg. Appr. | Lat | Ant | Lat | Post |

410b 410c

414 Practice Y

| PT. ID | B135 | C468 | D357 | E468 |
|---|---|---|---|---|
| Metric | Value | Value | Value | Value |
| Age | 73 | 60 | 58 | 78 |
| Gender | F | M | M | M |
| BMI | 37 | 32 | 29 | 30 |
| LL | 40 | 40 | 39 | 40 |
| PI | 55 | 55 | 52 | 48 |
| Levels | 4 | 4 | 4 | 3 |
| Outcome | | | | |
| Fused | Y | Y | N | N |
| HRQL | A | A | C | F |
| Complications | 0 | 0 | 1 | 0 |
| Surg. Intervention | | | | |
| Imp. design | PS | PS | Stock | Stock |
| Imp placemt | A | A | B | B |
| Surg. Appr. | Ant | Ant,Lat | Post | Lat |

410d

416 University Z

| PT. ID | F135 | G468 | H357 | J468 |
|---|---|---|---|---|
| Metric | Value | Value | Value | Value |
| Age | 73 | 60 | 63 | 71 |
| Gender | F | M | M | M |
| BMI | 33 | 42 | 31 | 30 |
| LL | 40 | 40 | 39 | 40 |
| PI | 55 | 55 | 52 | 50 |
| Levels | 4 | 4 | 4 | 3 |
| Outcome | | | | |
| Fused | Y | Y | Y | N |
| HRQL | A | A | A | F |
| Complications | 0 | 0 | 1 | 2 |
| Surg. Intervention | | | | |
| Imp. design | PS | PS | PS | Stock |
| Imp placemt | A | A | B | B |
| Surg. Appr. | Post | Ant,Lat | Ant,Lat | Lat |

FIG. 4B 420 430

| | Pre-op Similarity | | Outcome quotient |
|---|---|---|---|
| | Pt. ID | Value | |
| 410a | X123 | 9 | 1 |
| | Y456 | 18 | 2 |
| | Z789 | 11 | 2 |
| | A246 | 25 | 9 |
| | B135 | 20 | 1 |
| 410b | C468 | 2 | 1 |
| 410c | D357 | 5 | 9 |
| | E468 | 30 | 10 |
| | F135 | 16 | 1 |
| | G468 | 12 | 1 |
| 410d | H357 | 8 | 2 |
| | J468 | 21 | 12 |

*FIG. 4C*

| PRE-OP | | | | |
|---|---|---|---|---|
| PI | 66.8° | | | |
| LL | 42.6° | | | |
| PI-LL | 24.2° | | | |
| CORONAL | 7° | | | |

| LOCAL: LEVEL | LORDOSIS | % | H-ANT (mm) | H-POST (mm) |
|---|---|---|---|---|
| L2/3 | 1.6° | 4% | 3.0 | 0.7 |
| L3/4 | 14.2° | 36% | 4.0 | 1.5 |
| L4/5 | 15.2° | 39% | 5.0 | 2.8 |
| L5/S1 | 1.3° | 3% | 2.0 | 0.3 |

| PLAN | | | | |
|---|---|---|---|---|
| PI | 66.8° | | | |
| LL | 59.3° | | | |
| PI-LL | 7.6° | | | |
| CORONAL | 1.0° | | | |

| LOCAL: LEVEL | LORDOSIS | % | H-ANT (mm) | H-POST (mm) |
|---|---|---|---|---|
| L2/3 | 9.3° | 21% | 12.0 | 7.7 |
| L3/4 | 11.6° | 26% | 15.0 | 7.9 |
| L4/5 | 12.4° | 27% | 14.0 | 3.7 |
| L5/S1 | 11.3° | 25% | 17.0 | 3.6 |

POSTERIOR FIXATION SYSTEMS FOR SPINAL TREATMENTS

TECHNICAL FIELD

The present disclosure is generally related to surgical technology, and more particularly to implantation fixation systems, implants, surgical kits, and methods for providing assistance for surgical procedures.

BACKGROUND

Orthopedic implants are used to correct a variety of different maladies. Spine surgery may encompass one or more of the cervical, thoracic, lumbar spine, sacrum, pelvis, or ilium, and may treat a deformity or degeneration of the spine, or related back pain, leg pain, or other body pain. Irregular spinal curvature may include scoliosis, lordosis, or kyphosis (hyper- or hypo-). Irregular spinal displacement may include spondylolisthesis. Other spinal disorders include osteoarthritis, lumbar degenerative disc disease or cervical degenerative disc disease, and lumbar spinal stenosis or cervical spinal stenosis.

Spinal fusion surgery may be performed to set and hold purposeful changes imparted on the spine. Spinal surgeries often include hardware or implants to help fix the relationship between anatomical structures such as vertebral bodies and nerves. In many instances, fixation devices or implants are affixed to bony anatomy to provide support during healing. These implants are often made of polymers or metals (including titanium, titanium alloy, stainless steel, cobalt chrome, or other alloys). Each implant can mate with the anatomy or other implants in order to provide a construct to allow relief of symptoms and encourage biologic healing.

Spinal surgeons are often relied upon to treat patients with spinal deformities, such as scoliosis. These surgical treatments may require realignment of spinal anatomy and preservation of the realignment in order to relieve symptoms. Surgeons manipulate the spine using instruments and implants that mate with bony anatomy. Adjustment of the instruments and implants connected to the bony anatomy can produce the desired alignment of the spinal anatomy. Spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion). One goal of interbody fusion is to grow bone between vertebrae in order to seize (e.g., lock) the spatial relationships in a position that provides enough room for neural elements, including exiting nerve roots. An interbody implant (interbody device, interbody implant, interbody cage, fusion cage, or spine cage) is a prosthesis used between vertebral bodies in spinal fusion procedures to maintain relative position of the vertebrae and establish appropriate foraminal height and decompression of exiting nerves. Each patient may have individual or unique disease characteristics. Unfortunately, conventional device solutions often involve implants (e.g., rods, screws, interbody implants) having standard sizes or shapes.

BRIEF DESCRIPTION OF THE DRAWINGS

FIGS. 4A-4C illustrate exemplary data sets that may be used and/or generated in connection with the methods described herein, according to an embodiment. FIG. 4A illustrates a patient data set. FIG. 4B illustrates a plurality of reference patient data sets.

FIG. 4C illustrates similarity scores and outcome scores for the reference patient data sets of FIG. 4B.

FIGS. 9A-1-9B-2 illustrate an exemplary virtual model of a patient's spine in a pre-operative anatomical configuration and a corrected anatomical configuration. More specifically, FIGS. 9A-1 and 9A-2 illustrate the pre-operative anatomical configuration of the patient, and FIGS. 9B-1 and 9B-2 illustrate the corrected anatomical configuration.

DETAILED DESCRIPTION

Figure 1:
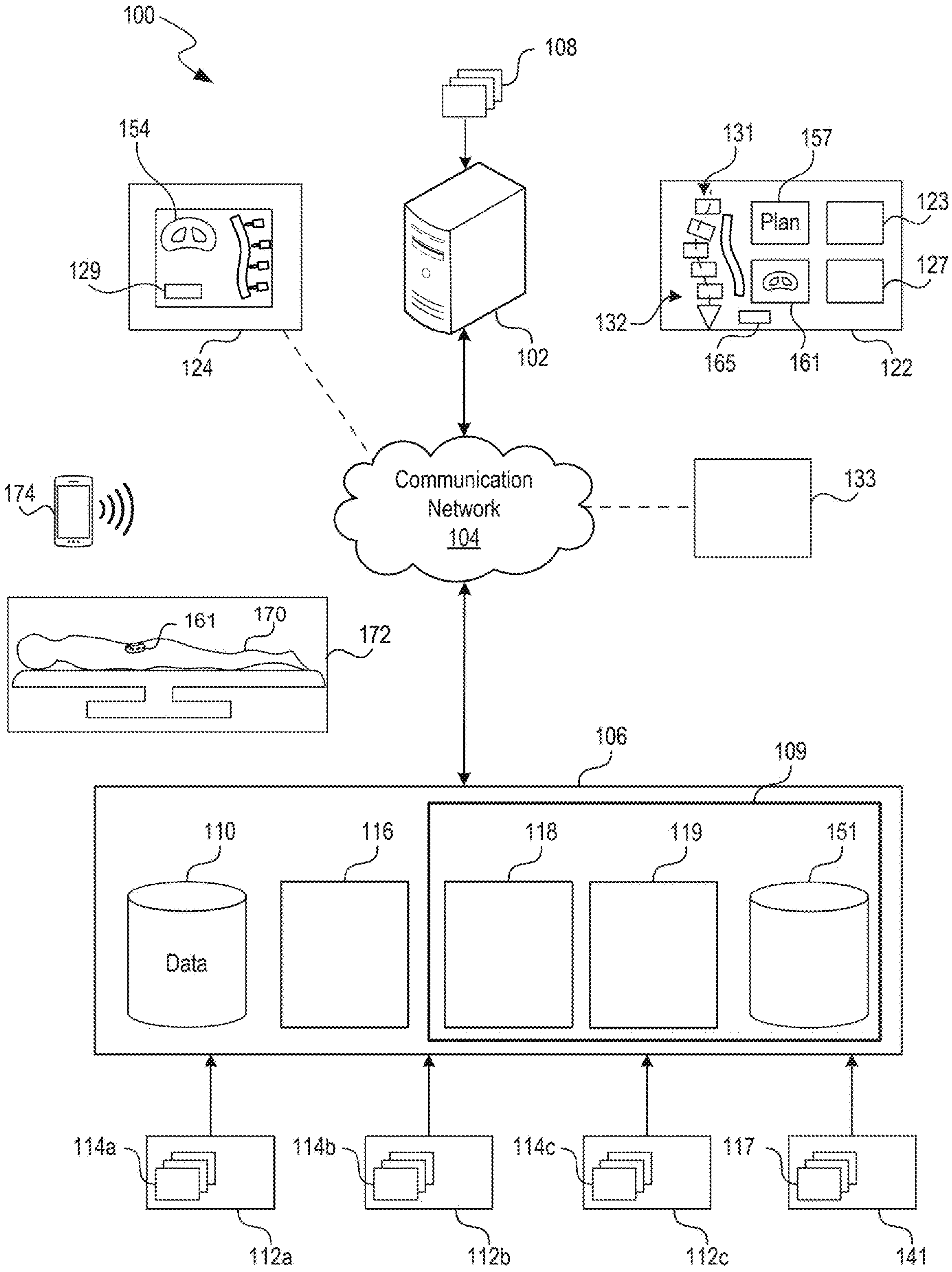
FIG. 1 is a network connection diagram illustrating a system for providing patient-specific medical care, according to an embodiment.

The present technology is directed to systems and methods for assisting surgical procedures involving patient-specific implant systems. The present technology can be used to select candidate treatments, design patient-specific implant systems, generate plans, or the like. A user can view candidate treatments, planned outcomes, implant designs, and surgical techniques for delivering implants. The present technology can simulate treatments to evaluate interaction and/or fits between implants and planned outcomes. The present technology can be used to individually or collectively design patient-specific implants. Individual implants, sets of implants, surgical kits, and/or multi-component implant systems can be individually or collectively scored. Plans and implant designs can be synchronized such that each is updated when the other is modified. A user and/or machine learning system can iteratively modify plans and/or implant designs to develop a desired treatment.

In some embodiments, the present technology can generate a planned corrected anatomy for a patient. A system can select an implant system for achieving the planned corrected anatomy and can determine a number and type of implants (or components) for the implant system. In some embodiments, the system can individually design multiple patient-specific implants (or components) of the implant system by, for example, determining parameters for the individual implants (or components). The design process can include, without limitation, identifying positions of implants, determining interfaces between implants and anatomy, determining fits between components, or the like. For example, the system can identify trajectories and positions for bone screws and can then design bone screws based on the trajectories and positions. One or more spinal rods can be designed to achieve a corrected curvature of the patient's spine, enhance biomechanics, etc. The system can design connectors (e.g., rod holders, rod couple, etc.) configured to couple the rods to the bone screws based on the position and/or trajectory of the bone screws and the design of the spinal rods. This allows the system to consider a wide range of design parameters when selecting treatments, designing implant systems, etc.

The present technology can include a surgery manager system having a user interface (e.g., graphical user interface) for modifying items (e.g., plans, implant designs), models (e.g., anatomical models, models of implants, etc.); approving candidate treatments; inputting data (e.g., physician notes, observations, etc.), etc. In some cases, an interactive surgical plan includes a viewable planned intra-operative pathology for the patient, predicted outcomes, simulations (e.g., pre-operative simulations, intra-operative simulation, post-operative simulations, disease progression simulations, etc.), comparisons (e.g., comparisons of plans, simulations, etc.), implant modifier, surgical kit selector, metrics, or combinations thereof.

The surgery manager system can overlay an image of one or more implants or an implant system on patient images. The patient images can be pre-operative images, planned outcome images (e.g., images of predict long-term outcomes and/or outcomes at a user-selected time (e.g., week(s), month(s), year(s) after surgery)), or other images. In some embodiments, the surgery manager system can dynamically update predicted long-term outcomes based on modifications to implants, implant positions, or the like. For example, a user can modify dimensions of one or more implants. The surgery manager system can then generate new predicted long-term outcomes based on the modified implant(s). This allows users to evaluate relationships between dimensions of implants and outcomes. In some embodiments, the surgery manager system can identify relationships between implant dimensions and outcomes. The surgery manager system can generate recommendations and candidate procedures based on one or more of those relationships. In some embodiments, the surgery manager system can overlay images of virtual models of designed implants onto image(s) of anatomical models of patients. A user can modify parameters of the implant and view the modified implant in real- or near real-time. This allows a user to dynamically update implant designs while evaluating anatomical configurations, including pre-operative anatomical configurations, intra-operative anatomical configurations, and post-operative anatomical configurations (e.g., including long-term post-operative outcomes).

The surgery manager system can overlay intra-operative image(s) over pre-operatively planned image(s) to confirm that a patient-specific implant is located and positioned according to the surgical plan. The surgery manager system can overlay predicted outcome image(s) over anatomical images (e.g., pre-operative image(s), intra-operative image(s), etc.) to show predicted outcomes. If parameters of the implant system are modified, the surgery manager system can modify the predicted outcome image(s) (or virtual model of predicted outcomes) based on the modified parameters. The parameters can include, for example, dimensions, target implant positions, material of implants, etc. The surgery manager system can generate a model of an implant system positioned along an anatomical model. The surgery manager system can determine relationships between components of the implant system and the anatomical model. If one model is modified, other model(s) can also be modified.

In some embodiments, a method comprises generating a virtual model of at least a portion of a spine of a patient. A multi-component design platform can determine a target anatomical configuration for the spine. The multi-component design platform can design a posterior fixation assembly including one or more patient-specific spinal rods and a plurality of anchor assemblies. For example, the posterior fixation assembly can be designed to fit the virtual model of the spine in a target anatomical configuration. The patient-specific spinal rods can be configured to achieve the target anatomical configuration while the anchor assemblies can be configured to anchor the rods to vertebrae. The technology can generate a treatment plan including posterior fixation assembly information and at least one of planned spinopelvic metrics, planned spinal metrics, or other anatomical values for evaluating treatment. The posterior fixation assembly information can include, without limitation, number of implant components, number of patient-specific implant components, number of standard implant components, fit between the implant components, parameters of the implant components (for example, dimensions), or the like. The treatment plan can be viewed using a user device.

The surgery manager system can analyze planned placement of the posterior fixation assembly using, for example, images (e.g., pre-operative images, real-time intra-operative images, radiographic images, fluoroscopy, etc.), direct visualization, and/or other data. In some procedures, the implant may be modified by the surgery manager system and/or surgical team. For example, a spinal rod can be bent by a physician during surgery. The surgery manager system can generate intra-operative images showing, for example, the target position for the modified rod relative to anatomical elements, a predicted outcome using the modified rod, recommended additional modifications to the rod, recommended bone screws/anchors for use with the modified rod, metrics, etc. The rod can be modified any number of times based on updated simulations. In some embodiments, the surgery manager system can provide instructions or guidance for modifying rods to achieve a target modified implant.

The surgery manager system can generate a surgical plan based on the inputted targeted outcomes, implant type information, designs for implants, etc. A user can modify anatomy, modify implants, reposition implant(s), generate new surgical plans, confirm surgical steps, and/or approve predicted outcomes any number of times until achieving a suitable score. The surgery manager system can provide real-time feedback (e.g., real-time implant modifications, new or modified surgical steps, post-operative predicted outcomes) based on real-time data. Simulation triggers can be identified to generate new simulations. Example simulation triggers include, for example, modifying parameters of implants, modifying targeted anatomy, modifying planned positions of implants, and/or identifying deviations exceeding a threshold (e.g., implant modification deviations exceeding a predetermined threshold value). For example, each time modification of dimension(s) of implant(s) occurs, the system can generate new simulations to output feedback. The predictions can be used to confirm that the procedure will provide the desired outcome, implant components fit together, etc. In some procedures, a user can input one or more proposed modifications. The system can simulate outcomes based on the one or more proposed modifications and can recommend further modifications. The simulated outcomes can include, for example, anatomical models, patient metrics, recovery rates, fusion rates, spinal alignment, anatomical corrections, biomechanics, etc.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

A. PATIENT-SPECIFIC IMPLANT DESIGN AND MANUFACTURING SYSTEM

FIG. 1 is a network connection diagram illustrating a computing system 100 for patient-specific medical care, according to an embodiment. As described in further detail herein, the system 100 is configured to generate a medical treatment plan based on patient data, patient-specific implants, radiographic images, or the like. The system 100 includes a client computing device 102, which can be a user device, such as a smart phone, mobile device, laptop, desktop, personal computer, tablet, phablet, or other such devices known in the art. As discussed further herein, the client computing device 102 can include one or more processors, and memory storing instructions executable by the one or more processors to perform the methods described herein. The client computing device 102 can be associated with a healthcare provider that is treating the patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The client computing device 102 and server 106 can individually or collectively perform the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice versa.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112*a*-112*c*, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114*a*-114*c*, collectively 114) associated with reference patients treated by the corresponding healthcare provider. The reference patient data sets 114 can include, for example, electronic medical records, electronic health records, biomedical data sets, biomechanical data sets, mobility data sets, pain data sets, intra-operative image data, payment information, insurance information, insurer information, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

The server 106 can receive at least some information from an intra-operative image system 141 (e.g., device(s) capturing radiographic images, fluoroscopic images, C-Arm device images, X-ray images, etc.). In some embodiments, the radiographic images are captured using an X-ray machine, a C-Arm machine, a fluoroscopic imaging device, etc. For example, the server 106 can be connected to the system 141 via one or more communication networks (not shown). The system 141 can include one or more outcome data databases, image databases, pre-op, intra-operative, and post-operative databases, or the like. The server 106 can request and retrieve data sets 117 from the system 141. The system 141 can include, without limitation, an X-ray machine, a fluoroscopic imaging device, a CT scanner, an MRI machine, or other imaging equipment that can be located approximate or within the surgical suite.

As described in further detail herein, the server 106 can be configured with one or more algorithms that generate patient-specific treatment plan data (e.g., treatment procedures, medical devices, etc.) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the depicted embodiment, the server 106 includes a data analysis module 116 and a surgical planning and confirmation platform 109 ("SPC platform 109"). The SPC platform 109 includes a treatment planning module 118, a surgical implant positioning manager 119, and a database 151. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments. For example, the SPC platform 109 can be incorporated into the data analysis module 116. In other embodiments, the modules of the system 100 can be combined with modules of other systems. For example, the SPC platform 109 can be part of or incorporated into a healthcare system 133 and can manage reconciliation of intra-operative implant positioning to surgical plans. The reconciliation can be outcome-driven reconciliation for reducing or eliminating intra-operative implant mispositioning that is likely to affect one or more outcomes more than acceptable threshold amount(s). The SPC platform 109 can include one or more multi-component implant design platforms.

The data analysis module 116 is configured with one or more algorithms for identifying a subset of reference data from the database 110 that is likely to be useful in developing a patient-specific treatment plan. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular healthcare provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or data sets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The SPC platform 109 can include the treatment planning module 118, the surgical implant positioning manager 119, and the database 151. The treatment planning module 118 is configured with one or more algorithms to generate at least one treatment plan (e.g., pre-operative plans, intra-operative plans, surgical plans, post-operative plans, etc.) based on the output from the data analysis module 116. In some embodiments, the treatment planning module 118 is configured to develop and/or implement at least one predictive model for generating plans. The predictive model(s) can be developed using clinical knowledge, statistics, machine learning, artificial intelligence (AI), neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output. Machine learning models can be trained to analyze pre-operative plans and intra-operative data to determine whether the position (e.g., location, orientation, etc.) of anatomical element(s), instrument(s), or implant(s) in a patient during a surgical procedure matches the position in the pre-operative plan. The treatment planning module 118 can perform all or some of the step discussed in connection with FIGS. 30-36.

In orthopedic procedures, the machine learning models can be trained to determine whether anatomical elements, such as bones and/or joints, are at targeted positions. The instruments can be surgical instruments for accessing surgical sites, implanting implants, anchoring (e.g., securing implants to bony tissue), or the like. In joint repair procedures, the anatomical elements can include bones, cartilage, connective tissue, and other anatomical elements that affect joint position and/or function. The instruments can be joint repair instruments. In spinal procedures, the position of anatomical elements can include soft tissue that may contribute to nerve compression. The system can identify tissue that can be removed to, for example, reduce nerve compression, facilitate implantation of implants, and/or perform other steps for decompression. The machine learning models can be trained based on the procedure to be performed.

The system 100 can predict intra-operative patient mobility and identify mobility related surgical steps. The system 100 can perform the techniques and methods disclosed in U.S. patent application Ser. No. 17/868,729, which is incorporated by reference in its entirety. For example, the SPC platform 109 can identify soft tissue surgical steps for adjusting intra-operative mobility of anatomical features to facilitate implantation at target locations. One or more predictive models can identify specific soft tissue (e.g., tissue of cartilage, ligaments, etc.) that can be cut, removed, or manipulated to achieve desired operative mobility of, for example, bones, organs, or other anatomical elements. The modified intra-operative ability can facilitate delivery and positioning of the implant. In some embodiments, the intra-operative mobility can be predicted prior to beginning of surgery, a sequence of surgical steps, or the like. In some embodiments, the system 100 can intra-operative generate surgical steps based on intra-operative data. This allows real-time intra-operative steps to be generated based on the current condition of the patient. In some procedures, a surgical plan can include soft tissue surgical steps to facilitate movement of anatomical elements, implantation of implants, or the like. Additionally, the methods and systems disclosed herein can be combined or used with techniques or methods disclosed in U.S. patent application Ser. No. 17/978,746, which is incorporated by reference in its entirety. For example, one or more decompression steps can be performed during the surgical procedure. Sites of nerve compression can be pre-operatively and/or intra-operatively identified. Targeted tissue that contributes to the nerve compression can be identified. The system 100 can develop one or more surgical steps for accessing and performing one or more decompression steps on the targeted tissue (e.g., removal and/or repositioning of targeted tissues). This allows for spinal decompression procedures to be performed to enhanced outcomes.

The treatment planning module 118 can be configured include one or more soft tissue surgical steps. The soft tissue surgical steps can facilitate movement of anatomical features to facilitate implantation. The soft tissue surgical steps can include severing, dissecting, cutting, and/or removing tissue. For example, ligaments (e.g., supraspinous ligament, interspinous ligaments, spinal ligaments, etc.) can be severed to access and move apart adjacent spinous processes, vertebral bodies, etc. In some example plans, the soft tissue surgical steps include one or more of severing soft tissue located along the patient's spine, removing at least a portion of an annulus, and/or resecting cartilage along the spine. The treatment planning module 118 can virtually move anatomical elements to identify soft tissue that inhibits or prevents desired movement, block access paths to implantation sites, etc. Simulations of soft tissue surgical steps can be performed to select recommended soft tissue surgical steps for achieving positionality of the anatomical elements.

In some example plans, the soft tissue surgical steps include one or more decompression procedures. The system can predict a decompression score for each decompression procedure. The nerve decompression score can be based on, for example, a predicted percentage decrease of pain felt by the patient. The system can generate a plurality of decompression plans, determine a decompression score (e.g., post-operative pain score, nerve decompression score, etc.) for each decompression plan, receive selection of one of the decompression plans, and generate a decompression surgical plan based on the selected decompression plan. The user can modify the selected decompression plan based on a corrected configuration of the patient's spine. The decompression plans can include at least one of a laminectomy, a laminotomy, a microdiscectomy, a foraminotomy, and/or an osteophyte procedure.

In some example plans, the planned surgical steps include one or more decompression steps for spinal procedures. The system can predict a decompression score for each decompression step, series of steps, and/or decompression procedure. The nerve decompression score can be based on, for example, a predicted percentage decrease of pain felt by the patient. The system can generate a plurality of decompression plans, determine a decompression score (e.g., post-operative pain score, nerve decompression score, etc.) for each decompression plan, receive selection of one of the decompression plans, and generate a decompression surgical plan based on the selected decompression plan. The user can modify the selected decompression plan based on a corrected configuration of the patient's spine. The decompression plans can include at least one of a laminectomy, a laminotomy, a microdiscectomy, a foraminotomy, and/or an osteophyte procedure.

The amount of movement of implants, anatomical elements, and other features of interest attributable to each step can be predicted to facilitate surgical planning and simulations. A simulation can predict joint mobility of the patient's spine or specific joints. A user can select one or more of the implant position(s) (e.g., pre-operative planned position, intra-operative planned position, predicted post-operative position based one or more loading conditions) identified surgical steps based on the simulated joint mobility, targeted corrective anatomical configuration, etc. The treatment planning module 118 can predict intra-operative joint mobility and/or post-operative joint mobility associated with the selected soft tissue surgical steps. This allows the user to select a surgical plan with surgical steps for helping reposition anatomical elements, implantation at targeted site(s), etc.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training data set can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient, meet one or more parameters (e.g., coverage parameters, reimbursement parameters, regulatory parameters, or the like). Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), cervical fusion, anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants, rotatable intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 118 can also store various types of implant surgery information, such as implant parameters (e.g., types, dimensions), availability of implants, aspects of a pre-operative plan (e.g., initial implant configuration, detection and measurement of the patient's anatomy, etc.), U.S. Food and Drug Administration (FDA) requirements for implants (e.g., specific implant parameters and/or characteristics for compliance with FDA regulations), or the like. In some embodiments, the treatment planning module 118 can convert the implant surgery information into formats useable for machine learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the client computing device 102 for output to a user (e.g., clinician, surgeon, healthcare provider, patient). In some embodiments, the client computing device 102 includes or is operably coupled to a display 122 for outputting the treatment plan(s). The display 122 can include a graphical user interface (GUI) for visually depicting various aspects of the treatment plan(s). For example, the display 122 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 122 can show a design for a medical device to be implanted in the patient, such as a two- or three-dimensional model of the device design. The display 122 can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

The surgical implant positioning manager 119 can analyze and manage confirmation of intra-operative positioning data, intra-operative data (e.g., radiographic images, ultrasound, MRI, etc.) and other information. The database 151 can search for, retrieve, and store data from systems 141 or other systems. For example, the server 106 can be trained to generate new treatment plans, and the database 151 can provide reconciliation of intra-op implant positioning to surgical plans. The database 151 can then retrieve the intra-operative data sets, pre-operative data sets, and post-operative data sets, from the system 141. The surgical implant positioning manager 119 can analyze and provide confirmation of intra-operative positioning of surgical implants based on the pre-operative plan. The surgical implant positioning manager 119 can compensate for the loading conditions of anatomical elements associated with the pre-operative data sets. For example, the surgical implant positioning manager 119 can modify the pre-operative data sets (or virtual model generated based on the pre-operative data sets) to compensate for differences in loading conditions of the pre-operative data sets (for example, the patient was standing to obtain pre-operative standing X-ray data) and intra-operative data sets with other loaded conditions (e.g., the patient is laying down).

In some embodiments, the medical device design(s) generated by the server 106 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

A healthcare provider (e.g., surgeon, nurse, surgical technician, etc.) can capture images of the patient 170 and/or the implant 161 at surgery site 172 with a computing device 174, such as a smartphone, tablet, scanner, imaging device, or the like. The treatment planning module 118 can determine one or more planned intra-operative modifications to the implant 161 based on the collected intra-operative data of the patient. In a first example, the treatment planning module 118 detects, based on the collected intra-operative data, that the healthcare provider intra-operatively reshaped a rod during the surgical procedure. In a second example, the treatment planning module 118 provides the healthcare provider with instructions (e.g., templates, angles, distances, parameters, etc.) to intra-operatively reshape a rod based on the collected intra-operative data. The intra-operative modifications made to the implant 161 can be monitored/detected with cameras to confirm that the implant 161 has the correct configuration (e.g., size, shape, geometry, etc.) and/or recommend additional reconfiguring based on the anatomy of the patient. The treatment planning module 118 can also intra-operatively determine whether all or some of the planned implants should be implanted, planned implants should be replaced with other implants, etc.

The system 100 can perform intra-operative simulations with, for example, virtual models, such as a virtual model of the patient's anatomy and a virtual model of the implant. As intra-operative data is collected, the system 100 can determine whether the patient's anatomy has been modified, such as through the removal of soft tissue, removal of bone, etc. Based on the modified anatomy, the system 100 can determine modifications to the implant and instruct a healthcare provider to modify the implant. The modifications to the implant can include implanting additional devices, replacing the implant, adjusting a level of expansion of the implant, selecting a different size implant from an available kit, fabricating the implant on-site at the surgical site, bending a rod, etc. For example, if the patient's bone is modified, the system can instruct the healthcare provider to bend a spinal rod to accommodate the modification to the patient's bone. The system 100 can determine instructions (e.g., templates, angles, distances, parameters) for the healthcare provider that specify how to modify the implant based on the collected intra-operative data. For example, a healthcare provider can receive bending information (e.g., angles) and reshape a rod based on the bending information. As the implant is being modified or after modification, the system 100 can review image data of the modified implant and confirm modification is correct or recommend additional modifications. The system 100 can determine, based on the collected intra-operative data, whether to modify the virtual model or to generate a new virtual model of the patient. The system 100 can request additional patient data (e.g., new images, patient metrics, etc.) and send an inquiry for the additional patient data. This process can be repeated any number of times during a surgical procedure to simulate one or more surgical steps, outcomes, etc.

Various types of manufacturing systems are suitable for use in accordance with the embodiments herein. Manufacturing can be achieved using human design, machine design, a combination of human and machine design, or other design techniques. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The manufacturing system 124, implant analyzer 129, and/or surgical implant positioning manager 119 can communicate directly with one another or via the communication network 104. The system 100 can perform one or more validation steps for a manufactured implant. The analyzer 129 can include one or more scanners, cameras, or imaging devices and can be incorporated into the manufacturing system 124 or other components of the system 100 and can scan the manufactured implant to, for example, identify manufacturing defects, confirm the implant meets one or regulatory requirements, etc. By analyzing implant characteristics (e.g., composition of the material, surface topology, etc.) and manufacturing parameters (e.g., composition of the material, temperature, speed of printing, manufacturing conditions, accuracy of printer, etc.), the system 100 can determine whether the implant should be implanted in a patient. If the implant is not acceptable, system 100 can determine manufacturing adjustments for the implant to be remanufactured. The analyzer 129 can be onsite manufacturing scanners or imager positioned to scan or image implants during and/or after fabrication. For example, the analyzers 129 can be located at a healthcare provider (e.g., at a hospital, clinic, surgical suite, etc.) to allow quality control checking immediately prior to implantation, verification of regulatory compliance, etc. In some embodiments, the analyzer 129 analyzes modifications (e.g., preoperative modifications, intraoperative modifications, etc.) to the implant. For example, user may preoperatively modify an implant based on preoperative scans prior to starting surgery. The analyzer 129 can be used to collect data (e.g., images, scans, etc.) of the modified implant to determine whether the modified implant meets one or more criteria for implantation. In response to the implant not meeting the one or more criteria, the user can perform additional modifications to the implant until the implant is suitable for implantation. In some embodiments, the implant can be intraoperatively modified. The analyzer 129 can be located on site (e.g., at a surgical suite, a hospital, surgical setting, etc.) for performing near real-time and/or real-time analyses of the modified implant. Additionally, the analyzer 129 can analyze one, some, or all components of a surgical kits to, for example, determine whether the components are compatible with one another, whether the kit is predicted to achieve a target patient outcome, etc. In some embodiments, the analyzers 129 are offsite of the manufacturing location. For example, the manufacturing can be offsite and the analyzer 129 can be at the surgery site.

The manufacturing system 124 can manufacture all or some of the components of a kit. The kit components can be selected based on requirement(s), including regulatory requirements, reimbursement requirements, or other requirements. Surgical kits can include one or more implants, instruments, instructions for use, and reusable and disposable components. The kit requirements can be retrieved from a database 151. The system 100 can synchronize the surgical plan with the requirements to generate patient-specific surgical kits meeting the requirements.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 118 generates control instructions configured to cause a surgical robot (e.g., robotic surgery systems, navigation systems, etc.) to partially or fully perform a surgical procedure. The control instructions can be transmitted to the robotic apparatus by the client computing device 102 and/or the server 106.

Following the treatment of the patient in accordance with the treatment plan, treatment progress can be monitored over one or more time periods to update the data analysis module 116 and/or treatment planning module 118. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110 the data analysis module 116, and/or the treatment planning module 118 can be located across a plurality of different servers, computing systems, or other types of cloud-computing resources, rather than at a single server 106 or client computing device 102.

The treatment planning module 118 can communicate with the surgical implant positioning manager 119 to obtain intra-operative data. The display 122 can display an intra-operative data 123 and pre-operative data 127 virtually overlaid on each other to illustrate the placement and position of the implant 161. A user can review proposed pathology 131, a treatment plan 157, and implant(s) 161. The treatment plan 157 can be an interactive plan having a user input element 165 (e.g., one or more buttons, a drop-down menu, toggle, etc.) for modification and/or approval. The intra-operative data 123 and pre-operative data 127 can be dynamically updated based on the user input. This allows a user to identify the intra-op positioning of surgical implants based on the pre-operative plan. The display 122 can graphically overlay an intra-operative image over a pre-operative plan/model/image. A user (e.g., healthcare provider, such as a surgeon) can manipulate (e.g., zoom, stretch, crop, and/or rotate) the intra-operative image to align with the pre-operative model (e.g., virtual 3D model), images (e.g., images of virtual models), anatomical renderings, or other images displaying anatomical position information on the device. In some cases, a user can zoom, stretch, and/or rotate the virtual 3D model (or other pre-operative images) to align with the intra-operative image on the device or other viewing platform. In some embodiments, the treatment planning module 118 can analyze pre-operative data and then manipulate pre-operative data (e.g., pre-operative images, virtual 3D models, etc.) to align or otherwise synchronize the pre-operative and intra-operative data. For example, the treatment planning module 118 can generate images of a virtual 3D model of patient anatomy in a corrected configuration such that those images match intra-operative images. The treatment planning module 118 can use a machine learning engine to align anatomical features in the virtual 3D model with corresponding anatomical features in the images by, for example, manipulating the virtual 3D model, images, or both. The virtual 3D model can include, for example, representations of patient's anatomy, implants, instruments, or other models disclosed herein.

The system 100 is configured to determine one or more measurements to confirm implant placement. For example, the system 100 calculates a difference (e.g., delta, deviation, etc.) between the intra-operative data and the pre-operative plan. Display 122 can display the measurements to a user. In some implementations, display 122 shows, during a surgical procedure, a live comparison between the intra-operative data and the pre-operative plan. In some embodiments, a threshold delta can be determined by the system 100, inputted by a user, or the like. The system 100 can notify the user if the measurement exceeds the threshold delta. In some procedures, the threshold delta can be based on implantation envelopes, boundaries, or other targeting features determined by the system 100, user, or the like. For example, a user can draw a two-dimensional or three-dimensional boundary on anatomical images for acceptable positions of the implant. The system 100 can then determine whether the implant, or sufficient amount of the implant, is positioned within the boundary. System 100 can calculate a completion score for a surgical procedure and display the score on display 122. In an illustrative example, a device captures an intra-operative image and displays the intra-operative image over the pre-operative plan. System 100 can scale and orient the intra-operative image to closely match the pre-operative plan, reflecting the location of anatomical landmarks and implant. The matching can be performed using one or more segmentation program, best fit algorithms, image manipulation programs, or the like.

System 100 can display, correlate, and/or measure the planned position of an implant and the current location of the implant to help healthcare providers properly implant and position an implant in a patient. Additionally, system 100 can compare post-operative imaging to pre-operative models, intra-operative images, and treatment plans, according to the techniques described herein. System 100 can utilize the techniques described herein for multiple stage surgeries (e.g., anterior surgery performed first, posterior surgery performed next, lateral surgery performed next, etc.). System 100 can perform confirmation of placement of implant based on surgical plan or monitoring migration during other aspects of patient care or subsequent surgery. The system 100 can predict post-operative outcomes based on, for example, the monitoring, local anatomical environment conditions. Image analysis can be used to determine/predict post-operative mobility (e.g., anatomical configurations, mobility after surgical intervention, etc.) based, at least in part, on the intra-operative data, disease progression scores, etc.

The system 100 is configured to design the physical patient-specific implants 154, 156 for achieving the approved planned pathology 131. Example implants 154 include, without limitation, non-expandable cages, expandable cages, artificial discs, and interbody devices. The implant 156 can include a posterior fixation system. Example posterior fixation systems can include, without limitation, one or more spinal rods, rod holders, rod couple, anchors (e.g., bone anchors, tissue anchors, etc.), anchor assemblies, couplers, or the like. The implant 154 can include, without limitation, interspinous spacers, artificial discs, or the like. The surgical implant positioning manager 119 can also retrieve information regarding the patient's anatomy, such as pre-operative measurements, two- or three-dimensional images or models of the anatomy, and/or information regarding the biology, geometry, and/or mechanical properties of the anatomy. Example designing of implants is discussed in connection with FIGS. 3-13 and 30-36.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
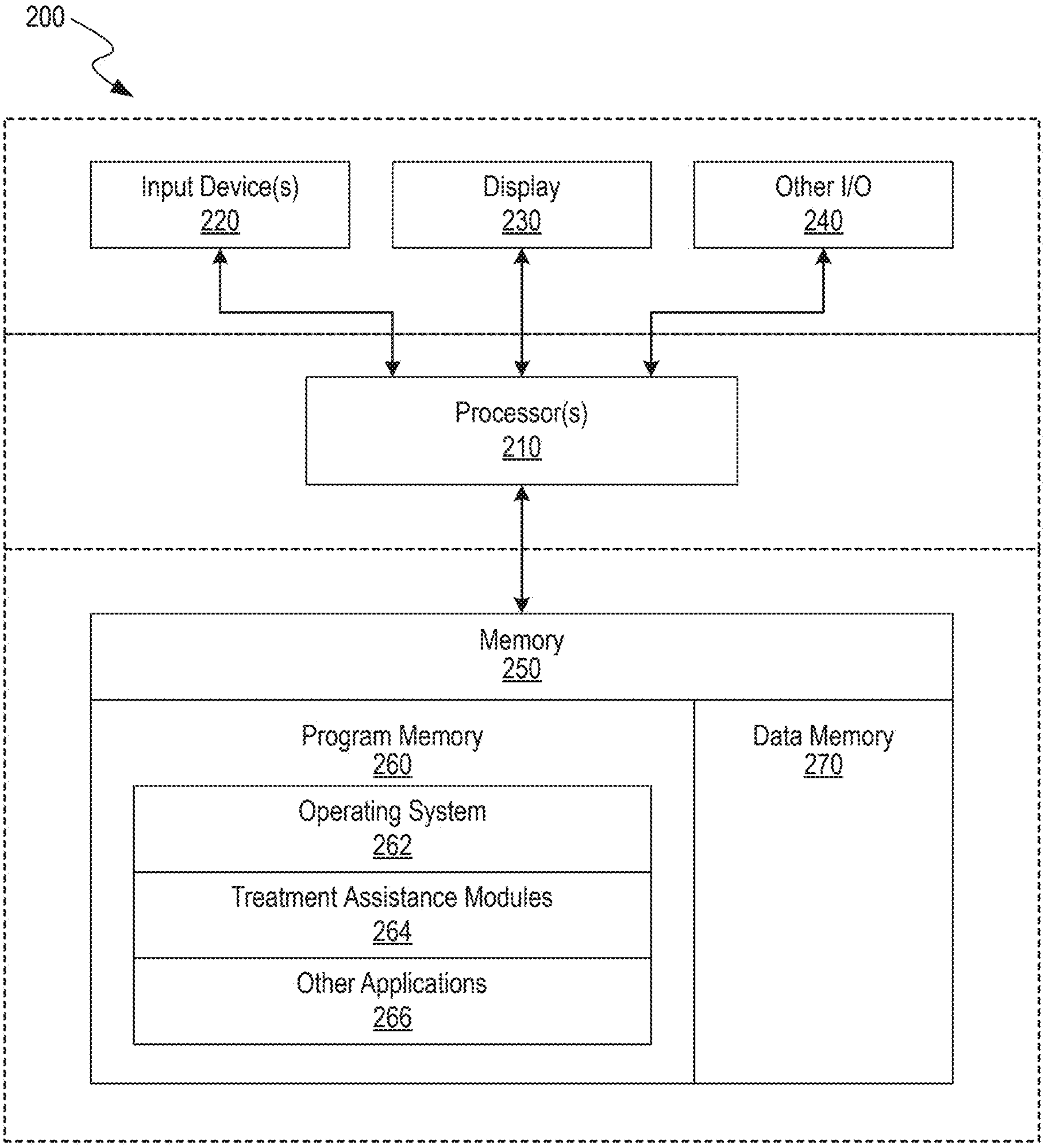
FIG. 2 illustrates a computing device suitable for use in connection with the system of FIG. 1, according to an embodiment.

FIG. 2 illustrates a computing or user device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
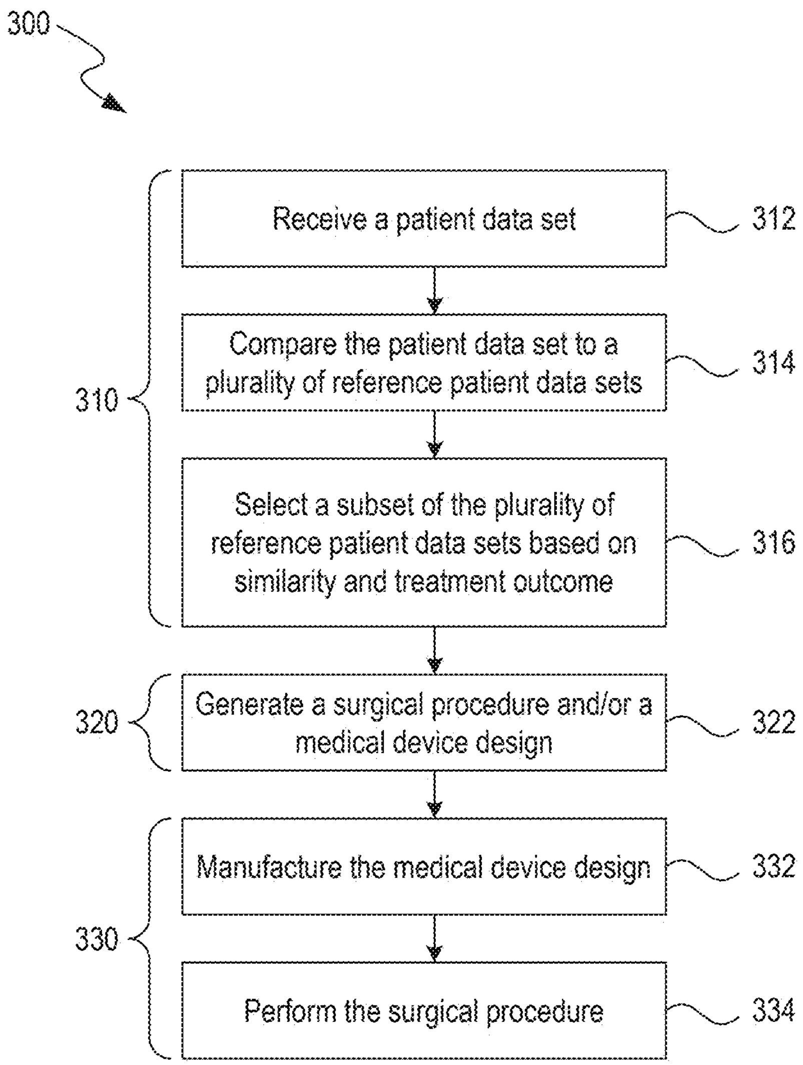
FIG. 3 is a flow diagram illustrating a method for providing patient-specific medical care, according to an embodiment.

FIG. 3 is a flow diagram illustrating a method 300 for providing patient-specific medical care, according to an embodiment. The method 300 can include a data phase 310, a modeling phase 320, and an execution phase 330. The data phase 310 can include collecting data of a patient to be treated (e.g., pathology data), and comparing the patient data to reference data (e.g., prior patient data such as pathology, surgical, and/or outcome data). For example, a patient data set can be received (block 312). The patient data set can be compared to a plurality of reference patient data sets (block 314), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, coronal offset distance, segment flexibility, LL-PI is greater than predetermined degrees (e.g., 5 degrees, 10 degrees, etc.), LL-PI mismatch (e.g., age-adjusted), sagittal vertical axis offset distance, coronal offset distance, coronal angle, bone quality, rotational displacement, or treatment level of the spine.

A subset of the plurality of reference patient data sets can be selected (block 316), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications. In some embodiments, the data is or includes an outcome score, which can be calculated based on a single target outcome, an aggregate outcome, and/or an outcome threshold.

Optionally, the data analysis phase 310 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, or implant placement. The at least one medical device design can include data representing one or more of physical properties, mechanical properties, or biological properties of a corresponding medical device. In some embodiments, the at least one patient-specific medical device design includes a design for an implant or an implant delivery instrument.

In the modeling phase 320, a surgical procedure and/or medical device design is generated (block 322). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data analysis phase 310. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 330 can include manufacturing the medical device design (block 332). In some embodiments, the medical device design is manufactured by a manufacturing system configured to perform one or more of additive manufacturing, 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 330 can optionally include generating fabrication instructions configured to cause the manufacturing system to manufacture a medical device having the medical device design.

The execution phase 330 can include performing the surgical procedure (block 334). The surgical procedure can involve implanting a medical device having the medical device design into the patient. The surgical procedure can be performed manually, by a surgical robot, or a combination thereof. In embodiments where the surgical procedure is performed by a surgical robot, the execution phase 330 can include generating control instructions configured to cause the surgical robot to perform, at least partly, the patient-specific surgical procedure.

The method 300 can be implemented and performed in various ways. In some embodiments, one or more steps of the method 300 (e.g., the data phase 310 and/or the modeling phase 320) can be implemented as computer-readable instructions stored in memory and executable by one or more processors of any of the computing devices and systems described herein (e.g., the system 100), or a component thereof (e.g., the client computing device 102 and/or the server 106). Alternatively, one or more steps of the method 300 (e.g., the execution phase 330) can be performed by a healthcare provider (e.g., physician, surgeon), a robotic apparatus (e.g., a surgical robot), a manufacturing system (e.g., manufacturing system 124), or a combination thereof. In some embodiments, one or more steps of the method 300 are omitted (e.g., the execution phase 330).

FIGS. 4A-4C illustrate exemplary data sets that may be used and/or generated in connection with the methods described herein (e.g., the data analysis phase 310 described with respect to FIG. 3), according to an embodiment. FIG. 4A illustrates a patient data set 400 of a patient to be treated. The patient data set 400 can include a patient ID and a plurality of pre-operative patient metrics (e.g., age, gender, BMI, lumbar lordosis (LL), pelvic incidence (PI), and treatment levels of the spine (levels)). FIG. 4B illustrates a plurality of reference patient data sets 410. In the depicted embodiment, the reference patient data sets 410 include a first subset 412 from a study group (Study Group X), a second subset 414 from a practice database (Practice Y), and a third subset 416 from an academic group (University Z). In alternative embodiments, the reference patient data sets 410 can include data from other sources, as previously described herein. Each reference patient data set can include a patient ID, a plurality of pre-operative patient metrics (e.g., age, gender, BMI, lumbar lordosis (LL), pelvic incidence (PI), and treatment levels of the spine (levels)), treatment outcome data (Outcome) (e.g., presence of fusion (fused), HRQL, complications), and treatment procedure data (Surg. Intervention) (e.g., implant design, implant placement, surgical approach).

FIG. 4C illustrates comparison of the patient data set 400 to the reference patient data sets 410. As previously described, the patient data set 400 can be compared to the reference patient data sets 410 to identify one or more similar patient data sets from the reference patient data sets. In some embodiments, the patient metrics from the reference patient data sets 410 are converted to numeric values and compared the patient metrics from the patient data set 400 to calculate a similarity score 420 ("Pre-op Similarity") for each reference patient data set. Reference patient data sets having a similarity score below a threshold value can be considered to be similar to the patient data set 400. For example, in the depicted embodiment, reference patient data set 410*a* has a similarity score of 9, reference patient data set 410*b* has a similarity score of 2, reference patient data set 410*c* has a similarity score of 5, and reference patient data set 410*d* has a similarity score of 8. Because each of these scores are below the threshold value of 10, reference patient data sets 410*a-d* are identified as being similar patient data sets.

The treatment outcome data of the similar patient data sets 410*a-d* can be analyzed to determine surgical procedures and/or implant designs with the highest probabilities of success. For example, the treatment outcome data for each reference patient data set can be converted to a numerical outcome score 430 ("Outcome Quotient") representing the likelihood of a favorable outcome. In the depicted embodiment, reference patient data set 410*a* has an outcome score of 1, reference patient data set 410*b* has an outcome score of 1, reference patient data set 410*c* has an outcome score of 9, and reference patient data set 410*d* has an outcome score of 2. In embodiments where a lower outcome score correlates to a higher likelihood of a favorable outcome, reference patient data sets 410*a*, 410*b*, and 410*d* can be selected. The treatment procedure data from the selected reference patient data sets 410*a*, 410*b*, and 410*d* can then be used to determine at least one surgical procedure (e.g., implant placement, surgical approach) and/or implant design that is likely to produce a favorable outcome for the patient to be treated.

In some embodiments, a method for providing medical care to a patient is provided. The method can include comparing a patient data set to reference data. The patient data set and reference data can include any of the data types described herein. The method can include identifying and/or selecting relevant reference data (e.g., data relevant to treatment of the patient, such as data of similar patients and/or data of similar treatment procedures), using any of the techniques described herein. A treatment plan can be generated based on the selected data, using any of the techniques described herein. The treatment plan can include one or more treatment procedures (e.g., surgical procedures, instructions for procedures, models or other virtual representations of procedures), one or more medical devices (e.g., implanted devices, instruments for delivering devices, surgical kits), or a combination thereof.

In some embodiments, a system for generating a medical treatment plan is provided. The system can compare a patient data set to a plurality of reference patient data sets, using any of the techniques described herein. A subset of the plurality of reference patient data sets can be selected, e.g., based on similarity and/or treatment outcome, or any other technique as described herein. A medical treatment plan can be generated based at least in part on the selected subset, using any of the techniques described herein. The medical treatment plan can include one or more treatment procedures, one or more medical devices, or any of the other aspects of a treatment plan described herein, or combinations thereof.

In further embodiments, a system is configured to use historical patient data. The system can select historical patient data to develop or select a treatment plan, design medical devices, or the like. Historical data can be selected based on one or more similarities between the present patient and prior patients to develop a prescriptive treatment plan designed for desired outcomes. The prescriptive treatment plan can be tailored for the present patient to increase the likelihood of the desired outcome. In some embodiments, the system can analyze and/or select a subset of historical data to generate one or more treatment procedures, one or more medical devices, or a combination thereof. In some embodiments, the system can use subsets of data from one or more groups of prior patients, with favorable outcomes, to produce a reference historical data set used to, for example, design, develop or select the treatment plan, medical devices, or combinations thereof.

Figure 5:
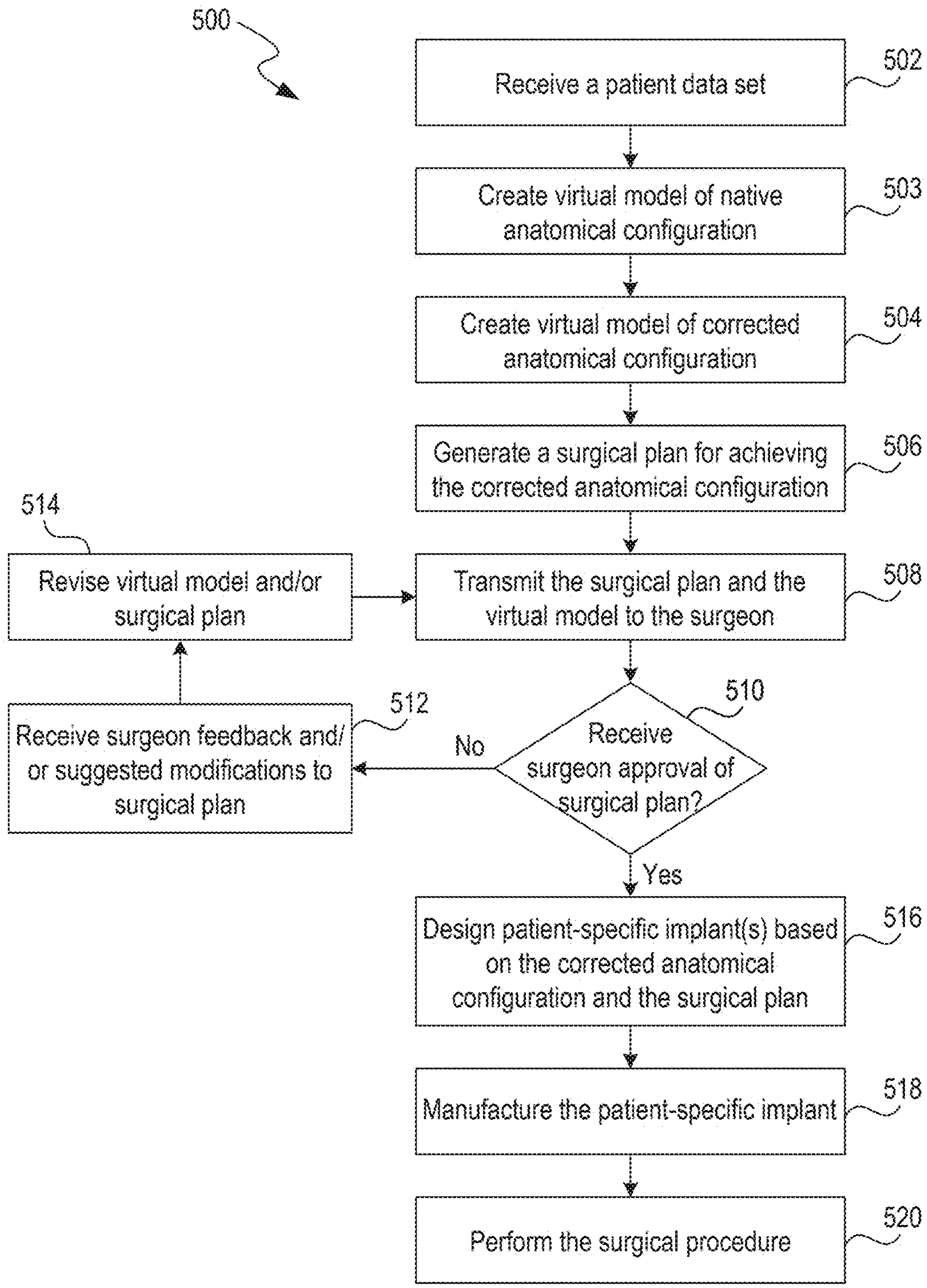
FIG. 5 is a flow diagram illustrating another method for providing patient-specific medical care, according to an embodiment.

FIG. 5 is a flow diagram illustrating a method 500 for providing patient-specific medical care, according to another embodiment of the present technology. The method 500 can begin in step 502 by receiving a patient data set for a particular patient in need of medical treatment. The patient data set can include data representative of the patient's condition, anatomy, pathology, symptoms, medical history, preferences, intra-operative data, and/or any other information or parameters relevant to the patient. For example, the patient data set 850 can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The patient data set can also include image data, such as camera images, Magnetic Resonance Imaging (MRI) images, ultrasound images, Computerized Aided Tomography (CAT) scan images, Positron Emission Tomography (PET) images, X-ray images, and the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. The patient data set can be received at a server, computing device, or other computing system. For example, in some embodiments the patient data set can be received by the server 106 shown in FIG. 1. In some embodiments, the computing system that receives the patient data set in step 502 also stores one or more software modules (e.g., the data analysis module 116 and/or the treatment planning module 118, shown in FIG. 1, or additional software modules for performing various operations of the method 500). Additional details for collecting and receiving the patient data set are described below with respect to FIGS. 6-7D.

In some embodiments, the received patient data set can include disease metrics such as lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 500 includes determining (e.g., automatically determining) one or more of the disease metrics based on the patient image data, as described below.

Once the patient data set is received in step 502, the method 500 can continue in step 503 by creating a virtual model of the patient's native anatomical configuration (also referred to as "pre-operative anatomical configuration"). The virtual model can be based on the image data included in the patient data set received in step 502. For example, the same computing system that received the patient data set in step 502 can analyze the image data in the patient data set to generate a virtual model of the patient's native anatomical configuration. The virtual model can be a two- or three-dimensional visual representation of the patient's native anatomy. The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 8A and 8B. In some embodiments, the method 500 can optionally omit creating a virtual model of the patient's native anatomy in step 503, and proceed directly from step 502 to step 504.

In some embodiments, the computing system that generated the virtual model in step 502 can also determine (e.g., automatically determine or measure) one or more disease metrics of the patient based on the virtual model. For example, the computing system may analyze the virtual model to determine the patient's pre-operative lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 500 can continue in step 504 by creating a virtual model of a corrected anatomical configuration (which can also be referred to herein as the "planned configuration," "optimized geometry," "post-operative anatomical configuration," or "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4C (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, etc.). Target post-operative metrics can include, but are not limited to, target coronal parameters, target sagittal parameters, target pelvic incidence angle, target Cobb angle, target shoulder tilt, target iliolumbar angle, target coronal balance, target Cobb angle, target lordosis angle, and/or a target intervertebral space height. The different between the native anatomical configuration and the corrected anatomical configuration may be referred to as a "patient-specific correction" or "target correction."

Once the corrected anatomical configuration is determined, the computing system can generate a two- or three-dimensional visual representation of the patient's anatomy with the corrected anatomical configuration. As with the virtual model created in step 503, the virtual model of the patient's corrected anatomical configuration can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region in a corrected anatomical configuration, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 9A-1-9B-2.

In step 504, images of the patient can be segmented to isolate separate anatomic elements of the anatomy of interest. The spatial relationships between the isolated anatomic elements can be modified to generate a target or corrected patient pathology. The modifications can be selected based on regulatory criteria, financial parameters, etc. Other techniques can be used to generate anatomical configurations based on the available patient data.

The method 500 can continue in step 506 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, etc.) across a specific range of vertebral levels (e.g., L1-L4, L1-5, L3-T12, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, coronal parameters, sagittal parameters, and/or pelvic parameters) corresponding to the expected post-operative patient anatomy. The surgical plan can be generated by the same or different computing system that created the virtual model of the corrected anatomical configuration. In some embodiments, the surgical plan can also be based on one or more reference patient data sets as previously described with respect to FIGS. 1-4C. In some embodiments, the surgical plan can also be based at least in part on surgeon-specific preferences and/or outcomes associated with a specific surgeon performing the surgery. In some embodiments, more than one surgical plan is generated in step 506 to provide a surgeon with multiple options. An example of a surgical plan is described below with respect to FIG. 10.

After the virtual model of the corrected anatomical configuration is created in step 504 and the surgical plan is generated in step 506, the method 500 can continue in step 508 by transmitting the virtual model of the corrected anatomical configuration and the surgical plan, including interactive surgical plans, for surgeon review. In some embodiments, the virtual model and the surgical plan are transmitted as a surgical plan report, an example of which is described with respect to FIG. 11. In some embodiments, the same computing system used in steps 502-506 can transmit the virtual model and surgical plan to a computing device for surgeon review (e.g., the client computing device 102 described in FIG. 1). This can include directly transmitting the virtual model and the surgical plan to the computing device or uploading the virtual model and the surgical plan to a cloud or other storage system for subsequent downloading. Although step 508 describes transmitting the surgical plan and the virtual model to the surgeon, one skilled in the art will appreciate from the disclosure herein that images of the virtual model may be included in the surgical plan transmitted to the surgeon, and that the actual model need not be included (e.g., to decrease the file size being transmitted). Additionally, the information transmitted to the surgeon in step 508 may include the virtual model of the patient's native anatomical configuration (or images thereof) in addition to the virtual model of the corrected anatomical configuration. In embodiments in which more than one surgical plan is generated in step 506, the method 500 can include transmitting more than one surgical plan to the surgeon for review and selection.

The surgeon can review the virtual model and surgical plan and, in step 510, either approve or reject the surgical plan (or, if more than one surgical plan is provided in step 508, select one of the provided surgical plans). If the surgeon does not approve the surgical plan in step 510, the surgeon can optionally provide feedback and/or suggested modifications to the surgical plan (e.g., by adjusting the virtual model or changing one or more aspects about the plan). Accordingly, the method 500 can include receiving (e.g., via the computing system) the surgeon feedback and/or suggested modifications. If surgeon feedback and/or suggested modifications are received in step 512, the method 500 can continue in step 514 by revising (e.g., automatically revising via the computing system) the virtual model and/or surgical plan based at least in part on the surgeon feedback and/or suggested modifications received in step 512. In some embodiments, the surgeon does not provide feedback and/or suggested modifications if they reject the surgical plan. In such embodiments, step 512 can be omitted, and the method 500 can continue in step 514 by revising (e.g., automatically revising via the computing system) the virtual model and/or the surgical plan by selecting new and/or additional reference patient data sets. The revised virtual model and/or surgical plan can then be transmitted to the surgeon for review. Steps 508, 510, 512, and 514 can be repeated as many times as necessary until the surgeon approves the surgical plan. Although described as the surgeon reviewing, modifying, approving, and/or rejecting the surgical plan, in some embodiments the surgeon can also review, modify, approve, and/or reject the corrected anatomical configuration shown via the virtual model.

Once surgeon approval of the surgical plan is received in step 510, the method 500 can continue in step 516 by designing (e.g., via the same computing system that performed steps 502-514) a patient-specific implant based on the corrected anatomical configuration and the surgical plan. The implant(s) (e.g., implants 154 or 161 of FIG. 1) can be designed by mapping a negative space between the anatomic elements and filling at least a portion of the negative space with a medical virtual implant. U.S. application Ser. No. 16/569,494 discloses techniques for generating corrected patient pathologies, mapping spaces, designing implants, and manufacturing implants. U.S. application Ser. No. 16/569,494 is incorporated by reference in its entirety.

The patient-specific implant can be specifically designed such that, when it is implanted in the particular patient, it directs the patient's anatomy to occupy the corrected anatomical configuration (e.g., transforming the patient's anatomy from the native anatomical configuration to the corrected anatomical configuration). The patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, the patient-specific implant is designed solely based on the virtual model of the corrected anatomical configuration and/or without reference to pre-operative patient images.

The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.). Example patient-specific implants and implant systems designed via the method 500 is described below with respect to FIGS. 12-40.

In some embodiments, designing the implant in step 516 can optionally include generating fabrication instructions for manufacturing the implant. For example, the computing system may generate computer-executable fabrication instructions that that, when executed by a manufacturing system, cause the manufacturing system to manufacture the implant. For example, a virtual 3D model of the one or more patient-specific implants can be created based on filling of negative spaces between anatomical elements of the corrected patient pathology. The virtual 3D model can be converted into 3D fabrication data for manufacturing the one or more patient-specific implants.

In some embodiments, the patient-specific implant is designed in step 516 only after the surgeon has reviewed and approved the virtual model with the corrected anatomical configuration and the surgical plan. Accordingly, in some embodiments, the implant design is neither transmitted to the surgeon with the surgical plan in step 508, nor manufactured before receiving surgeon approval of the surgical plan. Without being bound by theory, waiting to design the patient-specific implant until after the surgeon approves the surgical plan may increase the efficiency of the method 500 and/or reduce the resources necessary to perform the method 500.

The method 500 can continue in step 518 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively or additionally, the implant can be manufactured using subtractive manufacturing techniques, such as CNC machining, electrical discharge machining (EDM), grinding, laser cutting, water jet machining, manual machining (e.g., milling, lathe/turning), or like technologies, or combinations thereof. The implant may be manufactured by any suitable manufacturing system (e.g., the manufacturing system 124 shown in FIG. 1). In some embodiments, the implant is manufactured by the manufacturing system executing the computer-readable fabrication instructions generated by the computing system in step 516.

Once the implant is manufactured in step 518, the method 500 can continue in step 520 by implanting the patient-specific implant into the patient. The surgical procedure can be performed manually, by a robotic surgical platform (e.g., a surgical robot), or a combination thereof. In embodiments in which the surgical procedure is performed at least in part by a robotic surgical platform, the surgical plan can include computer-readable control instructions configured to cause the surgical robot to perform, at least partly, the patient-specific surgical procedure.

The method 500 can be implemented and performed in various ways. In some embodiments, steps 502-516 can be performed by a computing system associated with a first entity, step 518 can be performed by a manufacturing system associated with a second entity, and step 520 can be performed by a surgical provider, surgeon, and/or robotic surgical platform associated with a third entity. During the surgical procedure, method 500 can collect intra-operative data. Any of the foregoing steps may also be implemented as computer-readable instructions stored in memory and executable by one or more processors of the associated computing system(s). In some implementations, steps 502-514 are performed with intra-operative data to provide confirmation that the location and position of the implant during a surgical procedure is within a threshold (e.g., delta threshold) of the pre-operative plan.

Figure 6A:
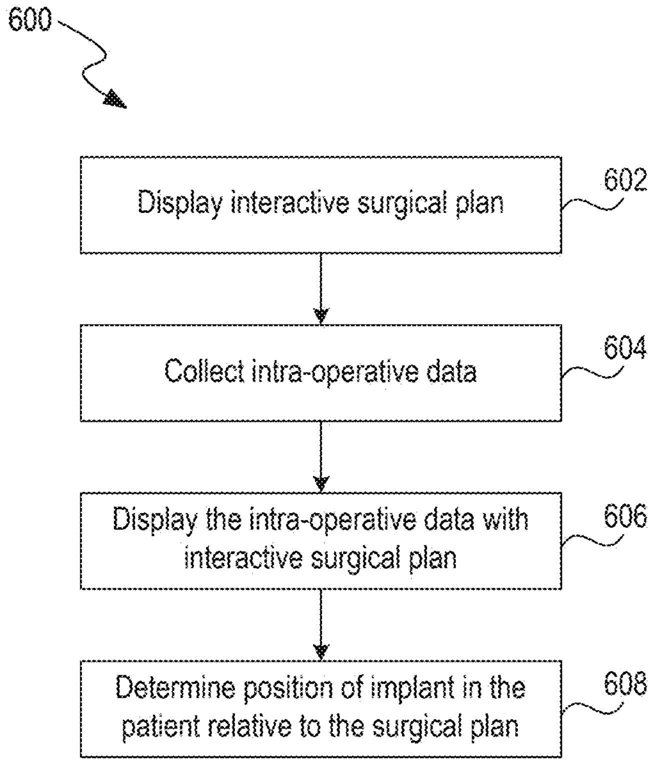
FIGS. 6A and 6B are flow diagrams illustrating methods for providing confirmation of intra-operative positioning of surgical implants, according to an embodiment.

FIG. 6A is a flow diagram illustrating a method 600 for providing confirmation of intra-operative positioning of surgical implants, according to another embodiment of the present technology.

The method 600 can begin in step 602 by displaying an interactive plan generated based on patient data. A patient-specific interactive surgical plan (e.g., plan 157 of FIG. 1, plan 1000 of FIG. 10A, plan 1020 of FIG. 10B, or overlaid image 1060 of FIG. 10C) includes a viewable planned pathology for the patient and is configured to receive user input. The pre-operative and/or intra-operative pathology can be used to validate a diagnosis, qualifying conditions for treatment, or the like based on pre-operative measurements, such as lumbar lordosis, Cobb angle(s), pelvic incidence, disc height(s), coronal offset distance, segment flexibility, LL-PI is greater than predetermined degrees (e.g., 5 degrees, 10 degrees, 15 degrees, etc.), LL-PI mismatch (e.g., age-adjusted), sagittal vertical axis offset distance, coronal offset distance, coronal angle, bone quality, and other metrics disclosed herein. Example displayed interactive plans and viewable pathologies are discussed in connection with FIGS. 7A-11.

The method 600 can continue in step 604 by collecting intra-operative data during a procedure involving a patient-specific implant. For example, a device (e.g., fluoroscopy device, radiographic device, C-Arm device, ultrasound device, MRI device, X-ray device, tablet, camera, etc.) can capture intra-operative data (e.g., continuous imaging, images, etc.) of a patient during a procedure to install the implant in the patient. The method 600 can collect the intra-operative data randomly, periodically, continuously, or at designated stages of the procedure of installing an implant. In some implementations, the intra-operative data is collected continuously to create a "live" feed of the medical procedure.

In step 606, the method 600 can display the intra-operative data with the interactive surgical plan. For example, method 600 can overlay the intra-operative data on the pre-operative plan to illustrate any differences between the intra-operative data and the pre-operative plan. The intra-operative images and pre-operative images can be configured (adjusted) to be virtually overlaid on each other. In some embodiments, the method 600 can include overlaying portions of pre-operative images onto the intra-operative images. The intra-operative images can be segmented to isolate anatomical elements. The segmented anatomical elements can be overlayed onto the pre-operative images to show differences between the planned and actual positions of anatomical elements. The method 600 can use machine learning or other algorithms to identify matching features in the intra-operative and pre-operative images. In other embodiments, the anatomical elements of pre-operative plans can be overlayed onto the intra-operative images. The facing and relative positions of the anatomical elements in the pre-operative images can be compared with the actual positions in the intra-operative images. The method 600 can compensate for loading conditions of the pre-operative images. For example, if the patient has pre-operative standing X-rays, the method 600 can modify the relative positions of anatomical elements based on the intra-operative loading of the patient. For example, if the patient is laying horizontally, the method 600 can move the anatomical elements of the pre-operative images to match an unloaded or laying down condition. Accordingly, pre-operative images can be manipulated or modified based on various loading conditions, patient positions, etc.

Method 600 can match landmarks (e.g., anatomical landmarks, implant landmarks, etc.), reference features, etc. to synchronize or nearly synchronize the intra-operative and pre-operative images. The landmarks can be selected by the system based upon individually identifiable anatomical elements. In some embodiments, a user can select and identify landmarks. For example, a user can review a surgical plan and identify one of more landmarks in pre-operative images, virtual models, images of anatomical models, or the like. The synchronization routine can be selected based on the desired accuracy of placement of the implant. If an implant is to be positioned near nerve tissue (e.g., the spinal cord), the user can select a synchronization routine to ensure that the implant is appropriately spaced apart from the spinal cord. Fixation elements (e.g., bone screws, fixation plates, etc.) can be used to limit or prevent migration of the implant post operation. Method 600 can use machine learning or artificial intelligence to align the images by zooming, stretching, and/or rotating the images on a viewing platform (e.g., user interface, screen, virtual model, etc.). In some implementations, method 600 compares the intra-operative data to the pre-operative plan and displays indications (e.g., tags, highlights, boxes, arrows, etc.) on the interactive surgical plan of any differences between the intra-operative data and pre-operative plan. In some embodiments, the method 600 allows a user to manipulate the images via viewing platform. For example, the user can manually zoom, stretch, crop, rotate, or otherwise manipulate images to achieve desired synchronization. The user can select images, adjust images, and control synchronization. In some embodiments, the method 600 includes analyzing manipulation of images performed by the user. The 600 can generate additional planned images by manipulating one or more pre-operative virtual models to generate additional images. This allows a user to review planned images that match the perspective and scale of intra-operative images. In fluoroscopic imaging, the method 600 can dynamically overlay pre-operative planned images onto continuous real-time fluoroscopic imaging. If the fluoroscopic imaging device is moved, the system can dynamically move the planned images to key those images to the fluoroscopic imaging. This allows the surgical team to obtain images of the patient from different viewing perspectives in real-time while continually viewing the targeted position for the implant.

In step 608, the method 600 can determine whether the position of the implant in the intra-operative data matches the placement in the pre-operative plan. Method 600 can determine if the position of the implant in the intra-operative data matches the placement in the pre-operative plan by determining if the orientation and location of the implant in the patient is the same as the pre-operative plan. The criteria for determining whether the intra-operative data matches a placement can be selected based on the procedure. In some embodiments, the criteria can be generated using machine learning, implemented by the user, or obtained from a database with matching recommendations. The criteria can include, for example, deviations, deltas, distance between intra-operative position and planned position, distances between the implant and anatomical elements (e.g., landmarks, nontargeted anatomical elements, nerves, etc.), interfaces (e.g., interfaces between the implant and anatomical elements, or combinations thereof), etc.

Figure 6B:
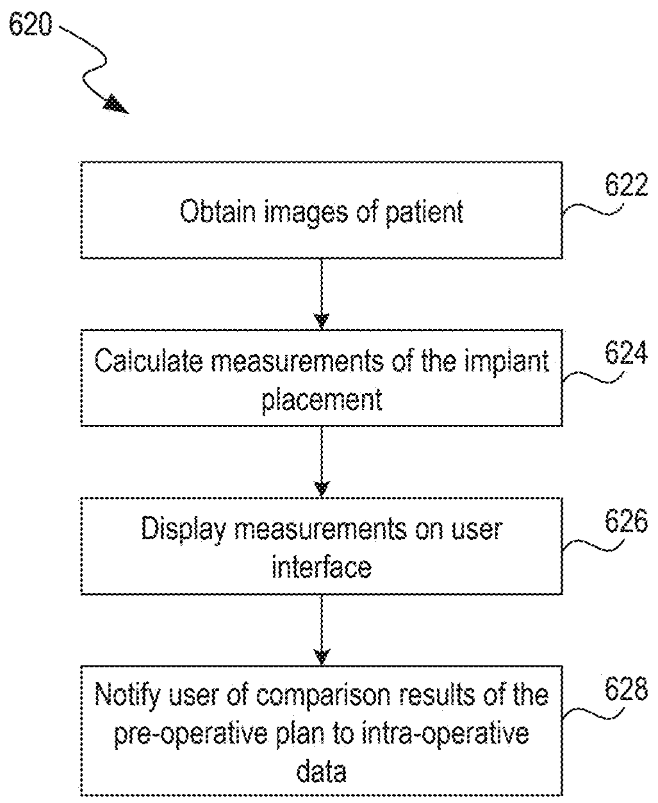
Figure 7A:
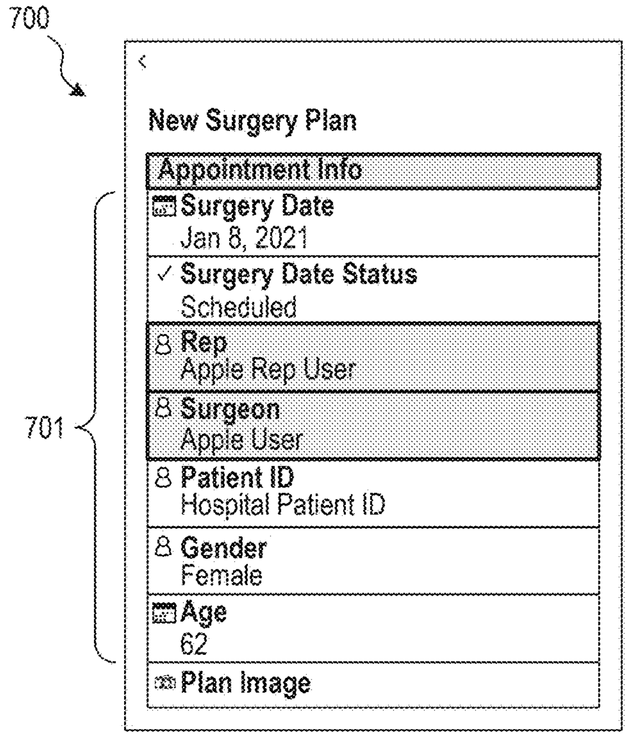
FIGS. 7A-7D illustrate an exemplary patient data set that may be used and/or generated in connection with the methods described herein, according to an embodiment.
Figure 7B:
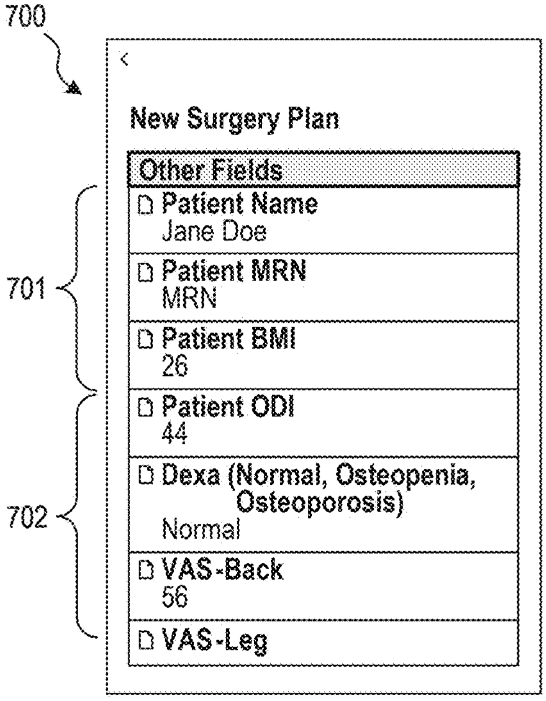
Figure 7C:
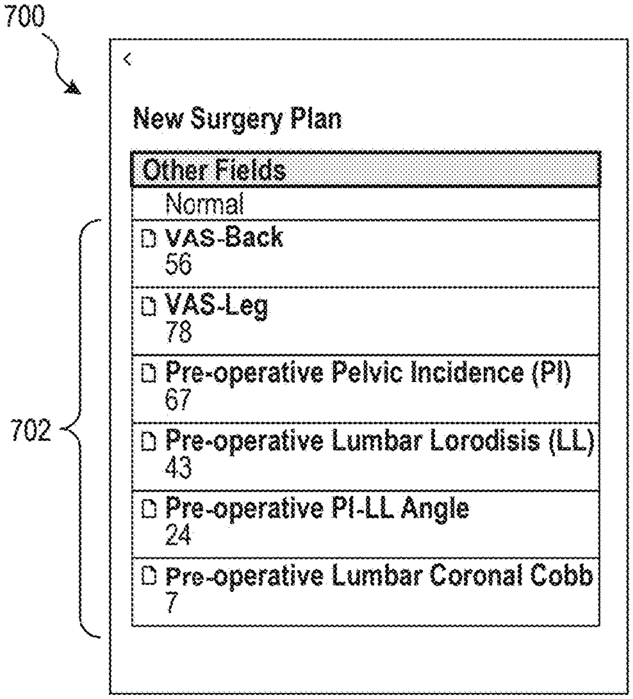
Figure 7D:
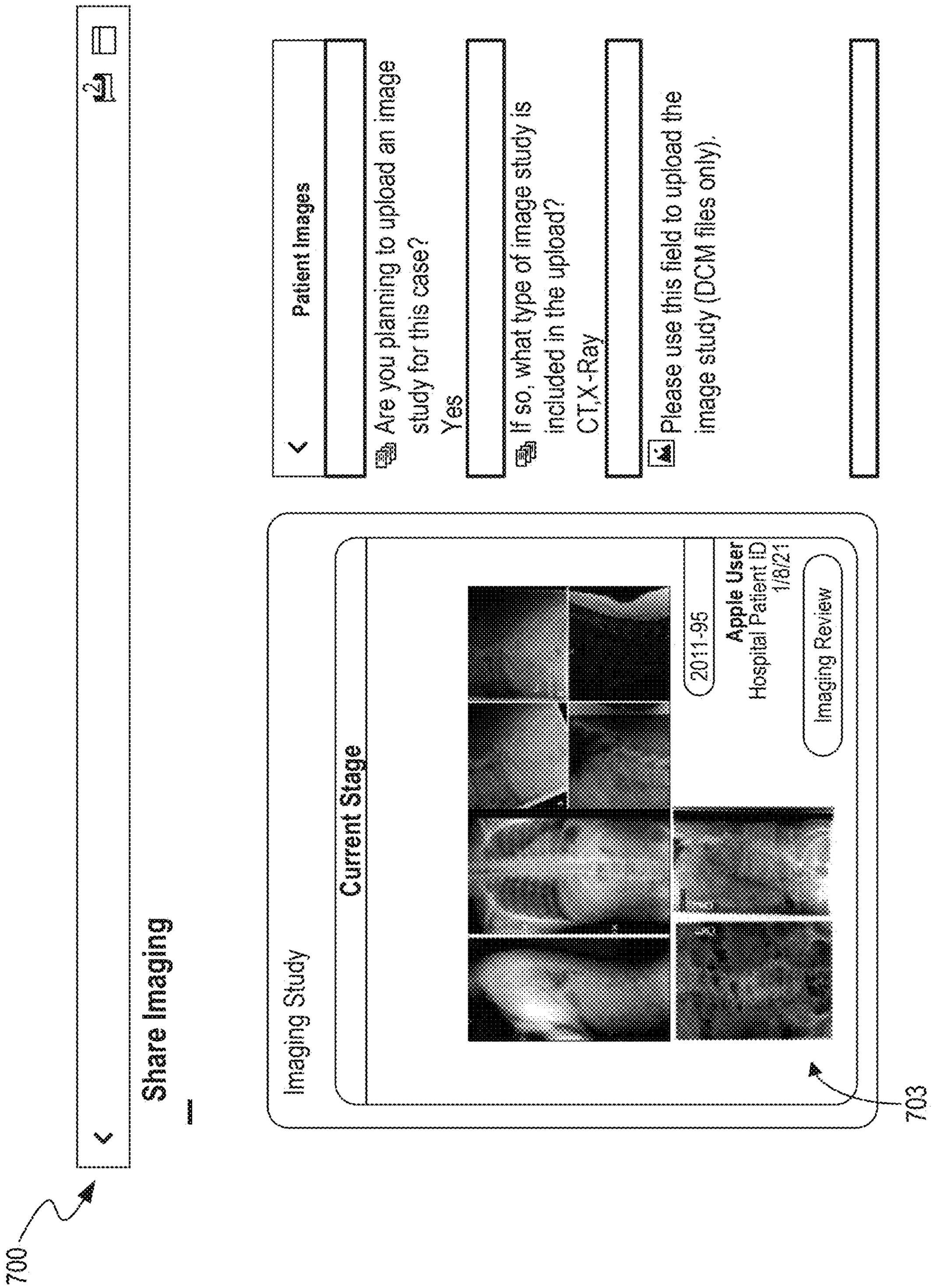

FIG. 6B is a flow diagram illustrating a method 620 for providing confirmation of intra-operative positioning of surgical implants, according to embodiments of the present technology. Steps of the method 620 can be implemented using treatment plans discussed in connection with FIGS. 10A-11. The method 620 can begin in step 622 by obtaining one or more images (e.g., intra-operative images, pre-operative images, etc.) of a patient. The images can include a planned position of an implant in a patient and an actual position of the implant in the placement.

In step 624, the method 620 can calculate measurements of the implant placement in the patient to determine whether the installed implant is at the position (e.g., location, orientation, etc.) that was determined in the pre-operative model (as described in step 503-516 of FIG. 5). The measurements can include coordinates of an implant in the patient's body. For example, the measurements are the distance of the implant from one or more anatomical elements (e.g., bones, organs, joints, etc.), landmarks, reference features (e.g., other implants), or any location on the patient.

In some implementations, the measurements are calculations of the difference (e.g., delta, deviation) between the intra-operative data and the pre-operative plan/model. The measurements can include degrees of rotation that the implant in the patient differs from the pre-operative plan, and/or the metric distance that the implant in the patient needs to move to align with the pre-operative plan. In some implementations, the measurements include a percentage calculation (e.g., 89%, 96%, etc.) that the intra-operative data aligns with the pre-operative plan. Method 620 can calculate a metric for the completion of the installation of the implant in the patient. Based on the severity of the patient's condition, a threshold completion percentage may be adjusted. Method 620 can notify the healthcare provider, when the threshold completion percentage is reached during an installation procedure.

In step 626, the method 620 can display the measurements on a user interface (e.g., display 122 of FIG. 1) for a user (e.g., healthcare provider) to view. Method 620 can display pre-operative and intra-operative metrics (e.g., pre-operative patient metrics or measurements 1002 and intra-operative patient metrics 1004 of FIG. 10A). Method 620 can display a comparison percentage (e.g., illustrated by notification 1022 of FIG. 10B) of the intra-operative data to the pre-operative plan. In some implementations, method 620 displays a metric for the completion (e.g., illustrated by notification 1024 of FIG. 10B) of the installation of the implant in the patient. Method 620 can display a live comparison (e.g., plan 1000 of FIG. 10A, plan 1020 of FIG. 10B, or overlaid image 1060 of FIG. 10D) of the intra-operative data to the pre-operative plan while a healthcare provider is installing an implant in a patient.

In step 628, method 620 can generate a notification of the results of the comparison of pre-operative plan to intra-operative data. Method 620 can notify a healthcare provider if the results differ a threshold amount from the pre-operative model. For example, if the location of the implant in the patient is threshold distance from where the implant located in the surgical plan, a user can receive a notification to adjust the position of the implant before completing the procedure.

Machine learning algorithms can be used to perform one or more steps of method 600 of FIG. 6A and method 620 of FIG. 6B. For example, the SPC platform 109 of FIG. 1 can include a machine learning model trained using the selected reference patient data sets. Patient images can be inputted into the trained machine learning model to provide confirmation of intra-operative positioning of surgical implants based on the pre-operative plan. The machine learning model can be selected based on design goals, such as optimized patient outcomes.

FIGS. 7A-13 further illustrate select aspects of providing patient-specific medical care, e.g., in accordance with the method 500. For example, FIGS. 7A-7D illustrate an example of a patient data set 700 (e.g., as received in step 502 of the method 500). The patient data set 700 can include any of the information previously described with respect to the patient data set. For example, the patient data set 700 includes patient information 701 (e.g., patient identification no., patient medical records, patient name, sex, age, body mass index (BMI), surgery date, surgeon, etc., shown in FIGS. 7A and 7B), diagnostic information 702 (e.g., Oswestry Disability Index (ODI), VAS-back score, VAS-leg score, Pre-operative pelvic incidence, pre-operative lumbar lordosis, pre-operative PI-LL angel, pre-operative lumbar coronal cobb, etc., shown in FIGS. 7B and 7C), and image data 703 (X-ray, CT, MRI, etc., shown in FIG. 7D). In the illustrated embodiment, the patient data set 700 is collected by a healthcare provider (e.g., a surgeon, a nurse, etc.) using a digital and/or fillable report that can be accessed using a computing device. In some embodiments, the patient data set 700 can be automatically or at least partially automatically generated based on digital medical records of the patient. Regardless, once collected, the patient data set 700 can be transmitted to the computing system configured to generate the surgical plan for the patient.

Figure 8A:
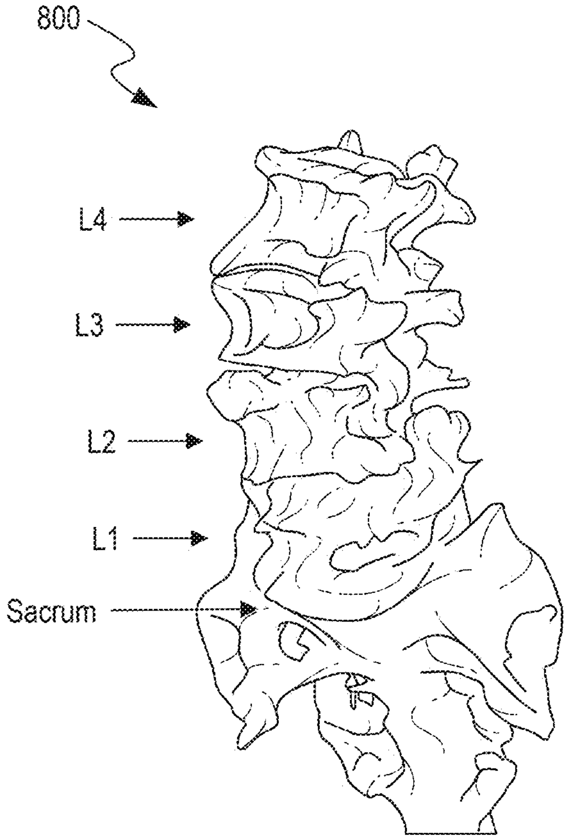
FIGS. 8A and 8B illustrate an exemplary virtual model of a patient's spine that may be used and/or generated in connection with the methods described herein, according to an embodiment.
Figure 8B:
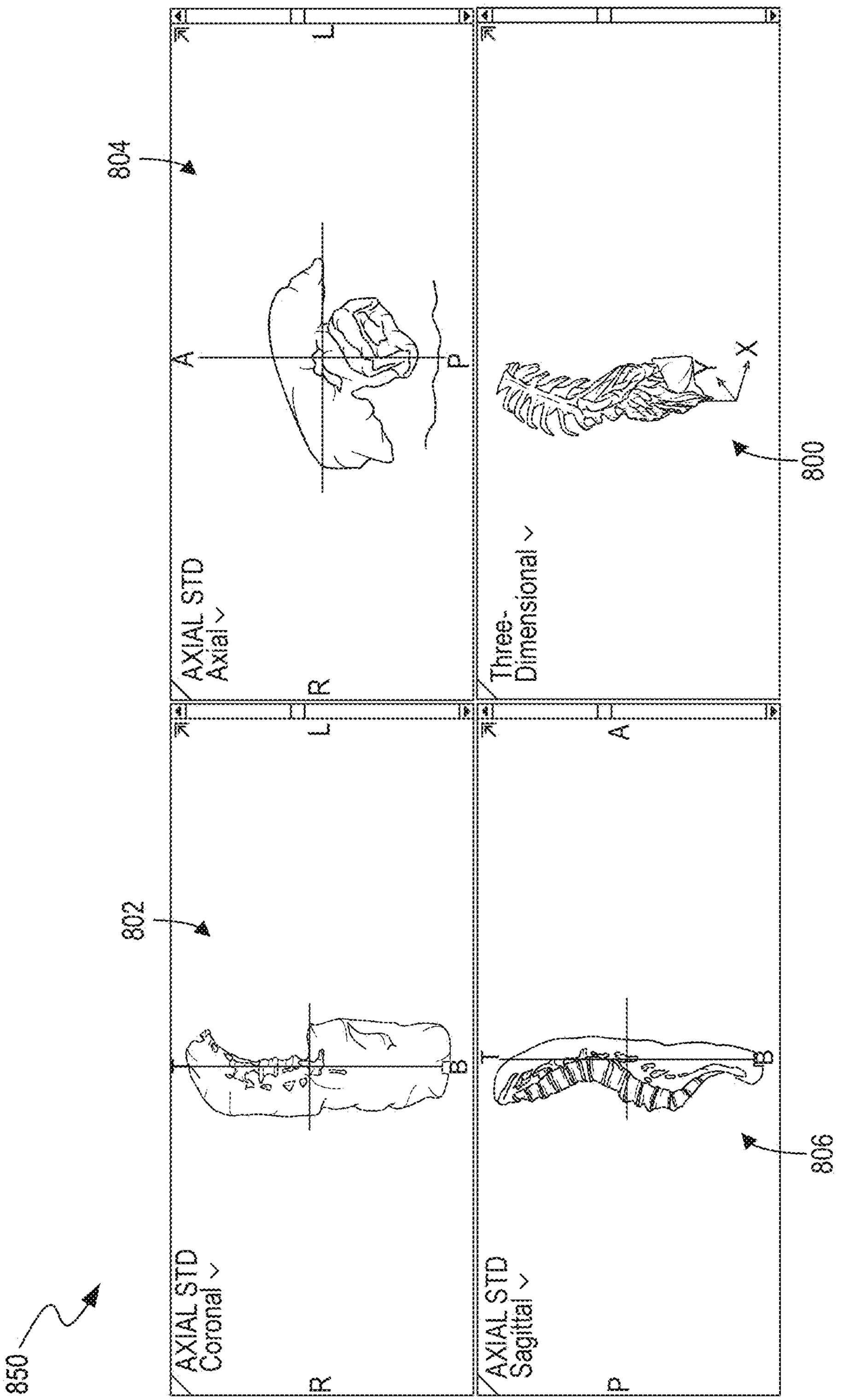

FIGS. 8A and 8B illustrate an example of a virtual model 800 of a patient's native anatomical configuration (e.g., as created in step 503 of the method 500). In particular, FIG. 8A is an enlarged view of the virtual model 800 of the patient's native anatomy and shows the patient's native anatomy of their lower spinal cord region. The virtual model 800 is a three-dimensional visual representation of the patient's native anatomy. In the illustrated embodiment, the virtual model includes a portion of the spinal column extending from the sacrum to the L4 vertebral level. Of course, the virtual model can include other regions of the patient's spinal column, including cervical vertebrae, thoracic vertebrae, lumbar vertebrae, and the sacrum. The illustrated virtual model 800 only includes bony structures of the patient's anatomy, but in other embodiments may include additional structures, such as cartilage, soft tissue, vascular tissue, nervous tissue, etc.

FIG. 8B illustrates a virtual model display 850 (referred to herein as the "display 850") showing different views of the virtual model 800. The virtual model display 850 includes a three-dimensional view of the virtual model 800, one or more coronal cross section(s) 802 of the virtual model 800, one or more axial cross section(s) 804 of the virtual model 800, and/or one or more sagittal cross section(s) 806 of the virtual model 800. Of course, other views are possible and can be included on the virtual model display 850. In some embodiments, the virtual model 800 may be interactive such that a user can manipulate the orientation or view of the virtual model 800 (e.g., rotate), change the depth of the displayed cross-sections, select and isolate specific bony structures, or the like.

Figures 1, 9A:
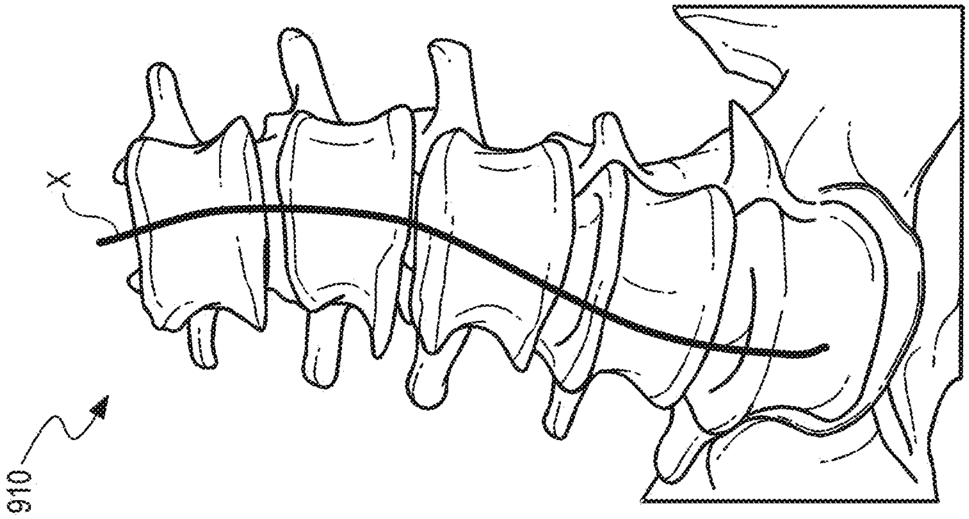
Figures 2, 9A:
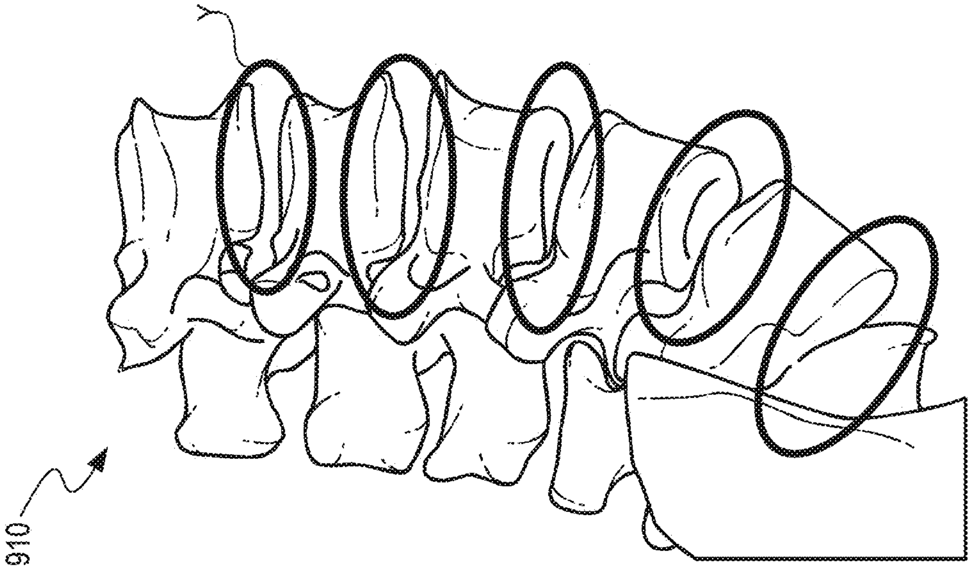
Figures 2, 9B:
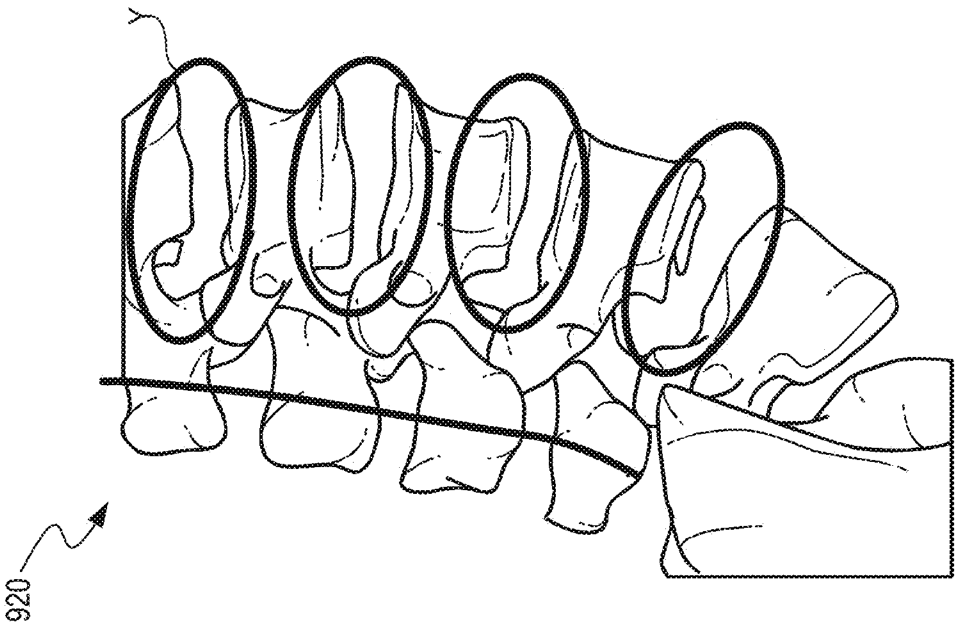
Figures 1, 9B:
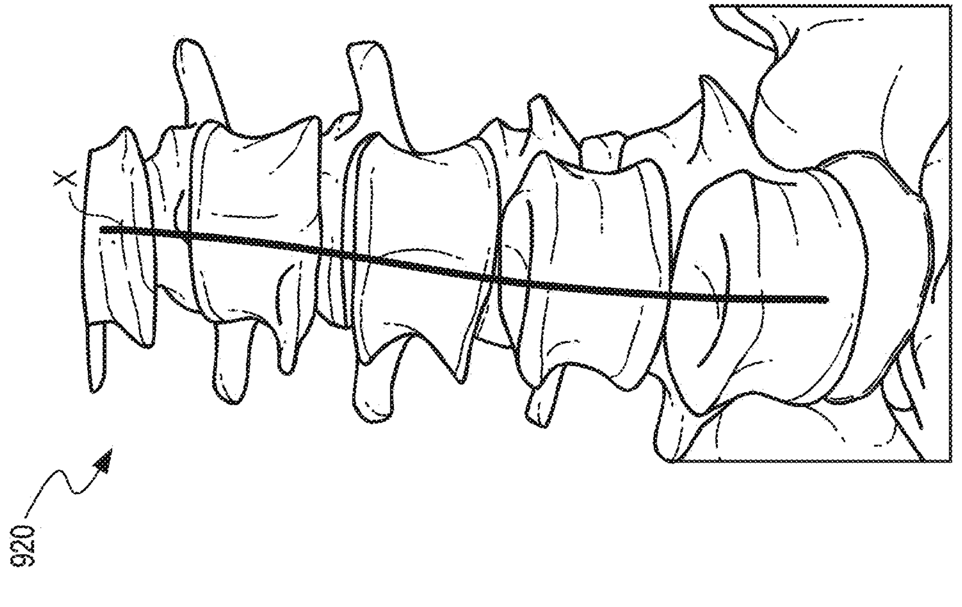

FIGS. 9A-1-9B-2 demonstrate an example of a virtual model of a patient's native anatomical configuration (e.g., as created in step 503 of the method 500) and a virtual model of the patient's corrected anatomical configuration (e.g., as created in step 504 of the method 500). In particular, FIGS. 9A-1 and 9A-2 are anterior and lateral views, respectively, of a virtual model 910 showing a native anatomical configuration of a patient, and FIGS. 9B-1 and 9B-2 are anterior and lateral views, respectively, of a virtual model 920 showing the corrected anatomical configuration for the same patient. Referring first to FIG. 9A-1, the anterior view of the virtual model 910 illustrates the patient has abnormal curvature (e.g., scoliosis) of their spinal column. This is marked by line X, which follows a rostral-caudal axis of the spinal column. Referring next to FIG. 9A-2, the lateral view of the virtual model 910 illustrates the patient has collapsed discs or decreased spacing between adjacent vertebral endplates, marked by ovals Y. FIGS. 9B-1 and 9B-2 illustrate the corrected virtual model 920 accounting for the abnormal anatomical configurations shown in FIGS. 9A-1 and 9A-2. For example, FIG. 9B-1, which is an anterior view of the virtual model 920, illustrates the patient's spinal column having corrected alignment (e.g., the abnormal curvature has been reduced). This correction is shown by line X, which also follows a rostral-caudal axis of the spinal column. FIG. 9B-2, which is a lateral view of the virtual model 920, illustrates the patient's spinal column having restored disc height (e.g., increased spacing between adjacent vertebral endplates), also marked by ovals Y. The lines X and the ovals Y are provided in FIGS. 9A-1-9B-2 to more clearly demonstrate the correction between the virtual models 910 and 920, and are not necessarily included on the virtual models generated in accordance with the present technology.

Figure 10A:
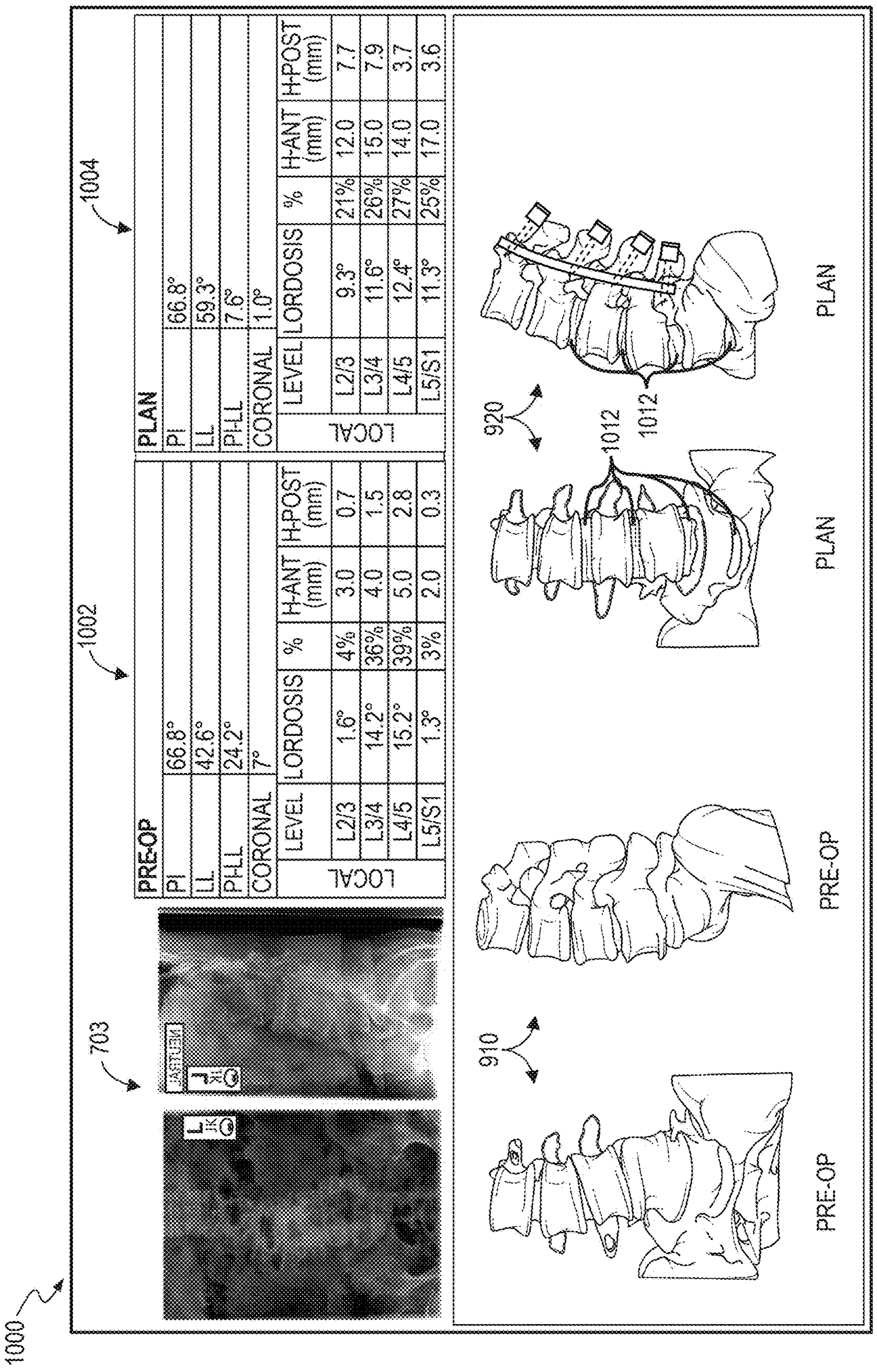
FIG. 10A illustrates an exemplary interactive surgical plan for a patient-specific surgical procedure, according to an embodiment.

FIG. 10A illustrates an example of a surgical plan 1000 (e.g., as generated in step 506 of the method 500, method 600 of FIG. 6A, or method 620 of FIG. 6B). The surgical plan 1000 can include pre-operative patient metrics or measurements 1002, intra-operative patient metrics 1004, one or more patient images (e.g., the patient images 703 received as part of the patient data set), the virtual model 910 (which can be the model itself or one or more images derived from the model) of the patient's native anatomical configuration (e.g., pre-operative patient anatomy), and/or the intra-operative virtual model 920 (which can be the model itself or one or more images derived from the model) of the patient's corrected anatomical configuration (e.g., intra-operative patient anatomy). The pre-operative patient metrics 1002 can include, without limitation, lumbar lordosis, Cobb angle(s), pelvic incidence, disc height, coronal offset distance, segment flexibility, LL-PI is greater than predetermined degrees (e.g., 5 degrees, 10 degrees, etc.), LL-PI mismatch (e.g., age-adjusted), sagittal vertical axis offset distance, coronal offset distance, coronal angle, bone quality, rotational displacement.

The virtual model 920 of the intra-operative patient anatomy can optionally include one or more implants 1012 shown as implanted in the patient's spinal cord region to demonstrate how patient anatomy will look following the surgery. Although four implants 1012 are shown in the virtual model 920, the surgical plan 1000 may include more or fewer implants 1012, including one, two, three, five, six, seven, eight, or more implants 1012.

The surgical plan 1000 can include additional information beyond what is illustrated in FIG. 10. For example, the surgical plan 1000 may include pre-operative instructions, operative instructions, and/or post-operative instructions. Operative instructions can include one or more specific procedures to be performed (e.g., PLIF, ALIF, TLIF, LLIF, DLIF, XLIF, etc.) and/or one or more specific targets of the operation (e.g., fusion of vertebral levels L1-L4, anchoring screw to be inserted in lateral surface of L4, etc.). Although the surgical plan 1000 is demonstrated in FIG. 10A as a visual report, the surgical plan 1000 can also be encoded in computer-executable instructions that, when executed by a processor connected to a computing device, cause the surgical plan 1000 to be displayed by the computing device. In some embodiments, the surgical plan 1000 may also include machine-readable operative instructions for carrying out the surgical plan. For example, the surgical plan can include operative instructions for a robotic surgical platform to carry out one or more steps of the surgical plan 1000.

Figure 10B:
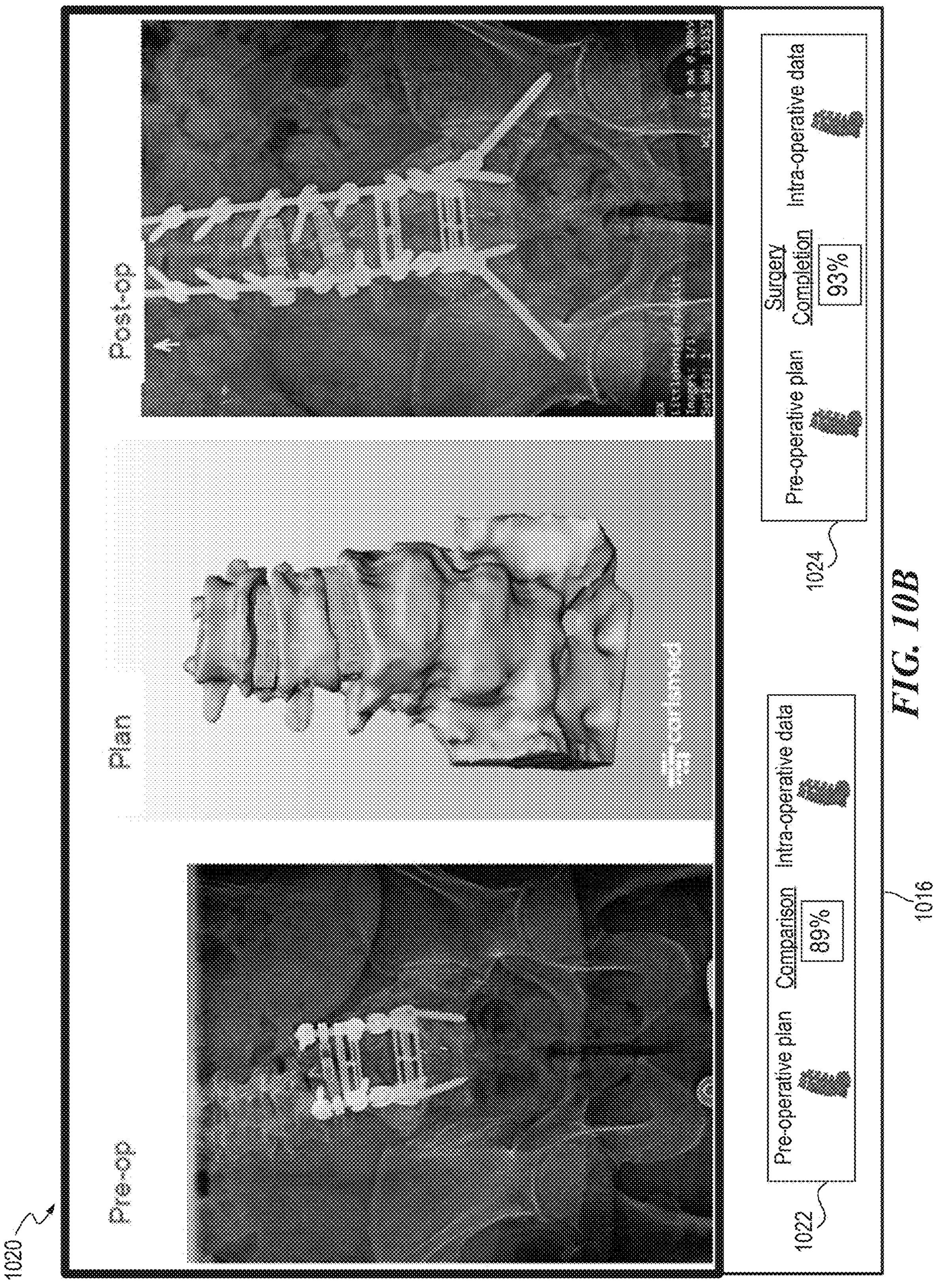
FIG. 10B illustrates pre-operative, plan, intra-operative, and post-operative images to allow for assessment of achievement of surgical goals, according to an embodiment.

FIG. 10B illustrates plan 1020 with a pre-operative imaging, pre-operative plan, intra-operative image, and post-operative image to allow for assessment of achievement of surgical goals, according to an embodiment. Plan 1020 can display a notification 1022 of a comparison percentage (e.g., 89%) of the intra-operative data to the pre-operative plan. Plan 1020 can display notification 1024 which is a metric of completion (e.g., 93%) of the installation of the implant in the patient. The pre-operative plan images can be generated based on one or more pre-operative images, virtual models (e.g., virtual 3D models), and/or other data disclosed herein. The data can be manipulated or modified to, for example, compensate for loading conditions by, for example, repositioning features in the virtual model to match intra-operative loading conditions. The planned image of FIG. 10B shows planned positions for anatomical elements of the patient. The planned image can also include additional features from the pre-operative image, such as the fixation system in the illustrated pre-operative image. The previously implanted fixation system can be used in the landmark for aligning the intra-operative images and the planned images.

Figure 10C:
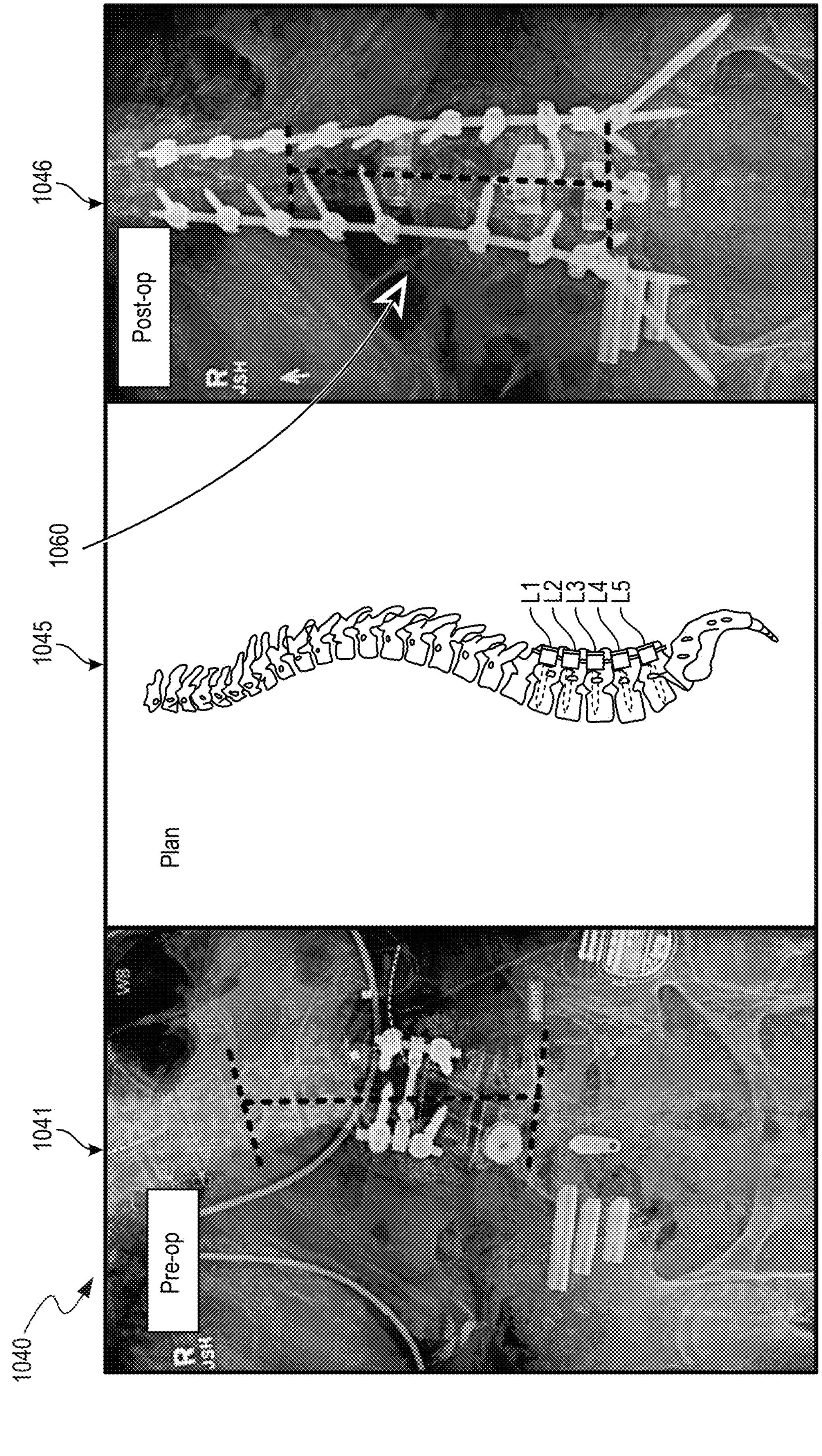
FIG. 10C illustrates pre-operative, plan and post-operative images to allow for assessment of achievement of surgical goals, according to an embodiment.

FIG. 10C illustrates a plan 1040 with images for assessment of achievement of surgical goals, according to an embodiment. Plan 1040 can include a pre-operative image 1041 showing a prior fixation system in a patient (e.g., a fixation system to be removed), a plan image 1045 showing a patient-specific posterior fixation system implanted along L1-L5, and a post-operative image 1046 showing post-operative anatomy of the patient after implanting a posterior fixation system with additional levels. A user can compare the pre-operative, plan, and post-operative images to evaluate effectiveness of the treatment. The images can be used to train, or retrain, a machine learning module configured to design multi-component implant systems, such as the implants and patient-specific posterior fixation system discussed in connection with FIGS. 11-30.

Figure 11:
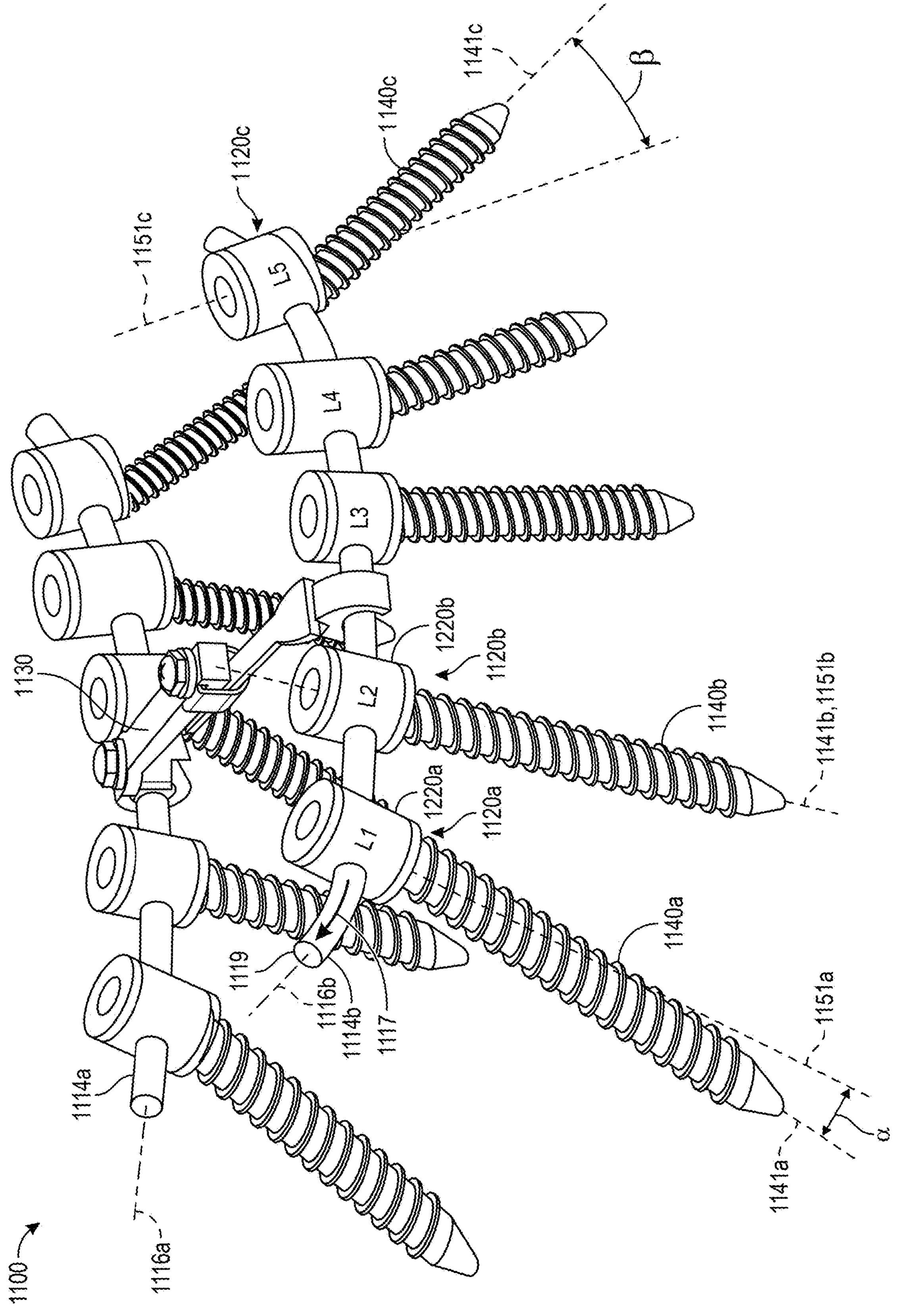
FIG. 11 illustrates a patient-specific posterior fixation system, according to at least some embodiments.

FIG. 11 illustrates a patient-specific posterior fixation system 1100, according to at least some embodiments. The posterior fixation system 1100 includes rods 1114*a*-*b* (collectively, "rods 1114") and anchor assemblies (three identified as anchor assemblies 1120*a*, 1120*b*, 1120*c* or, collectively, "anchor assemblies 1120"). One or more rod connectors 1130 can couple together the rods 1114. The components and features of the posterior fixation system 1100 can be designed to fit together to enhance rigidity, improve fatigue life, limit inadvertent movement between components, improve positioning, etc. One, some, or all of the rods 1114 and/or anchor assemblies 1120 can be patient-specific for flexible customized treatments.

The rods 1114 can be configured to achieve a target anatomical configuration of the patient while the anchor assemblies 1120 can be configured to achieve desired anchoring to vertebrae. The components of the posterior fixation system 1100 can be labeled for assisting with positioning. The rod 1114*b* can include an orientation indicator (e.g., arrow 1117) indicating a superior end 1119 of the rod. The rod 1114*b* can also include, for example, markers indicating vertebral levels, implant holder positions, or the like. The anchor assemblies 1120 can have indicia (e.g., labels L1-L5) indicating implantation levels.

The rods 1114 can be patient-specific rods designed to position vertebrae at target locations, spatial relationships, etc., thereby achieving a target configuration of the patient. For example, the rod 1114*a* can have a curved axis 1116*a* matching a target axis/curvature along a first side of the patient's spine. The rod 1114*b* can have an axis 1116*b* matching a target axis/curvature along a second side of the patient's spine. For example, the rod 1114*a* can be positioned along right sides of L1-L5 vertebral bodies and the rod 1114*b* can be positioned along left sides of the L1-L5 vertebral bodies.

The anchor assemblies 1120 can be patient-specific anchor assemblies designed based on the curvature of the rods. Each anchor assembly can be designed for a specific implant location, resulting in non-uniform or non-geometrically congruent anchor assemblies. For example, the anchor assembly 1120*a* can include a bone anchor 1140*a* with a longitudinal axis 1141*a* positioned to pass through a vertebral body when implanted. An angle $\alpha$ (e.g., 10 degrees, 20 degrees, 30 degrees, etc.) can be defined by the longitudinal axis 1141*a* of the bone anchor 1140*a* and a longitudinal axis 1151*a* of a rod holder or couple 1220*a* ("rod holder 1220*a*"). The anchor assembly 1120*b* can have a bone anchor 1140*b* with a longitudinal axis 1141*b* generally aligned with or parallel to a longitudinal axis 1151*b* of a rod holder or couple 1220*b* ("rod holder 1220*b*"). The anchor assembly 1120*c* can include a bone anchor 1140*c* that is offset from a rod holder 1220*c*. An angle β (e.g., 30 degrees, 40 degrees, 50 degrees, etc.) can be defined by the longitudinal axis 1141*c* of the bone anchor 1140*c* and a longitudinal axis 1151*c* of the rod holder or couple 1220*c* ("rod holder 1120*c*"). The angles α and β can be different from one another so that the bone anchors 1140*a*, 1140*c* can be inserted into vertebral bodies at patient-specific trajectories selected based on, for example, the size and configuration of vertebral bodies, patient's biomechanics, etc.

Figure 12:
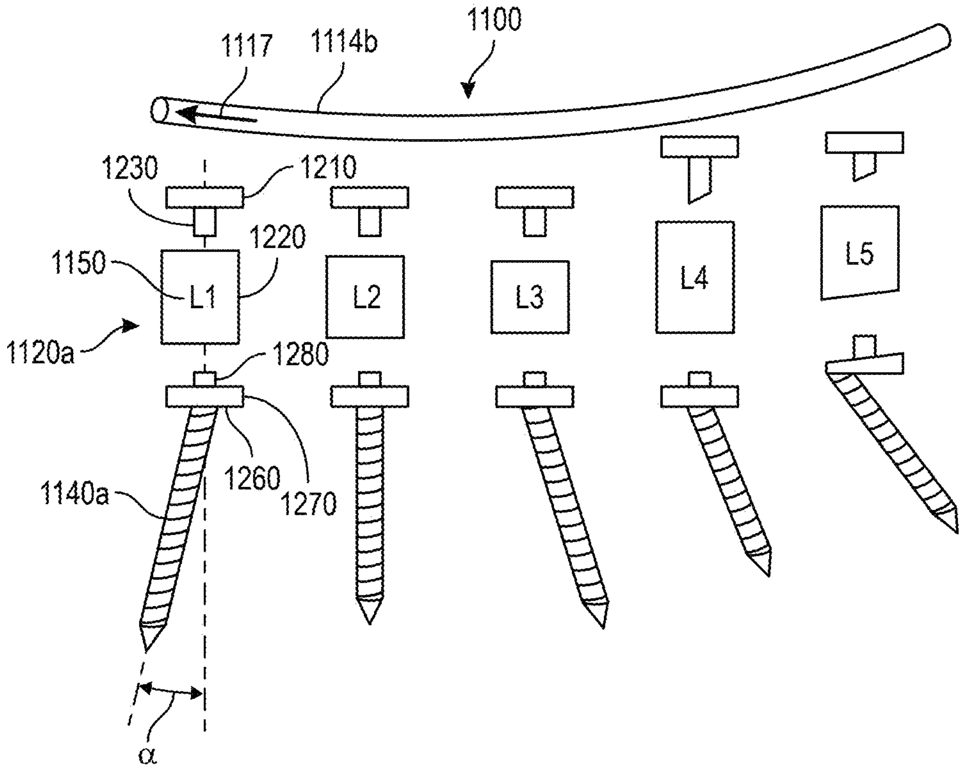
FIG. 12 is a plan view of components of a patient-specific posterior fixation system, according to at least some embodiments.
Figure 13:
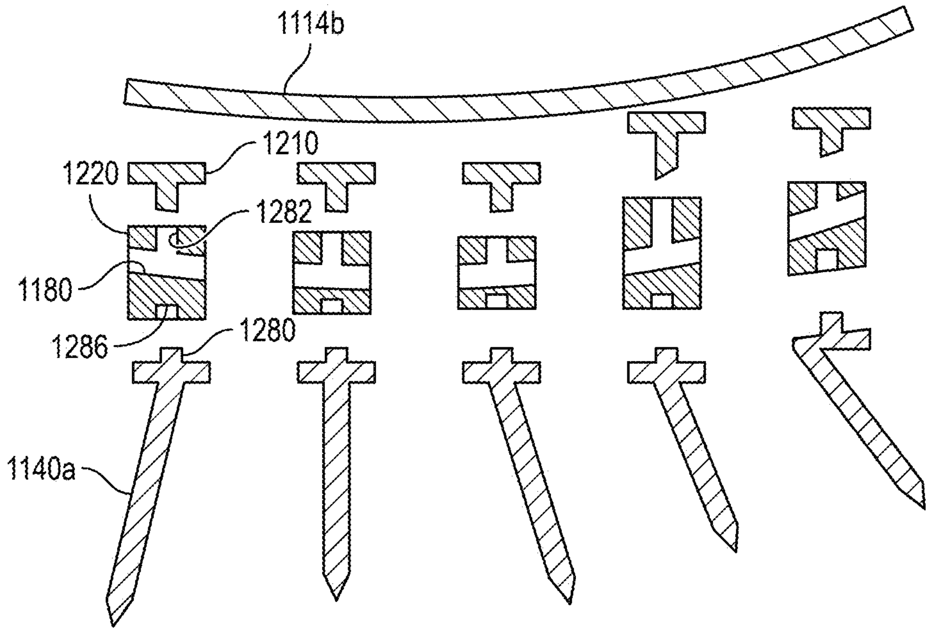
FIG. 13 is a cross-sectional plan view of the components of FIG. 12.

FIG. 12 is a plan view of components of the patient-specific posterior fixation system 1100, according to at least some embodiments. FIG. 13 is a cross-sectional plan view of the components of FIG. 12. The patient-specific posterior fixation system 1100 can include a combination of features or components discussed in connection with FIGS. 14-29 and/or standard or off-the-shelf components. The description of one component applies equally to other similar components unless indicated otherwise.

Referring now to FIG. 12, the anchor assembly 1120*a* can include a rod retainer 1210, a rod couple or holder 1220 with a label 1150, and the bone anchor 1140*a*. The rod retainer 1210 can have an abutment or protrusion 1230 configured to press against the rod 1114*b*. The rod holder 1220 has an internal passageway matching a corresponding portion of the rod 1114*b*. Some or all of the rod holders 1220 (one identified) can have different configurations configured to match configurations of other components, such as the rod 1114*b*. For example, each rod holder 1220 can have a rod passageway configured to match a corresponding portion of the rod 1114*b* that it is designed to hold. The bone anchor 1140*a* can include a seating member 1260 with a face plate 1270 and a mating feature 1280.

Referring now to FIG. 13, the rod 1114*b* can be inserted along a passageway 1180 of the rod holder 1220. A rod retainer 1210 can be inserted through a side passageway 1282 until it presses against a side of the rod 1114*b*. The mating feature 1280 can be inserted into a receiving opening 1286 to automatically lock together the rod holder 1220 and the bone anchor 1140*a*.

Figure 14:
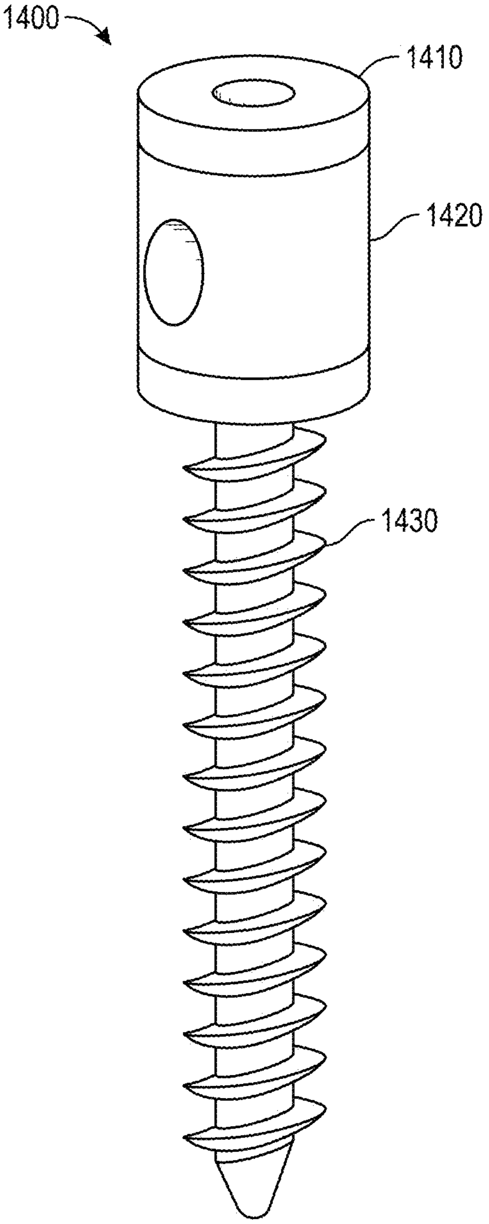
FIG. 14 is an isometric view of an anchor assembly, according to at least some embodiments.
Figure 15:
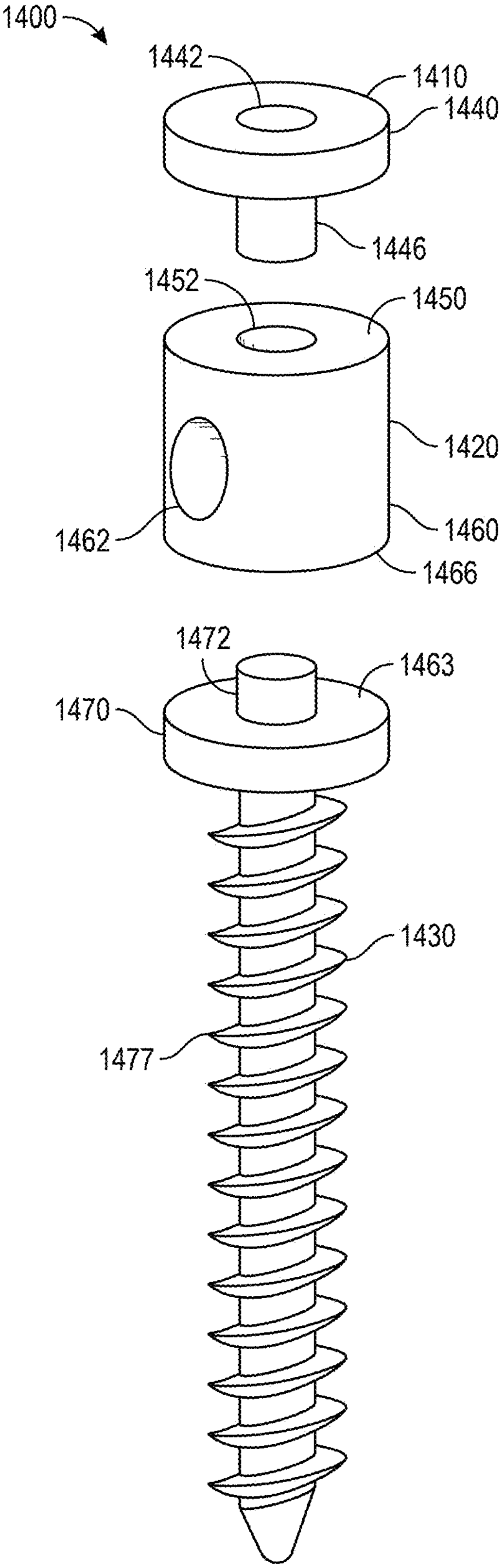
FIG. 15 is an exploded isometric view of the anchor assembly of FIG. 14.

FIG. 14 is an isometric view of an anchor assembly 1400, according to at least some embodiments. FIG. 15 is an exploded isometric view of the anchor assembly of FIG. 14. Referring now to FIG. 14, the anchor assembly 1400 includes a locking member 1410, a rod couple 1420, and an anchor 1430. Referring now to FIG. 15, the locking member 1410 includes a cap 1440, a drive feature 1442, and an contact feature 1446. The cap 1440 can be configured to rest against a face 1450 of the rod couple 1420 or against a rod contained within cavity 1462. The drive feature 1442 can be configured to receive a torquing instrument. The contact feature 1446 can be configured to fit within a receiving opening 1452 of the rod couple 1420. In some embodiments, the contact feature 1446 can be externally threaded to mate with internal threads of the receiving opening 1452. For example, the locking member 1410 can be rotated clockwise via an instrument positioned in the drive feature 1442 to drive the contact feature 1446 downwardly along a passageway 1462.

The rod couple 1420 can have a cylindrical body 1460 and a rod-receiving passageway 1462. A lower face 1466 can be configured to mate with an upper surface 1463 of the anchor 1430. The passageway 1462 can be configured to receive the spinal rod.

The anchor 1430 can include a mating component 1470 including a mating feature 1472 configured to be received by the rod couple 1420. The mating feature 1472 can be externally threaded, include one or more barbs, or include one or more other retaining features. In some embodiments, the anchor 1430 is automatically locked to the rod couple 1420 when the mating feature 1472 is inserted into the rod couple 1420. The anchor 1430 can include an externally threaded member 1477 configured to fit within bony tissue. For example, the threaded member 1477 can be configured to be advanced into a vertebral body without compromising the structural integrity of the vertebral body.

Figure 16:
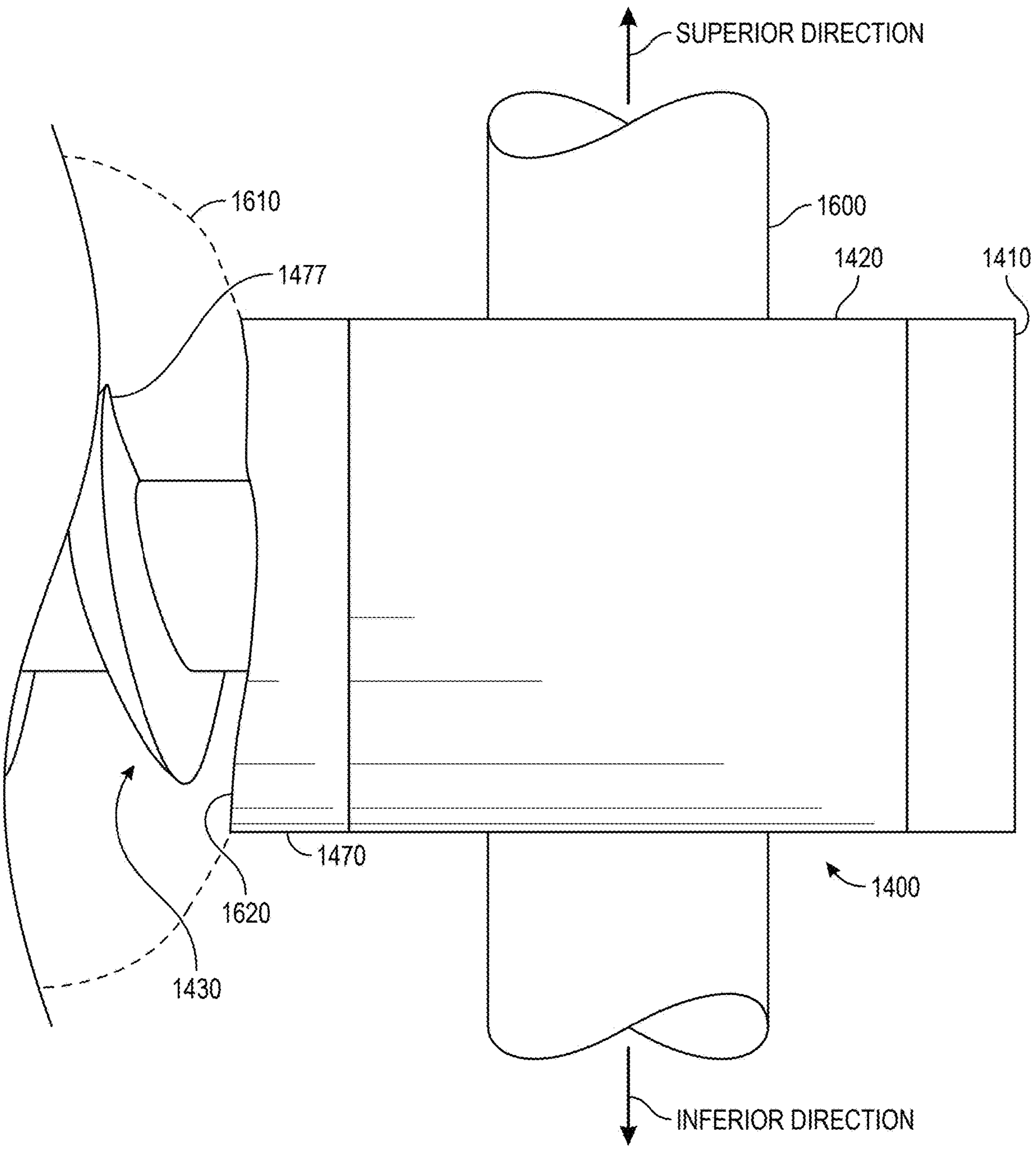
FIG. 16 is a side view of a portion of a patient-specific posterior fixation system connected to tissue, according to at least some embodiments.
Figure 17:
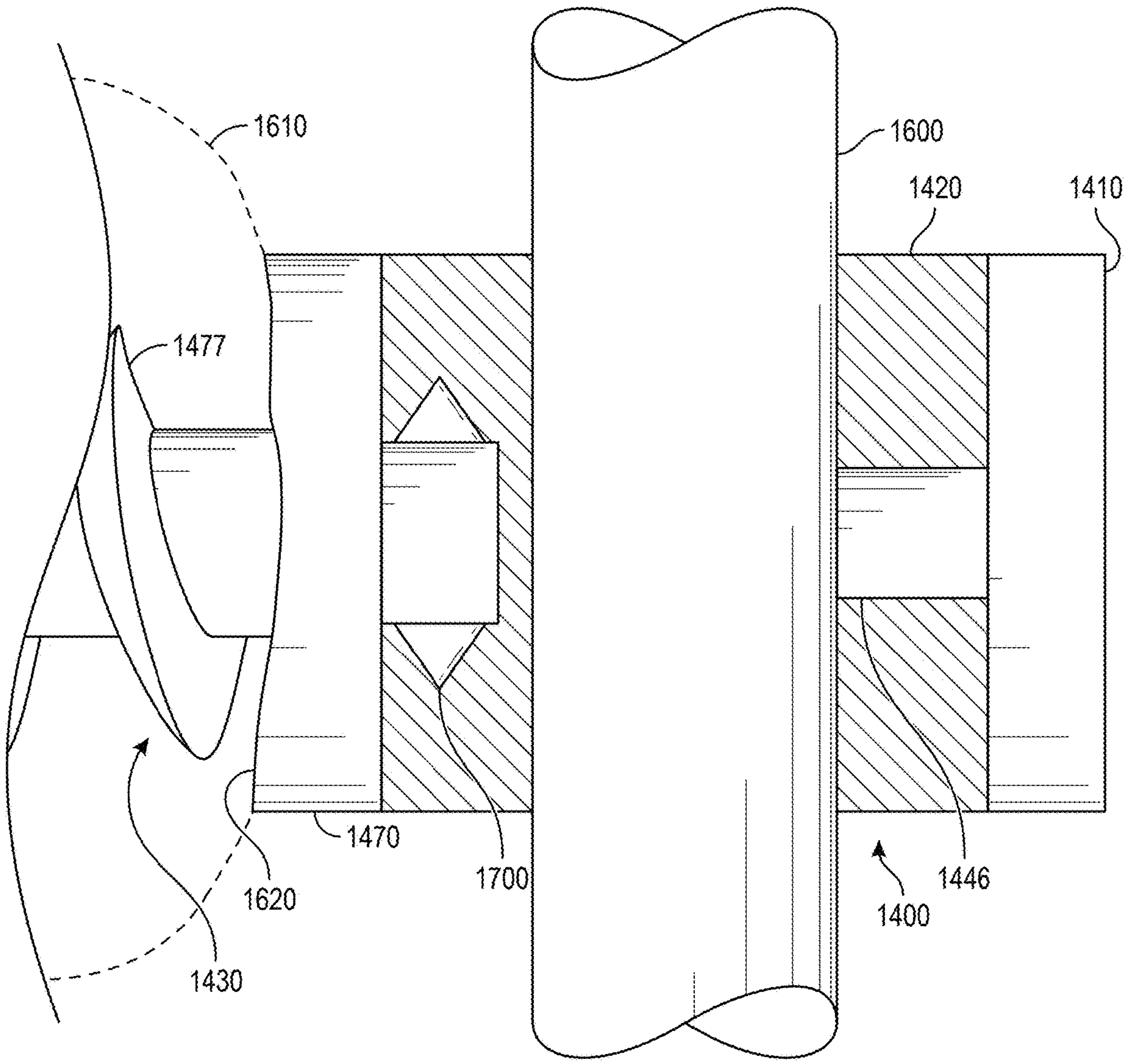
FIG. 17 is a partial cross-sectional side view of a portion of the patient-specific posterior fixation system of FIG. 16, according to at least some embodiments.

FIG. 16 is a side view of a portion of a patient-specific posterior fixation system connected to tissue, according to at least some embodiments. FIG. 17 is a partial cross-sectional side view of an anchor assembly 1400 of FIG. 16. Referring now to FIGS. 16 and 17, the rod couple 1420 holds the spinal rod 1600 and is coupled to the anchor 1430. When the threaded member 1477 is advanced into tissue (e.g., a vertebral body 1610), the surface 1620 can be pulled against the bony tissue. The threaded member 1477 extends into the vertebral body 1610 to hold the mating plate 1470 against the vertebral body 1610. For example, the surface 1620 can lay flush along the vertebral body 1610. The mating plate 1470 can include a patient-specific surface 1620 contoured to match the contour of the vertebral body 1610. For example, the surface 1620 can have undulations, convex sections, concave sections, and undulated surfaces designed for a gapless interface between the surface 1620 and vertebral body 1610. This helps stabilize the rod 1600 and distribute forces to a large area of the bony tissue.

Referring now to FIG. 17, the anchor 1430 can have one or more retention features 1700 that automatically lock the anchor 1430 to the rod couple 1420 (shown in cross section). The retention features 1700 can be one or more fixed or deployable barbs, pins, latching members, or the like. The locking member 1410 includes the contact feature 1446 with an end portion that presses against a side of the rod 1600.

To implant the anchor assembly 1400, the anchor 1430 can be driven into bony tissue by rotating the threaded member 1477 clockwise. An inserter tool can be used to rotate the anchor 1430 until the surface 1620 rests against the bony tissue. The rod couple 1420 can be coupled to the anchor 1430 by inserting the mating plate 1470 (FIG. 15) into the anchor body. The rod 1600 can be inserted through the passageway 1462 (FIG. 15) of the rod couple 1420. The locking member 1410 can be coupled to the rod couple 1420 and holds the rod 1600 stationary relative to the rod couple 1420.

Figure 18:
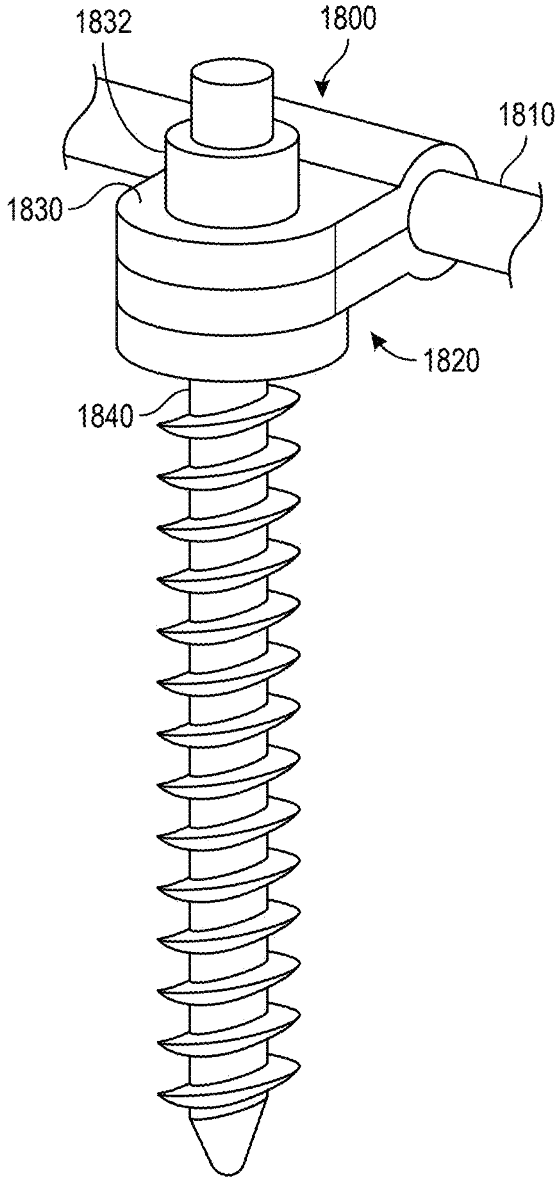
FIG. 18 is an isometric view of an anchor assembly holding a rod, according to at least some embodiments.
Figure 19:
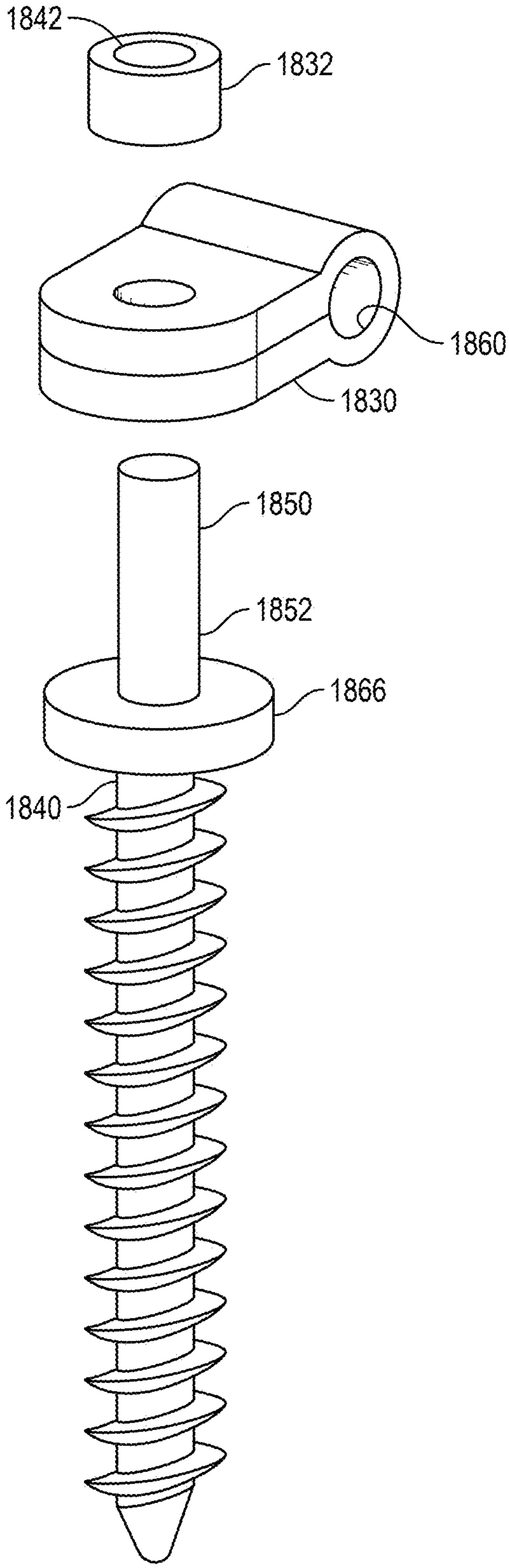
FIG. 19 is an exploded isometric view of the anchor assembly of FIG. 18.

FIG. 18 is an isometric view of a posterior fixation system 1800 including a rod 1810 and an anchor assembly 1820, according to at least some embodiments. FIG. 19 is an exploded isometric view of the posterior fixation system 1800. The descriptions of the rods 1114 and 1600 of FIGS. 11-17 apply equally to the rod 1810.

Referring now to FIG. 18, the anchor assembly 1820 can include a rod holder 1830, a locking member 1832, and an anchor 1840. Referring now to FIGS. 18 and 19, the locking member 1832 can be a cylindrical member having an internally threaded surface 1842 configured to threadably engage an exterior surface 1850 of the anchor 1840. The rod holder 1830 can be configured to be positioned along a post 1852 of the anchor 1840 and includes a rod-receiving passageway 1860. The rod-receiving passageway 1860 can be configured to receive a section of the rod 1810. Example passageways are discussed in connection with FIGS. 23, 24A, and 24B.

Figure 20:
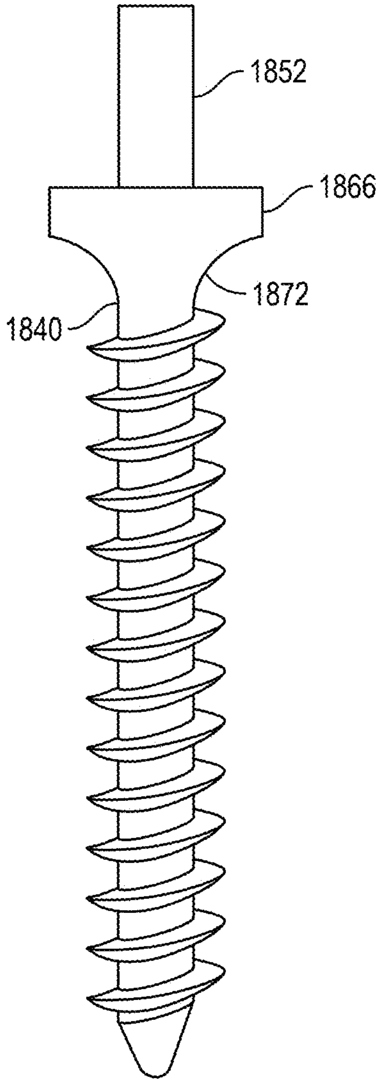
FIG. 20 is a side view of a bone anchor, according to at least some embodiments.

FIG. 20 is a side view of the anchor 1840, in accordance with at least some embodiments. The post 1852 can be configured to hold the rod holder 1830 in a desired position relative to bony anatomy. In some embodiments, the post 1852 is offset, curved, or at other configurations. The plate 1866 (FIGS. 19 and 20) can have a contoured surface 1872 configured to mate with bony tissue. In some embodiments, the surface 1872 is curved, angular, or contoured to match an exterior surface of bony tissue.

Figure 21:
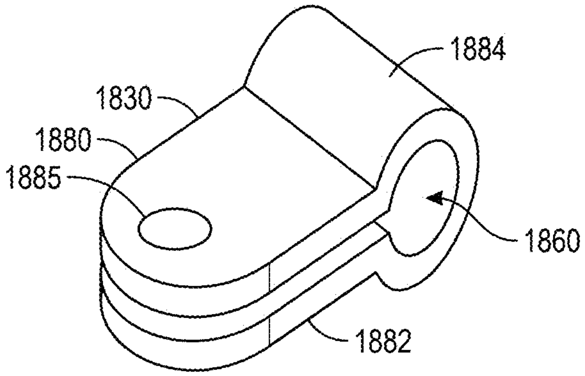
FIG. 21 is an isometric view of a rod couple, according to at least some embodiments.
Figure 22:
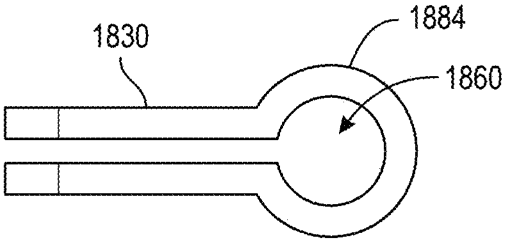
FIG. 22 is a side view of the rod couple of FIG. 21.

FIG. 21 is an isometric view of the rod holder 1830. FIG. 22 is a side view of the rod holder 1830. Referring now to FIG. 21, the rod holder 1830 includes a pair of plates 1880, 1882, each including an opening 1885 configured to receive the post 1852 (FIG. 19). The rod-receiving passageway 1860 can be defined by a tubular region 1884 connected to the plates 1880, 1882. When the plates 1880, 1882 are pressed together, the tubular region 1884 can clamp and securely hold the spinal rod.

Figure 23:
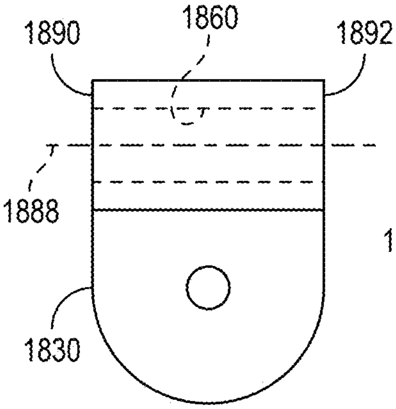
FIG. 23 is a plan view of the rod couple of FIG. 21.

FIG. 23 is a top plan view of the rod holder 1830. The rod-receiving passageway 1860 can have a longitudinal axis 1888 generally perpendicular to end faces 1890, 1892 of the tubular region 1884 (FIG. 21). Referring to FIGS. 18-23, to assemble the posterior fixation system 1800, the anchor 1840 can be advanced into bony tissue. The rod holder 1830 can be moved over to the post 1852. A rod can be installed in the rod-receiving passageway 1860. A locking member 1832 can be coupled to the post 1852 to hold the rod holder 1830 against the plate 1866.

Figure 24A:
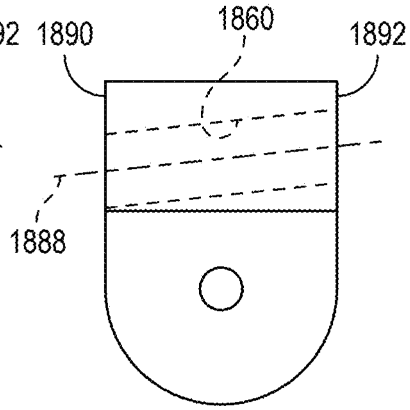
FIGS. 24A and 24B are plan views of rod couples, according to at least some embodiments.
Figure 24B:
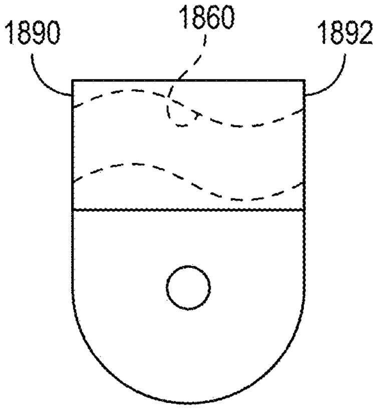

In some embodiments, the longitudinal axis 1888 of the rod-receiving passageway 1860 of FIGS. 24A and 24B can be at a non-perpendicular orientation with respect to one or both of the end faces 1890, 1892. FIG. 24B shows a curved or undulated rod-receiving passageway 1860. The length, configuration, and dimensions of the rod-receiving passageway 1860 can be selected based on the configuration of the spinal rod. For example, the curvature, orientation, and dimensions of the rod-receiving passageway 1860 can be generally similar to or slightly larger than the rod.

Figure 25:
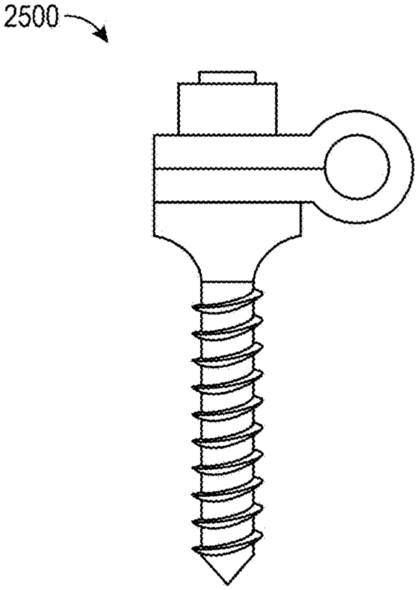
FIG. 25 is a side view of an anchor assembly, according to at least some embodiments.
Figure 26:
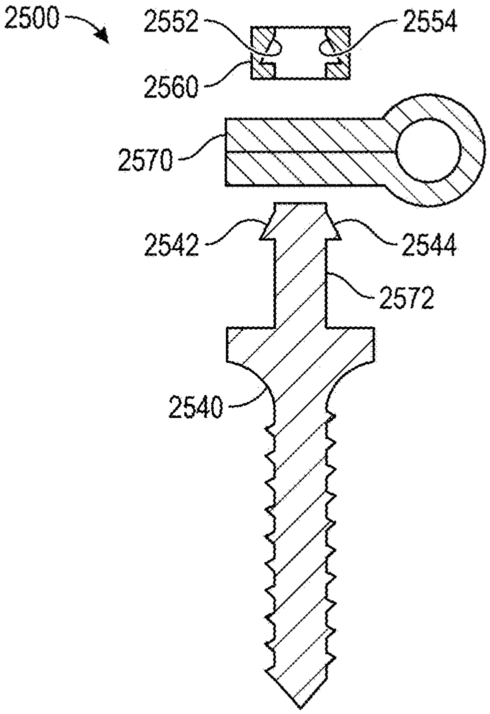
FIG. 26 is an exploded cross-sectional side view of the anchor assembly of FIG. 25.

FIG. 25 is a side view of an anchor assembly 2500, in accordance with at least some embodiments of the technology. FIG. 26 is an exploded side view of the anchor assembly 2500. The descriptions of the anchor assemblies discussed in connection with FIGS. 11-24 apply equally to the anchor assembly 2500 unless indicated otherwise.

Referring now to FIG. 26, the anchor assembly 2500 includes a bone anchor 2540 with barbs 2542, 2544 configured to be positioned within barb receiving features 2552, 2554 of a locking member 2560. The anchor assembly 2500 includes components that are configured to automatically lock together. To assemble the anchor assembly 2500, a rod holder 2570 can be slid along a post 2572 of the bone anchor 2540. The barbs 2542, 2544 can be moved past the plates of the rod holder 2570. The locking member 2560 can be slid along the post 2572 until the barbs 2542, 2544 are received by the barb receiving features 2552, 2554, respectively. In some embodiments, the barbs 2542, 2544 are integrally formed with the post 2572 and can be formed of a compressible material, incompressible material, metal, plastic, or the like. In some embodiments, the barbs 2542, 2544 are deployable. For example, biasing members can bias the barbs 2542, 2544 outwardly. The features, number of barbs, and operation of the barbs can be selected based on the implantation techniques to be used.

Figure 27:
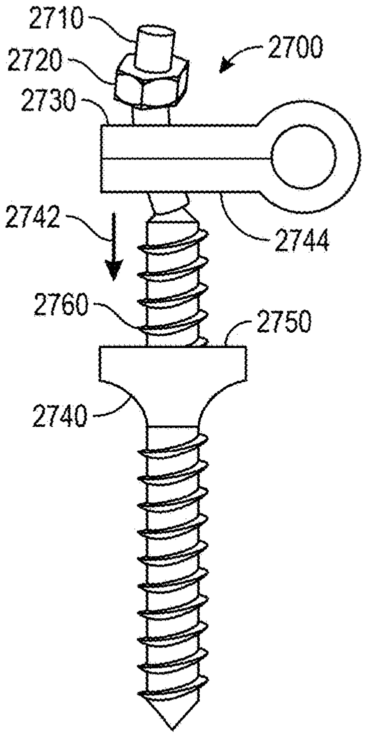
FIG. 27 is a side view of an anchor assembly in an unlocked configuration, according to at least some embodiments.

FIG. 27 is a side view of an anchor assembly 2700 in an unlocked configuration, according to at least some embodiments. The anchor assembly 2700 includes a breakaway tether 2710 carrying a locking member 2720. The anchor assembly 2700 can include a rod holder 2730 and an anchor 2740. To implant the anchor 2740, the rod holder 2730 can be moved distally, as indicated by arrow 2742, until a lower plate 2744 of the rod holder 2730 rests against an anchor face 2750. The locking member 2720 can be advanced distally along the tether 2710 and threadably coupled to the threaded post 2760 of the anchor 2740.

Figure 28:
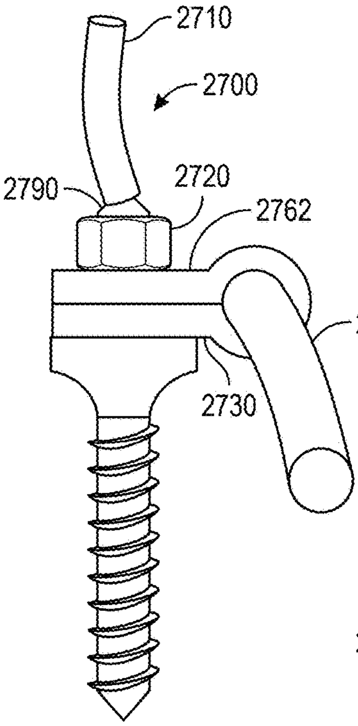
FIG. 28 is a side view of the anchor assembly of FIG. 27 in a locked configuration.
Figure 29:
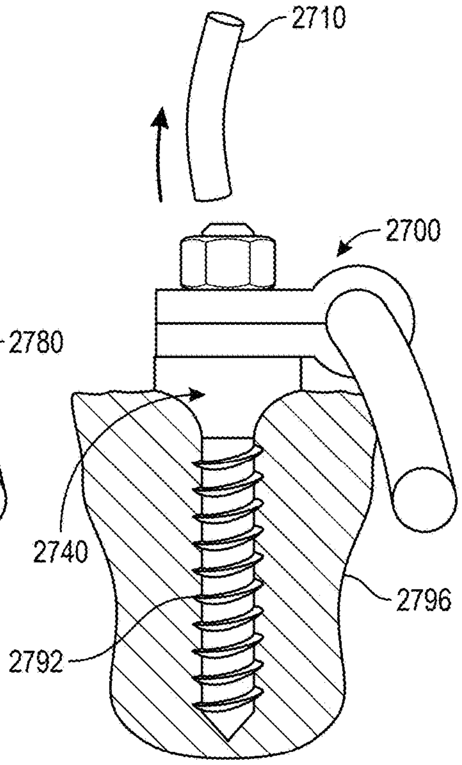
FIG. 29 is a side view of the anchor assembly of FIG. 27 connected to a tissue, according to at least some embodiments.

FIG. 28 is a side view of the anchor assembly 2700 of FIG. 27 in a locked configuration. The locking member 2720 can be positioned against an upper plate 2762 of the rod holder 2730. A spinal rod 2780 can be held by the rod holder 2730. The tether 2710 can include one or more frangible portions 2790 that allow the tether 2710 to be separated from the threaded post 2760, as shown in FIG. 29. The frangible portion 2790 can be a preferentially weakened portion, a circumferential notch, or other feature that allows the tether 2710 to be broken away from the threaded post 2760. FIG. 29 shows the threaded member 2792 of the anchor 2740 positioned within bony tissue 2796.

Figure 30:
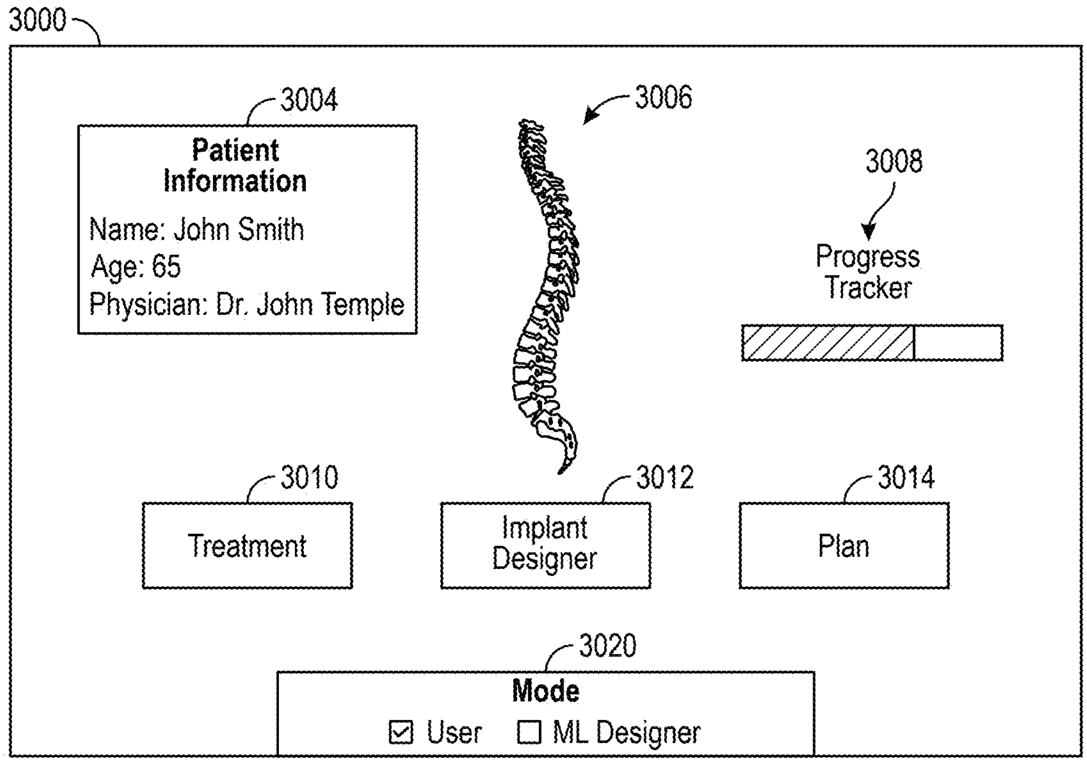
FIG. 30 illustrates a user interface of a surgery manager system for managing treatments, implant designs, and plans, according to at least some embodiments.

FIG. 30 is a surgery manager system user interface 3000 for selecting treatments, designing implants, or managing plans, according to at least some embodiments. The user interface 3000 can show a planned corrected anatomy of the patient. The user interface 3000 can include a patient information window 3004 with patient information. The patient information can include, without limitation, the patient's biometrics, age, health status, electronic medical records, physician information, or other information disclosed herein. A user can select information to be displayed in the patient information window 3004 to assist with treatment planning.

The user interface 3000 can include viewable anatomy information 3006. The anatomy information 3006 can include, without limitation, an image of patient anatomy (e.g., pre-operative anatomy, planned anatomy, post-operative anatomy, etc.), patient images, virtual models (e.g., virtual models of anatomy), or the like. A user can select the anatomy information to be displayed.

The user interface 3000 can include a progress tracker 3008 indicating progress of treatment planning, implant design, treatment plan generation, or the like. In some embodiments, the progress tracker 3008 indicates a percentage completion of treatment planning and approval. This can help a physician when scheduling a surgical procedure.

The user interface 3000 can include a treatment selector 3010 for selecting a candidate treatment as discussed in connection with FIG. 31, an implant designer selector 3012 for launching an implant designer platform as discussed in connection with FIGS. 32-36, and a plan selector 3014 for selecting a treatment plan as discussed in connection with FIGS. 10A-10C.

The user interface 3000 can include a mode selector 3020 for selecting a design mode. In some embodiments, a design platform includes a user design mode and a machine learning (ML) designer mode. A user can select a user design mode (illustrated as selected in FIG. 30) to allow a user to input values for designing implants, generating surgical plans, or the like. The ML designer mode can be selected to have the system design platform use one or more machine learning modules to generate at least a portion of the treatment. For example, a user can generate an initial design using the ML design designer. A user can select a user mode for modifying the initial design. The ML designer can be selected again to generate predicted outcomes of the modified design.

Figure 31:
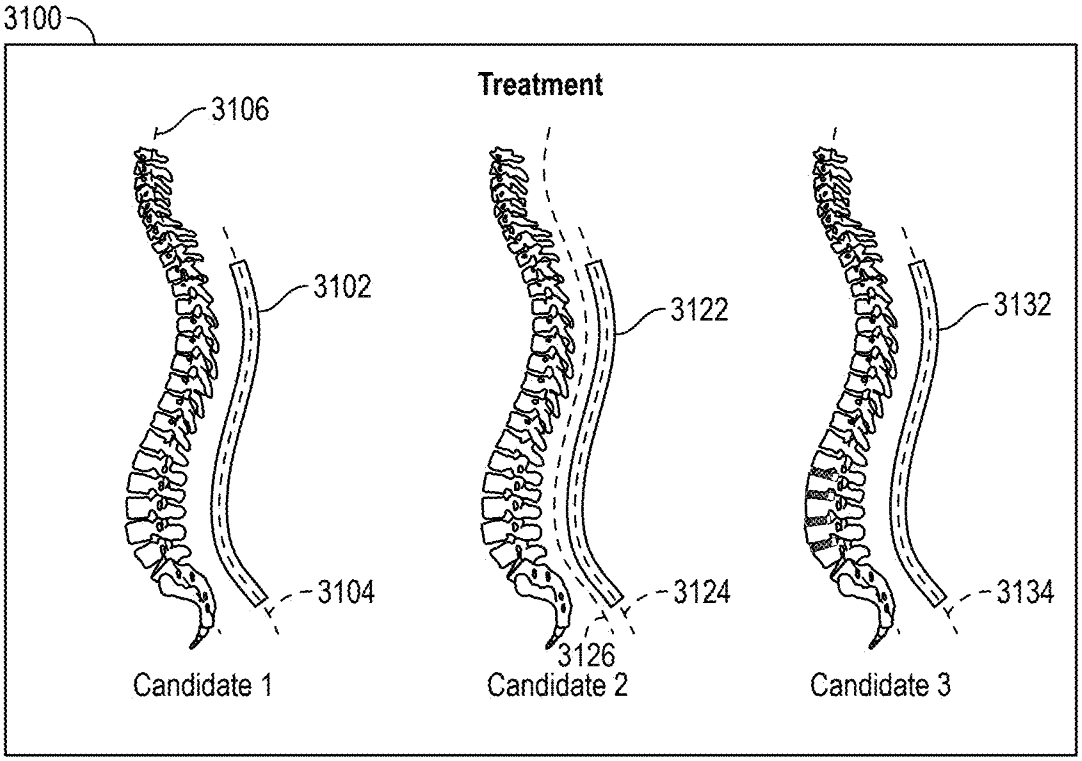
FIG. 31 illustrates a user interface for selecting a candidate treatment, according to at least some embodiments.

FIG. 31 illustrates a user interface 3100 for selecting a candidate treatment, according to at least some embodiments. Example candidate treatment 1 involves a spinal rod 3102 having a curvature 3104 that matches a spine curvature 3106 generated based on positions (e.g., centroids) of vertebral bodies. Example candidate treatment 2 involves a spinal rod 3122 with a curvature 3124 that produces the desired curvature 3126 of a spinal column. The curvature 3126 can be generated based on user- or ML-selected reference points. The reference points can include, for example, ends of the spinous processes, points along facet joints, or other points along vertebrae. The reference points can be selected such that the spinal rod 3122 matches selected features of vertebrae. Example treatment candidate 3 involves a spinal rod 3132 with a curvature 3134 that matches a spinal curvature of the spine. Example candidate treatment 3 also includes four intervertebral bodies positioned between vertebral bodies. The curvatures can be generated by one or more machine learning model, users, curve generation software based on, for example, one or more parameters (e.g., Cobb angles or other spinal curvature parameters), curve generation algorithms, etc. The system can select number and types of candidate treatments for review by the user.

Figure 32:
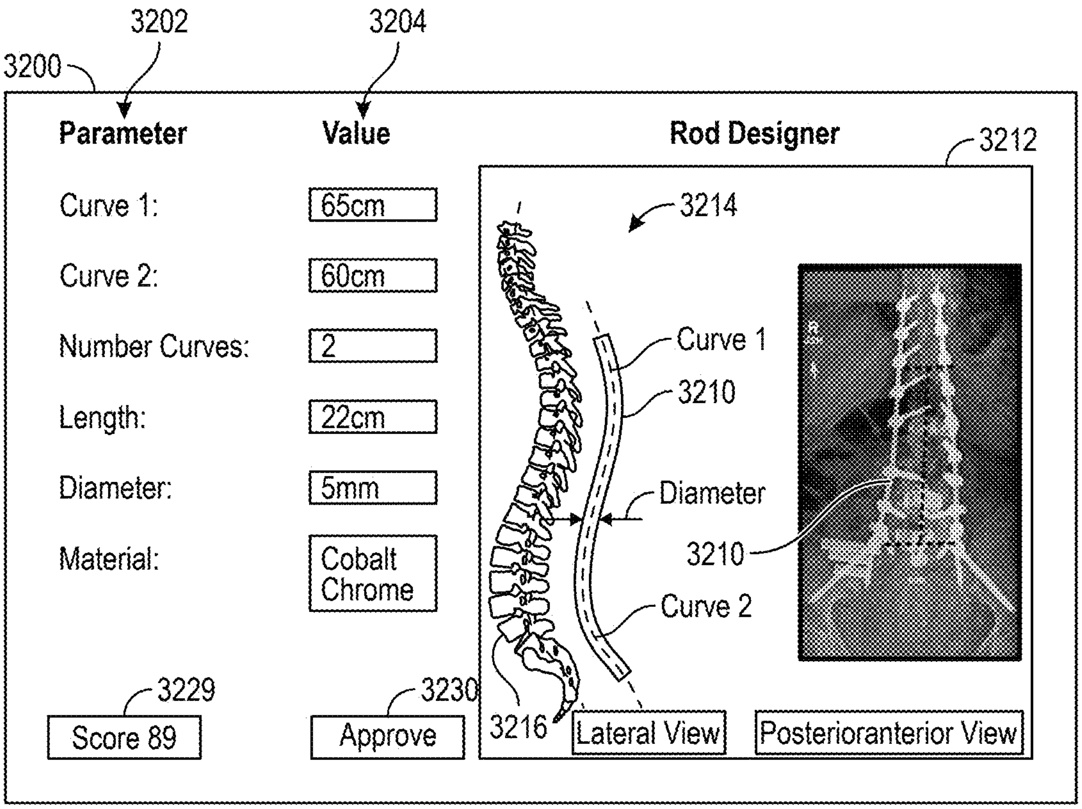
FIGS. 32-35 illustrate implant designer graphical user interfaces for designing and approving implants, in accordance with at least some embodiments.

FIG. 32 illustrates an implant designer graphical user interface 3200 for designing rods, in accordance with at least some embodiments. The user interface 3200 includes parameters 3202, values 3204, and a rod designer window 3212. The user interface 3200 can include one or more design parameters for a rod 3210, values for the respective parameters, and a design model 3214. The design model 3214 can include a model of the patient's anatomy 3216 and a model of the rod 3210. Parameters can be labeled in the design model 3214. A user can input or select values for the parameters and the design model 3214 can be dynamically updated. For example, a user can replace the curve 1 value of 65 cm with 70 cm, or the curvature can vary along sections or the length of the rod (different positions on the rod can be configured differently to achieve a desired spine curvature). The system can automatically update curve 1 to be 70 cm. A user can view the updated curve 1 in the design model 3214. This allows a user to adjust values of the parameters in real-time or near real-time.

The rod designer window 3212 can display anatomy, virtual models, planned outcomes, or the like. In the illustrated embodiment, the rod designer window 3212 displays a lateral view of a virtual model of the patient's spine in a corrected configuration. A virtual model of the rod 3210 is positioned to show how the rod 3210 will provide the desired correction. The rod designer window 3212 also displays a posterior/anterior view or any other view of the spine. In the illustrated embodiment, the posterior/anterior view is an image (e.g., an X-ray) of the patient with an overlaid image of the rod 3210. This allows the physician or user to evaluate how the rod 3210 will be positioned with respect to anatomical elements. The rod designer window 3212 can display any number and type of images disclosed herein. A user can select the displayed parameters and components to redesign or modify those parameters or components.

The system can generate a rod design score 3229 based on a planned targeted outcome, likelihood of achieving planned outcome, physician score, ML score, combinations thereof, etc. When the user modifies a value, the rod design score 3229 can be automatically updated so that the user can evaluate the modified value. A user can select the scoring routine used to generate the rod design score 3229. For example, the rod design score 3229 can be based on historical patient data for a healthcare provider, historical patient data of a specific physician, historical patient data from a particular type of procedure, or the like.

A user can select an approve input 3230 to approve the rod design. In response to approval, the design platform can perform one or more checks to confirm that the rod design is acceptable. If the rod design does not comply with one or more criteria, the system can notify the user that the designs, values, etc. should be modified or reevaluated. For example, if the design platform determines that the number and/or magnitude of curves should be increased, the system can indicate that the number of curves, illustrated as two curves in FIG. 32, should be increased to three or more. A user can then input a larger number of curves and evaluate the newly updated score. The design platform determines whether the design has acceptable values to ensure that the implant meets regulatory requirements, acceptable criteria, or the like.

Figure 33:
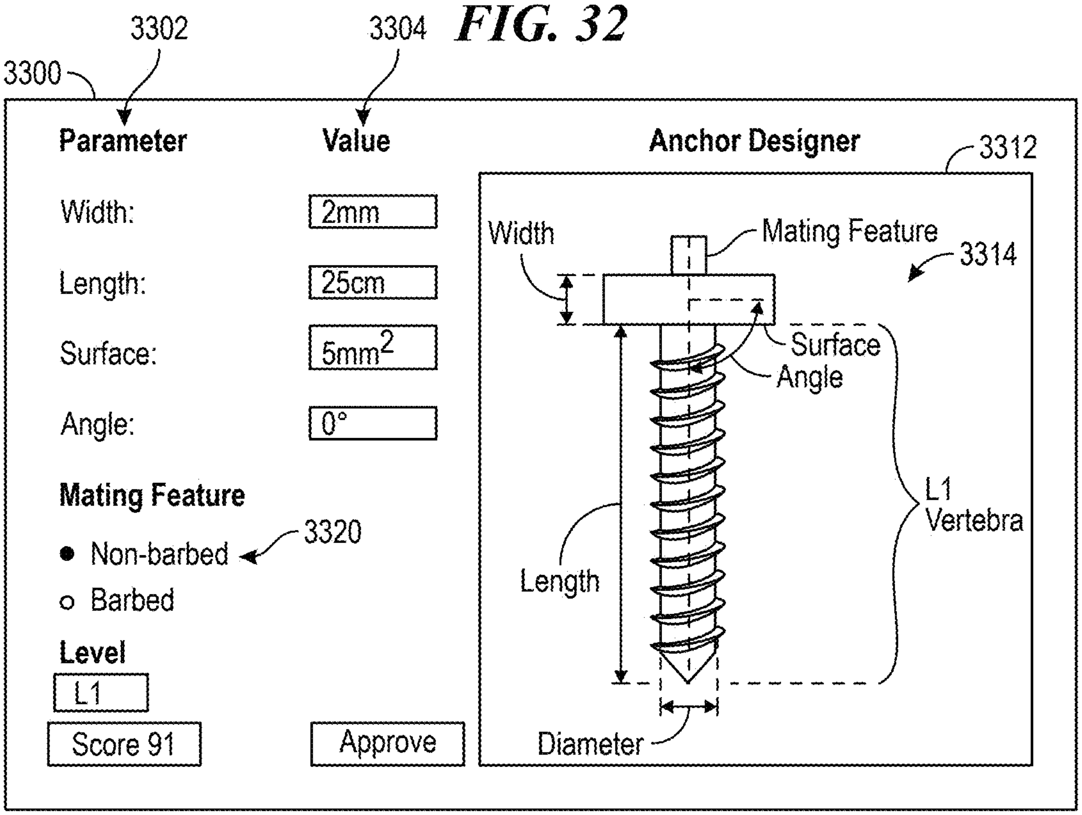

FIG. 33 illustrates an anchor designer graphical user interface 3300, in accordance with at least some embodiments. The user interface 3300 includes parameters 3302, values 3304, and an anchor designer window 3312. The parameters 3302 can include, without limitation, dimensions, surface information, angle information, thread information (e.g., pitch), or the like. The dimensions can include, for example, width, length, or the like. The surface information can include, for example, curvature of surfaces, surface area of the surfaces, texture of surfaces, or the like. The angle information can include, for example, the angle between the longitudinal axis of a bone screw and another feature, such as a face plate. The user interface 3300 can include a mating feature selector 3320 for selecting the configuration of a mating feature. For example, the mating feature can be non-barbed, barbed, or have another configuration. The level information can indicate the level of the anchor. For example, the user interface 3300 indicates that the anchor is designed for the L1 level. The anchor designer window 3312 can include a model 3314 of the anchor. The parameters can be identified to assist with the planning and/or design process. A user can select the parameter(s) in the anchor designer window 3312 to be updated and insert the new values in the value boxes.

Figure 34:
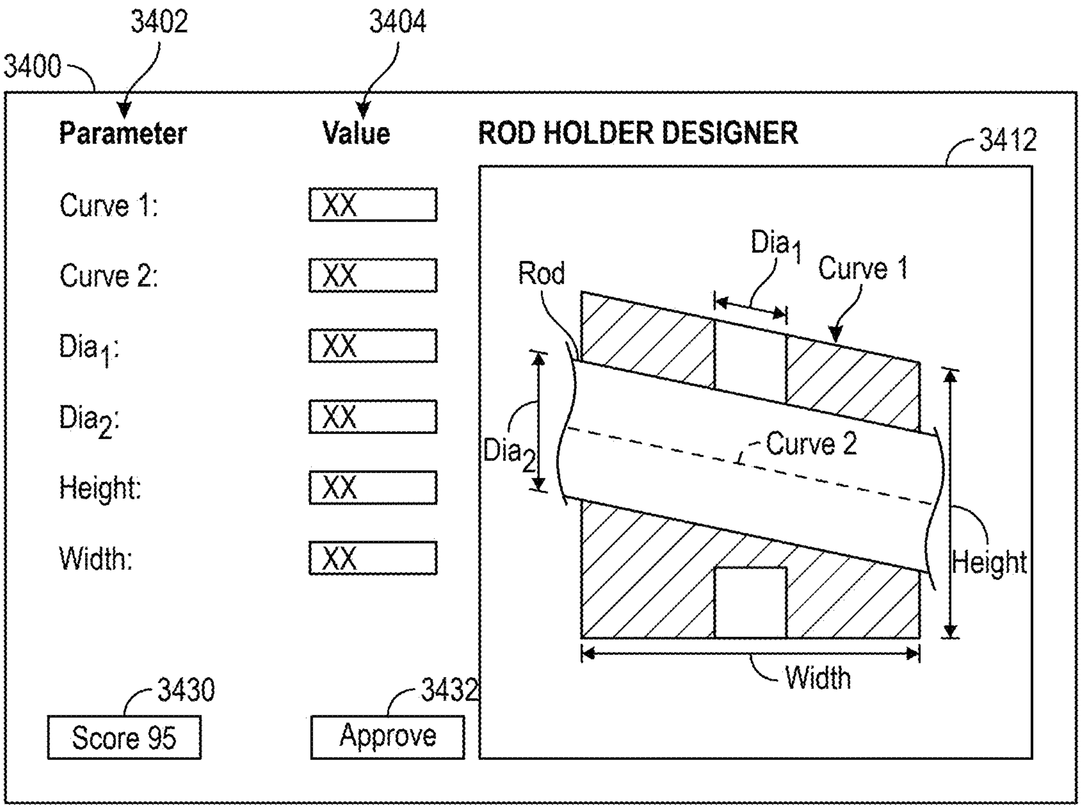

FIG. 34 illustrates a rod holder designer graphical user interface 3400, in accordance with at least some embodiments. The user interface 3400 includes parameters 3402, values 3404 (placeholder values "XX" can be replaced with values), and a rod holder designer window 3412. The parameters 3402 can be selected to achieve desired fits between other components. For example, the curve 1 parameter can be adjusted to match the curvature of a retainer, and the diameter 1 can be selected to match the protrusion of a retainer. The curve 2 parameter can be selected to match the curvature of the rod, and the diameter 2 can be selected to match a diameter of the rod. The width and height can be selected based on desired mechanical strength of the rod holder. In some embodiments, the design platform can automatically select the parameters based on parameters of the other components. For example, the diameter 2 can be selected to be slightly larger than the diameter of the rod. If the user modifies diameter 2, the system can automatically modify the diameter of the rod. This allows for parametric updating of any number of the inter-related models. A score 3430 can indicate the quality of the fit between the components. For example, the score can be increased from the illustrated 95 if the user inputs a value that decreases movement between the rod holder and the rod. A user can select the input 3432 when the rod holder is approved.

Figure 35:
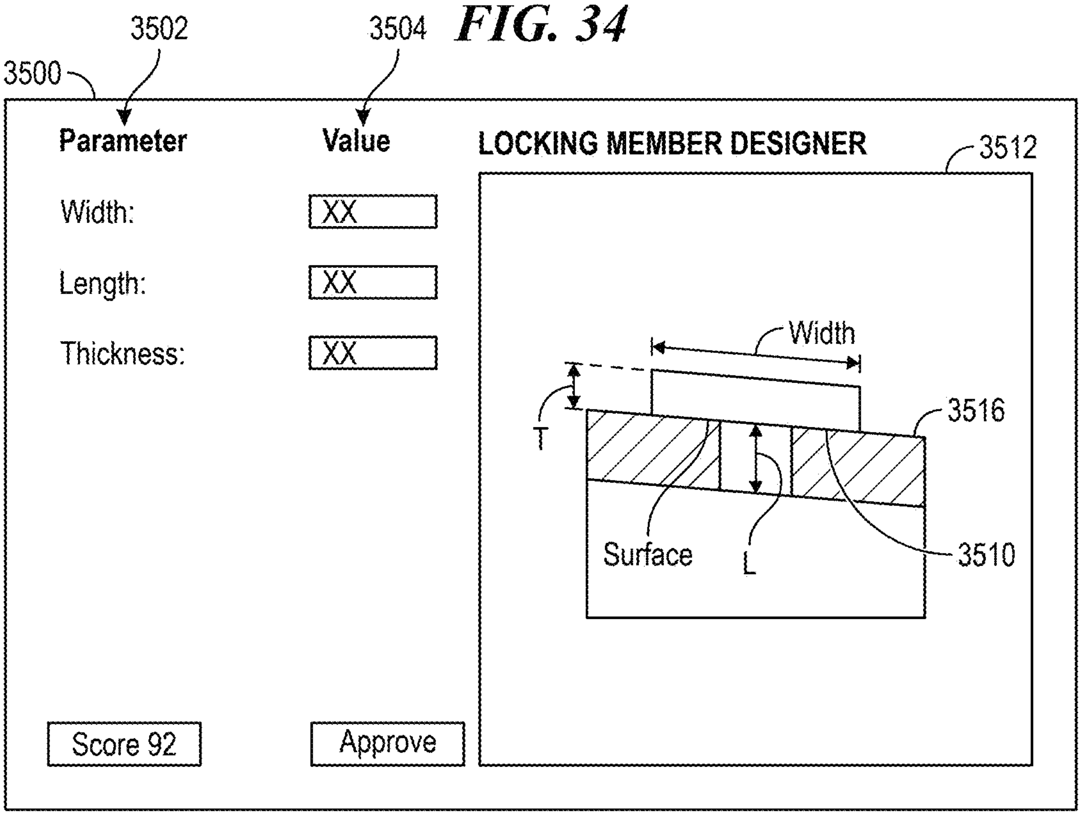

FIG. 35 illustrates a locking member designer graphical user interface 3500, in accordance with at least some embodiments. The user interface 3500 includes parameters 3502, values 3504, and a locking member designer window 3512. The locking member can have parameters selected to achieve a desired fit between adjacent components. The width of the plate can be increased or decreased to increase or decrease the interface 3510 between the plate and the exterior of the rod holder 3516. A length L of a protrusion can be increased or decreased to increase or decrease the length of the side opening.

Figure 36:
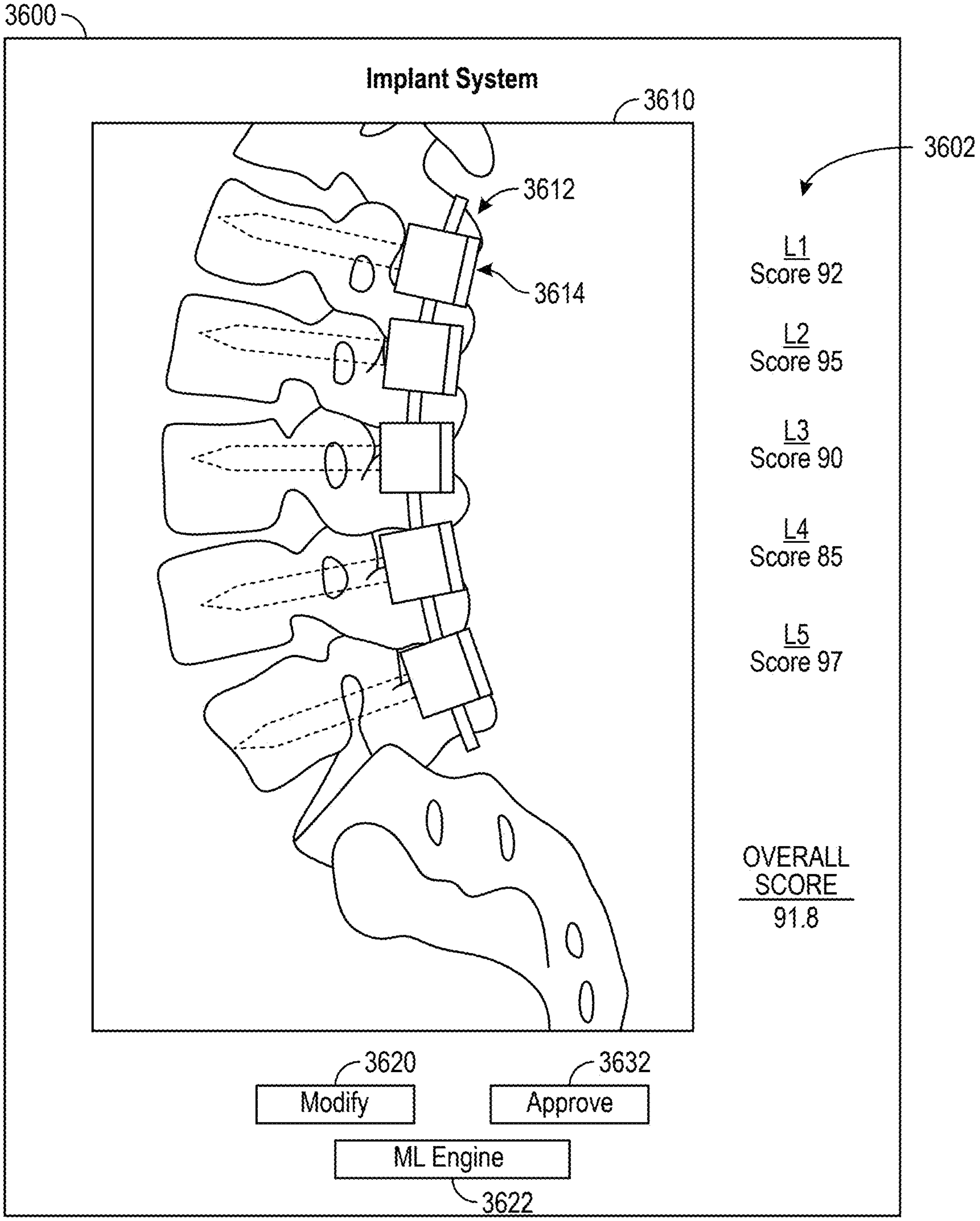
FIG. 36 illustrates a user interface for reviewing, modifying, and/or approving a multicomponent implant system, according to at least some embodiments.

FIG. 36 illustrates an implant system designer graphical user interface 3600, in accordance with at least some embodiments. The user interface 3600 can includes parameters, values, scores 3602 and an implant system designer window 3610 that shows a model 3612 of the patient's anatomy and an implant system 3614. The implant system 3614 can have sections corresponding to the L1-L5 regions. Each region can be individually scored to assess different portions of the implant system 3614. For example, the L2 score of 95 is greater than the L1 score 92. A user can modify the design of the L1 components to increase the L1 score, thereby increasing the overall score. For example, if the L1 score of 92 is increased, the overall score can be increased to be greater than the illustrated 91.8. A user can select to modify input 3620 to modify a portion of the implant system 3614. The user can select a region to be modified using a box, pointer, touchscreen, or other input. A user can then modify the implant using an implant design platform, as discussed in connection with FIGS. 31-35. The score for the respective components can be dynamically updated to provide real-time feedback. A user can evaluate the position of the anatomy achieved by the implant by viewing the model.

A user can select a machine learning (ML) engine input 3622 to perform at least a part of the design process using a machine learning module. For example, a user can select one or more levels to be designed using the machine learning module. The user can select other levels for manual design of components, which can be checked or modified using the machine learning engine. The user can select an approve input 3632 to approve the implant design. In some embodiments, the system can require that overall scores be equal to or greater than an acceptable score before allowing for user approval when the implant design is predicted to achieve at least a threshold outcome.

The user interface 3600 may allow for seamless, automated switching between different modes, such as a user design mode and an ML design mode for creating patient-specific implants. In the user design mode, a healthcare provider may manually input or adjust parameters for the implant design based on their expertise and preferences. The ML design mode, on the other hand, may utilize trained machine learning algorithms to automatically generate or optimize implant designs based on patient data, treatment goals, and historical outcomes. Users may have the flexibility to initiate the design process in either mode and switch between modes at any point during the design workflow. For example, a user may start with an ML-generated design and then switch to user mode to make fine-tuned adjustments, or vice versa. This hybrid approach may allow for leveraging both the efficiency of ML algorithms and the nuanced judgment of experienced clinicians in creating optimized patient-specific implants. The system may also provide real-time feedback and updated scores as designs are modified in either mode, helping guide users toward implant designs that may best meet the patient's needs and treatment objectives. In some embodiments, the system can switch modes based on one or more design triggers. The design triggers can include, without limitation, parameters of models being outside of an acceptable range, within a trigger range, etc. The ranges can be set by a user, the ML system, a healthcare provider, etc. For example, if a design is predicted to not meet acceptable design criteria (e.g., predicted to generate an unacceptable outcome, not meet regulatory requirements, etc.), the system can automatically switch the system to an ML compliance design mode to modify the design to meet acceptable design criteria.

In some embodiments, the system can have a third-party design mode in which the system can determine one or more parameters of a model for which additional information is needed. The system can query third-party databases (e.g., remote servers) to obtain information associated with the implant. The system can acquire the information and then integrate it into the model. For example, the system can design customized features of an implant system and can obtain recommended dimensions of third-party customized components, dimensions of standard components (e.g., pedicle screws, bone anchors, intervertebral bodies, etc.), or the like. This allows the system to generate customized implant systems that incorporate other manufacturers' customized components, standard components, or the like. In some embodiments, the system can obtain information from literature databases to determine parameters for implants. The number and type of design modes and switching mode triggers can be selected based on the user-inputted design goals.

Referring to FIGS. 31-36, virtual models can be multi-dimensional (e.g., two-dimensional or three-dimensional) virtual models and can include, for example, computer-aided design (CAD) data, material data, surface modeling, manufacturing data, or the like. The CAD data can include, for example, solid modeling data (e.g., part files, assembly files, libraries, part/object identifiers, etc.), model geometry, object representations, parametric data, topology data, surface data, assembly data, metadata, etc. The system can generate predicted intra-operative anatomical models, post-operative or corrected anatomical models, surgical plans (e.g., single-stage or multi-stage surgical plans), virtual models of implants, implant design parameters, and instruments using the virtual model of the patient anatomy. Examples of the foregoing are described in U.S. Pat. No. 11,793,577 and U.S. application Ser. Nos. 16/048,167, 16/242,877, 16/207,116, 16/352,699, 16/383,215, 16/569,494, 16/699,447, 16/735,222, 16/987,113, 16/990,810, 17/085,564, 17/100,396, 17/342,329, 17/518,524, 17/531,417, 17/835,777, 17/851,487, 17/867,621, 18/373,899, and 17/842,242, each of which is incorporated by reference herein in its entirety.

Virtual models can include a first set of anatomical element models with high-fidelity surface topologies for designing the patient-specific implants. The 3D model can include a second set of anatomical element models for measuring spinal metrics for predicting a surgical outcome associated with implantation of the one or more patient-specific implants. In some cases, one or more of the anatomical element models of the second set have less feature data than all or some of the anatomical element models of the first set. The system can generate the 3D model by positioning, orienting, and/or scaling anatomical element models of the first set of anatomical elements for incorporation into the second set of anatomical elements. The 3D models can be modified to generate new 3D models that represent different stages of treatment plans. The new 3D models can be modified based on acquired patient data, user input, or the like. In some embodiments, one or more 3D models are generated to represent one or more stages of a treatment plan. Implant models with high-fidelity surface topologies can be generated and fit with the anatomical virtual models.

In some embodiments, the system can generate X-ray-fidelity anatomical element models based on one or more standing X-ray images. The system can generate tomographic-fidelity (e.g., polygon counts of number of polygons or triangles used to represent the model's surface; edge and curve smoothness, surface quality (surface roughness, continuity, and the presence of imperfections or artifacts that may affect the model's fidelity), level of geometric detail (inclusion of fine features, intricate structures, and smaller elements), matching to images, etc.) anatomical element models based on a set of tomographic images of the first multi-dimensional image data. The X-ray-fidelity anatomical element models have a resolution below a threshold fidelity and the tomographic-fidelity anatomical element models have a fidelity above the threshold fidelity, resolution above a threshold resolution, etc. The standing X-ray images can be post-operative images captured after the patient has partially or fully completed recovery from a surgical stage.

The system can generate a 3D multi-region spine model (e.g., including a lumbar region, a cervical region, and/or a thoracic region of the patient's spine) of the patient based on the first multi-dimensional image data and a 3D partial spine model (e.g., including a lumbar region model having surface topology data for designing one or more implants) matching the corresponding region of the spine imaged in the second multi-dimensional image data. The system can generate a 3D multi-region simulation model by combining anatomical elements of the 3D partial spine model with the 3D multi-region spine model. The system can replace lower-fidelity anatomical element models (e.g., based on X-ray images) of the 3D multi-fidelity spine model with the corresponding higher-fidelity anatomical elements (e.g., based on CT images or MRI study) of the 3D partial spine model anatomical elements. The system can collect additional multi-dimensional image data in other loading states and generate a replacement virtual model of an anatomical element for placement in the virtual 3D model. Example 3D multi-region spine models are discussed in U.S. application Ser. No. 18/373,899, which is incorporated by reference herein in its entirety. Virtual implants can be added to the 3D multi-region spine models to generate a composite model (e.g., model of implants and anatomy), and parametric parameters between the virtual implants and spine models can be determined. The parametric parameters can be used to dynamically modify multiple parameters of the composite model.

The implant designs can be generated from the virtual model of the implant, or drawn by the user (e.g., drawn via a touch screen). In some embodiments, the system can generate an implant profile based on the viewing perspective and/or implant's current anatomical orientation. In some embodiments, the system can identify one or more image keying features of the implant. Example image keying features can include, for example, opaque markers, edges, or other features of the implant that can be identified using image processing techniques. The system can retrieve image keying feature information from a database containing designs for the implant. For example, a patient-specific implant can have associated virtual models (e.g., three-dimensional virtual model, CAD files, etc.), keying feature files, data for identifying implants, data for determining implant orientations, unique keying features, or the like. The system can match reference image keying features with corresponding features of the implant in the images to determine the position and orientation of the implant in the patient.

The system can perform one or more synchronization routines using image data and non-image data to command the image system (e.g., camera system, robotic C-Arm imaging system, X-ray system) and/or provide instructions for obtaining additional images. For example, synchronization routines can include matching landmarks (e.g., keying features) to synchronize or nearly synchronize images (e.g., images taken for performing checks) with one or more virtual models, pre-operative plans, intra-operative plans, or the like. Additionally or alternatively, the system can retrieve and manipulate components of the virtual 3D model based on the captured images. For example, the components of a virtual 3D model can be manipulated to be aligned with the radiograph taken by the cameras, X-ray, C-Arm, or the like. The virtual 3D model (or components thereof) can be manipulated (e.g., by zooming, stretching, cropping, and/or rotating the virtual 3D model) to align the virtual 3D model with radiograph. The virtual 3D model can include an anatomical model representing anatomy of a patient, implant model, instrument model, or the like. In some embodiments, the alignment can be performed using one or more best fit routines using, for example, one or more edge detection routines, segmentation routines, filtering routines, image recognition routines, or combinations thereof. The system can confirm placement of an implant by confirming that the implant in the intra-operative image (e.g., the radiograph) is in the same placement as the implant in the pre-operative surgical plan. The placement can be scored based on differences between the pre-operative and intra-operative images. The scoring routine can determine the distance between a target position window and the actual position of the implant. If the actual position is within the target position window, the system can indicate the implant is located at the target location. The target position window can be determined using ML models, user input, or the like. In some embodiments, the system can confirm that the implant is positioned at a target location based on identified portion(s) of the implant contacting targeted anatomical feature(s).

In some embodiments, the system can perform real-time checks using one or more captured images (e.g., sequentially captured images obtained using a C-Arm machine) within an augmented reality (AR) application. The system can use a camera feature within the AR application to view intra-operative radiograph images on a user interface. The camera feature of the AR application does not require a camera on the user interface to take the intra-operative image; rather, it displays the intra-operative radiograph images on the user interface. As shown on the user interface, the radiograph image can be taken prior to implantation of the implant.

The system can perform any number of implant designs and position checks to confirm that the implant design and/or location is acceptable. The position checks can be non-invasive image-guided checks for intra-operatively analyzing the current location of the implant based on obtained images of the patient. The system can identify the implant in the images and then synchronize implant data in the surgical plan with the patient images. For example, the system can synchronize a virtual anatomical model of the surgical plan with radiograph images and then compare the position of the physical implant to a target or acceptable implant position. This process can be repeated until the implant is positioned at an acceptable location in the patient based on the comparison. During a surgical procedure, images can be repeatedly taken to evaluate delivery of the implant.

FIGS. 37-40 illustrate flow diagrams for designing implants and/or fixation assemblies, in accordance with some embodiments. The user interfaces of FIGS. 30-36 can be used to perform at least a portion of those methods performed, at least in part, by the computing system 100 of FIG. 1, user device 200 of FIG. 2, or other components or systems disclosed herein. For example, the display 122 of FIG. 1 can display the interfaces discussed in connection with FIGS. 7A-10C and 30-36. In another embodiment, the display 230 of FIG. 2 can be used to display those interfaces used to perform the steps or methods discussed in connection with FIGS. 37-40.

Figure 37:
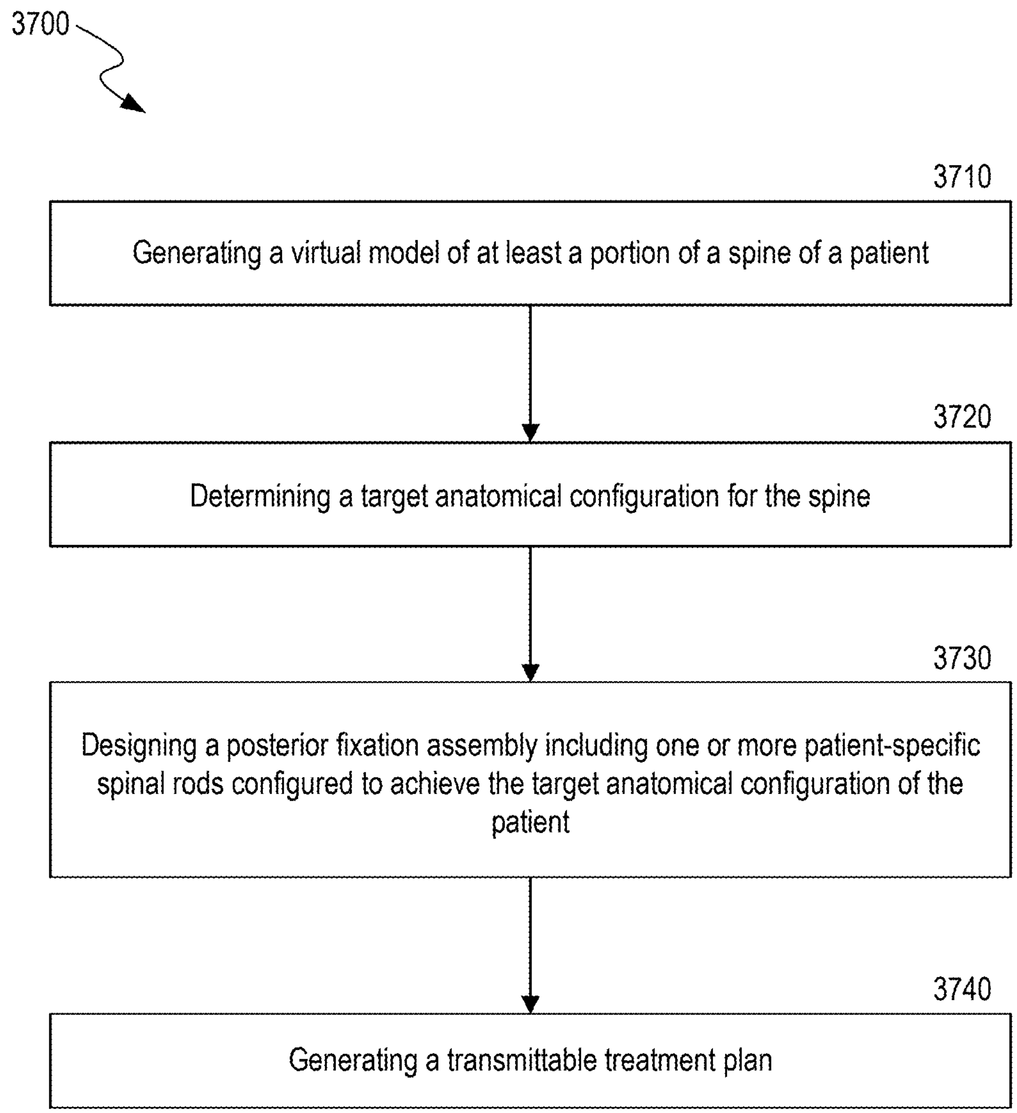
FIG. 37 is a flow diagram illustrating a method for designing a patient-specific posterior fixation assembly, according to at least some embodiments.

FIG. 37 illustrates a flow diagram for a method 3700 for designing a patient-specific posterior fixation assembly. At step 3710, a system may generate a virtual model of at least a portion of a spine of a patient. The virtual model may be created using medical imaging data, such as CT scans, MRI images, X-rays, or other imaging modalities. Image processing techniques and 3D reconstruction algorithms may be employed to generate a detailed three-dimensional representation of the patient's spinal anatomy.

At step 3720, the system may utilize a multi-component design platform to determine a target anatomical configuration for the spine. This process may involve analyzing the virtual model to identify anatomical abnormalities, deformities, or other conditions requiring correction. The multi-component design platform may then determine an optimal corrected configuration that addresses the patient's specific condition, surgical goals, physician input, etc.

At step 3730, the system may utilize the multi-component design platform and the virtual model in the target anatomical configuration to design a posterior fixation assembly. This assembly may include one or more patient-specific spinal rods configured to achieve the target anatomical configuration of the patient. The spinal rods may be customized in terms of length, curvature, material properties, or other characteristics to match the patient's unique spinal anatomy and correction needs.

The posterior fixation assembly may also include anchor assemblies. These anchor assemblies may be configured to anchor to vertebrae and to hold the one or more patient-specific spinal rods to achieve the target anatomical configuration when implanted in the patient. The anchor assemblies may include features such as pedicle screws, anchors, tethers, or other fixation devices tailored to the patient's vertebral anatomy.

At step 3740, the system may generate a transmittable treatment plan that includes planned values (e.g., planned spinopelvic metrics or planned spinal metrics). These metrics may include measurements such as sagittal balance, pelvic incidence, lumbar lordosis, or other relevant parameters that quantify the expected post-operative spinal alignment and/or the target anatomical configuration.

In some embodiments, one or more of the anchor assemblies may have a rod-receiving portion geometrically congruent to a respective section of one of the patient-specific spinal rods. This congruence may allow for improved fit and stability between the rod and the anchor assembly, potentially enhancing the overall performance of the posterior fixation system. The anchor assemblies may include various types of fixation devices. In some cases, each of the anchor assemblies may include a bone screw or an anchor. These bone screws may be designed with specific dimensions, thread patterns, or other features tailored to the patient's vertebral anatomy and bone quality, potentially improving fixation strength and reducing the risk of loosening or failure.

The method 3700 can also be used to design patient-specific artificial discs, interbody devices, or the like. In some embodiments, a multi-component design platform can design an artificial disc configured to provide mobility to a patient's spine. The multi-component design platform can design fixation elements (e.g., anchors, bone screws), endplates for interfacing with vertebral endplates, joints, and other features of the artificial disc. The transmittable plan can include planned spinopelvic metrics, planned post-operative biomechanics, and other information. In some embodiments, the multi-component design platform can design multiple interbody devices each configured to be implanted at a specific level for a multi-level fusion procedure. Each of the patient-specific implants can be designed based, at least in part, on designs of other intervertebral implants. This allows for concurrent or sequential analysis of planned outcomes at multiple levels.

Figure 38:
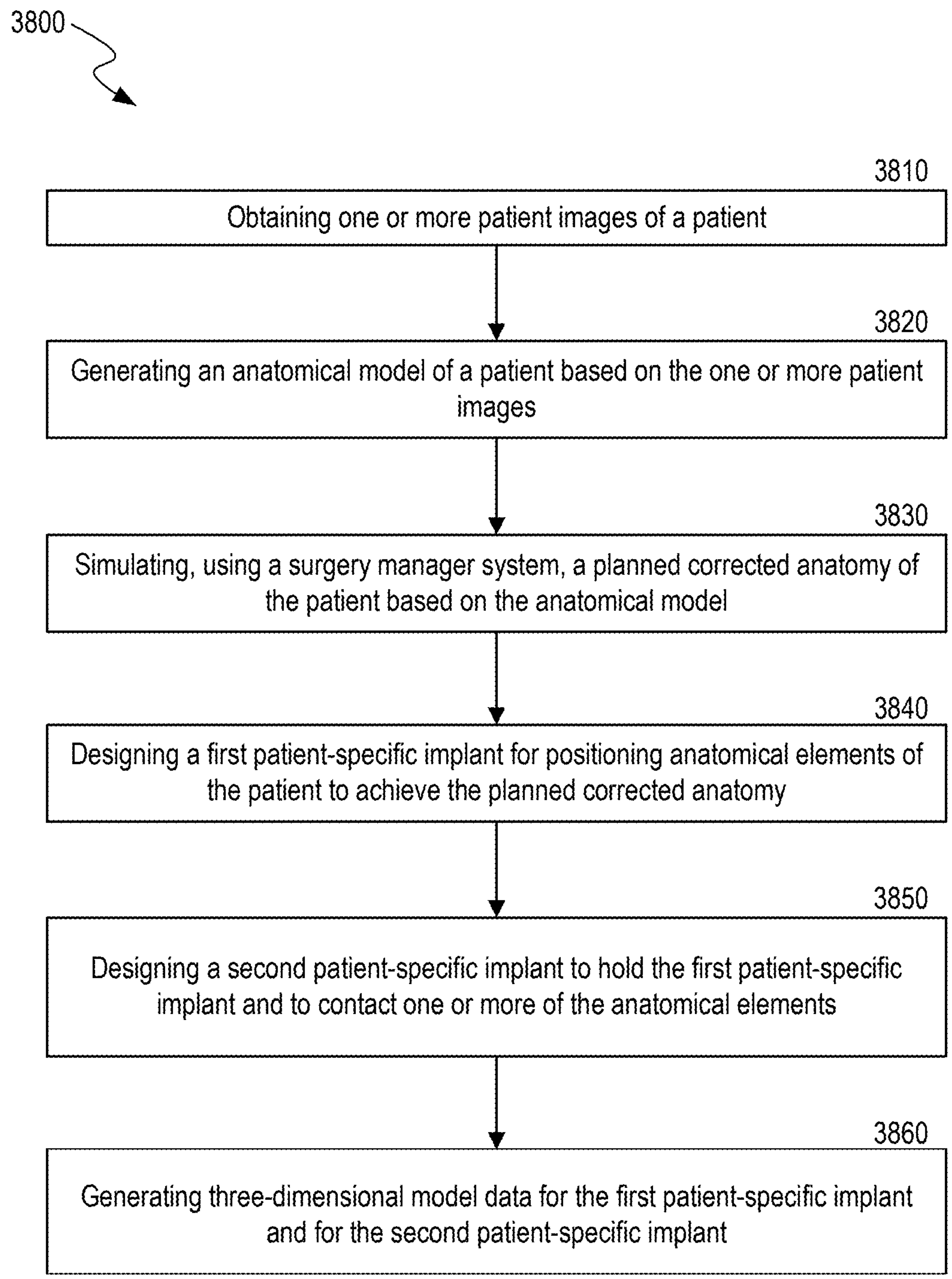
FIG. 38 is a flow diagram illustrating a method for designing and manufacturing patient-specific implants, according to at least some embodiments.

FIG. 38 illustrates a flow diagram of a method 3800 for designing and manufacturing patient-specific implants. At step 3810, the system may obtain one or more patient images using various imaging modalities. These images may include, without limitation, X-rays, CT scans, MRI scans, ultrasound images, or other diagnostic imaging data.

At step 3820, the system may generate an anatomical model of the patient based on the obtained images. This anatomical model may be a detailed three-dimensional representation of the patient's anatomy, created using image processing techniques and reconstruction algorithms.

At step 3830, a surgery manager system may use the anatomical model to simulate a planned corrected anatomy for the patient. This simulation may take into account the patient's current anatomical configuration, the desired surgical outcome, and various biomechanical factors. The simulation may allow for visualization and analysis of potential surgical corrections before any actual intervention takes place.

At step 3840, based on the simulated planned corrected anatomy, the system may design a first patient-specific implant. This implant may be specifically configured to position anatomical elements of the patient to achieve the planned corrected anatomy. The design process may involve customizing various parameters of the implant, such as its size, shape, material properties, and other characteristics, to match the patient's unique anatomical requirements and the planned correction.

At step 3850, the system may also design a second patient-specific implant that is configured to hold the first patient-specific implant and to contact one or more of the anatomical elements. This second implant may be designed to work in conjunction with the first implant, providing additional support, stability, or fixation as needed to achieve and maintain the desired anatomical correction. The system can design additional patient-specific implants.

For each patient-specific implant, the system may select a plurality of design parameters based on the implant type. These parameters may include, but are not limited to, curvature, number of curves, dimensions, material properties, surface features, and attachment mechanisms. The system may then select values for each of these parameters based on the planned corrected anatomy and the specific requirements of the patient.

At step 3860, using the selected parameter values, the system may generate model data of each patient-specific implant. The model data may be three-dimensional representations that accurately depict the geometry, features, and characteristics of the designed implants. The model data is configured to be transmitted to manufacture the first patient-specific implant and the second patient-specific implant. In some embodiments, the model data is transmitted to a manufacturing system (e.g., manufacturing system 124 of FIG. 1), which converts the model data into manufacturing data. The manufacturing system can manufacture the implant based on the manufacturing data. An implant analyzer (implant analyzer 129 of FIG. 1) can analyze the manufactured implant to confirm that the implant meets one or more manufacturing criteria. This process can be repeated to sequentially or concurrently manufacture implants and/or components of an implant system.

The system may determine specific positions and configurations for each of the patient-specific implants. For example, it may determine a first position and configuration for a first patient-specific implant that will achieve the desired anatomical correction. A second patient-specific implant may then be designed with a configuration that allows it to couple with the first implant in its specified configuration and hold it securely in the determined position. By designing these implants to work together in a coordinated manner, the system may create a comprehensive, patient-specific solution for achieving the desired anatomical correction. This approach may allow for more precise and effective surgical interventions, potentially leading to improved patient outcomes.

Figure 39:
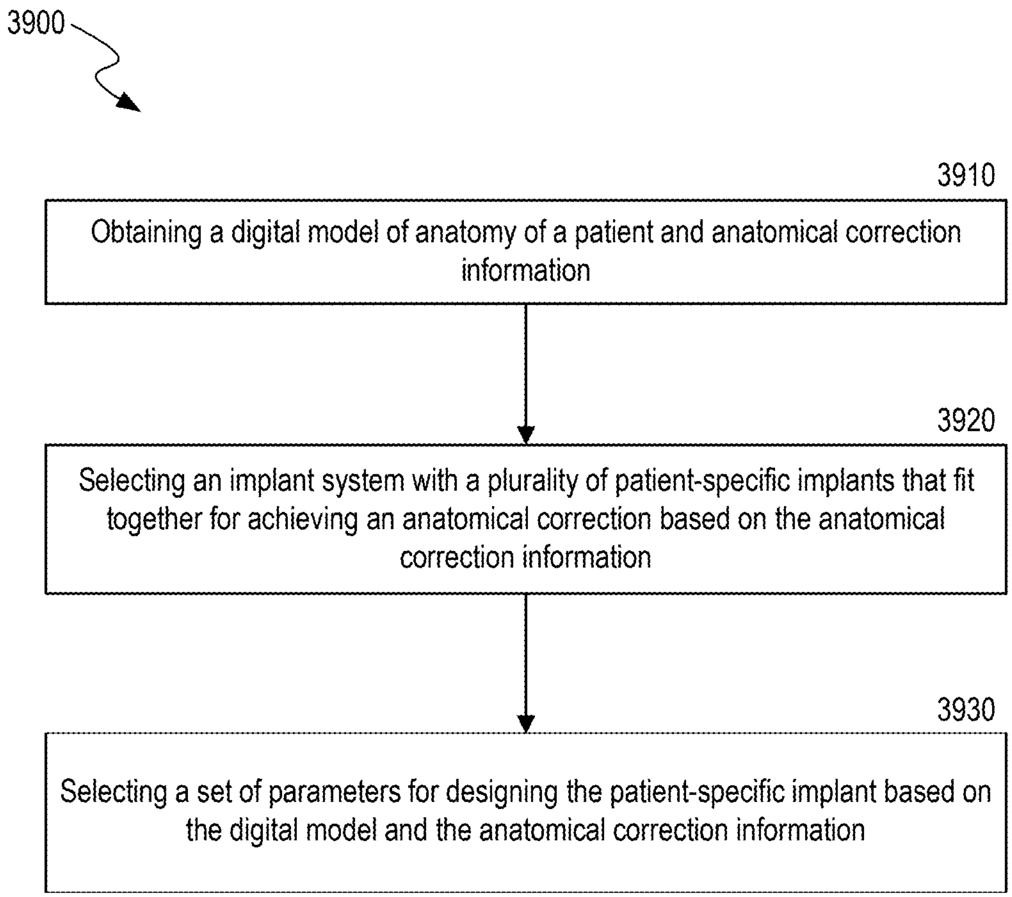
FIG. 39 is a flow diagram illustrating a method for designing patient-specific implants using a graphical user interface, according to at least some embodiments.

FIG. 39 illustrates a flow diagram of a method 3900 for designing patient-specific implants using a graphical user interface. At step 3910, a system may obtain a digital model of anatomy of a patient and anatomical correction information. The digital model may be generated from medical imaging data. The anatomical correction information may include details about the desired surgical outcome, such as target spinal alignment or joint positioning.

At step 3920, the system may select an implant system with a plurality of implants (e.g., patient-specific implants, standard implants, etc.) that fit together for achieving an anatomical correction. This selection process may involve analyzing the patient's anatomy and the desired correction to determine the most appropriate combination of implants.

At step 3930, the system may select a set of parameters for designing a set of patient-specific implants based on the digital model and the anatomical correction information. These parameters may include dimensions, shapes, curvatures, material properties, and other characteristics specific to each implant component.

The system may provide an implant designer graphical user interface (GUI) for displaying the set of parameters, values for the respective parameters, a planned anatomy of the patient, and a model of the patient-specific implant positioned along the planned anatomy. The model of the patient-specific implant may represent the values of the selected parameters. This GUI may allow for interactive visualization and manipulation of the implant designs in relation to the patient's anatomy. In some embodiments, the implant designer GUI can display the implant system comprising all patient-specific implants and another implant system comprising both patient-specific implants and standard implants. A user can compare planned outcomes for each implant system. This allows a user to evaluate both patient-specific implant systems and hybrid implant systems. Optionally, the GUI can display standard implant systems for evaluating whether patient-specific or standard implant systems should be utilized.

In some aspects, the system may determine one or more fitting relationships between two or more of the patient-specific implants. The fitting relationships can describe and/or quantify how the implants interact with each other when inserted, assembled, and/or implanted. The system may modify at least one model of the two or more patient-specific implants based on the one or more fitting relationships. This modification process may ensure that the implants work together effectively as a system. In some embodiments, the fitting relationship can be based on, without limitation, coupling strength, type of fit, tolerances, area of contact, enmeshed features, or the like. A user can select the fitting relationship(s) used to evaluate how implants interact with one another, mechanical characteristics of implant systems, or the like. A user can score different types of coupling arrangements and this score can be used to score other components, implant systems, etc. In some embodiments, the system can individually analyze interfaces between implants and display coupling strengths, fatigue life at interfaces, fracture toughness at interfaces, or the like.

The system may generate a model of the implant system having the plurality of implants fitting together to achieve the anatomical correction of the patient. This model may provide a comprehensive view of how the entire implant system will function when implanted.

In some embodiments, the system may identify an interface between two of the patient-specific implants. The system may select a fitting routine based on the interface and modify, using the fitting routine, one or both of the two patient-specific implants to achieve a threshold fit. This process may ensure optimal interaction between implant components.

The system may modify only portions of the one or both of the two patient-specific implants positioned outside of bony anatomy. This approach may preserve the portions of the implants designed to interface directly with the patient's bone while optimizing the connections between implant components.

In some aspects, the system can dynamically modify a model of the implant system. This may involve modifying a first one of the patient-specific implants according to a modified value for the first one of the patient-specific implants, modifying a second one of the patient-specific implants to fit with the first one of the patient-specific implants, and generating a viewable image of the modified model of the implant system with the modified first and second one of the implants. This dynamic modification process may allow for real-time updates and visualization of design changes.

The system may simulate, using a surgery manager system (e.g., the surgery manager system of server 106 of FIG. 1, SPC platform 109 of FIG. 1, etc.), a predicted corrected anatomy of the patient based on a simulated implantation of the implant system using a virtual model representing anatomy of the patient. The system may generate, using the surgery manager system, surgical feedback for assisting an individual with the modified implant system in the surgical procedure. This surgical feedback may be based on the simulated implantation. The system may send, from the surgery manager system, a viewable surgical plan for viewing by the individual.

In some embodiments, the system may determine whether a threshold amount of patient data of the patient is available for intra-operatively simulating implantation of the intra-operatively modified implant to meet a confidence score.

The intra-operative surgical feedback may be sent after determining that the threshold amount of patient data of the patient is available.

The plurality of patient-specific implants may include a rod. The system may modify one or more parameters of the rod (e.g., curvature of the rod, varying diameter of the rod, non-varying diameter of the rod, and/or a length of the rod) based on the patient's anatomy or desired correction.

In some aspects, the system may determine whether the implant system meets a plan generation threshold. In response to the implant system meeting the plan generation threshold, the system may generate a surgical plan based on usage of the implant system.

The system may link a surgery manager system to a plan (e.g., plan 157 of FIG. 1, plan 1000 of FIG. 10A, plan 1020 of FIG. 10B, or overlaid image 1060 of FIG. 10C, or other plans disclosed herein) displayable by the user device. The surgery manager system may store parametric information of the model. The system may synchronize, using the surgery manager system, the interactive surgical plan and a simulator module that receives values to display new simulation data generated by the simulator module for concurrently evaluating the plurality of patient-specific implants.

In some embodiments, the system may generate a measurable virtual model of anatomy of the patient based on simulated implantation of the implant system. The system may select at least one measuring algorithm from a set of measuring algorithms based on a target outcome for a planned surgical procedure. The system may measure one or more planned metrics for evaluating the planned surgical procedure using the at least one measuring algorithm and the measurable virtual model of anatomy of the patient. The surgical feedback may include the one or more planned metrics. U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA" discloses generation of models, measuring of models, and imaging techniques. U.S. Pat. No. 11,793,577 is incorporated by reference in its entirety.

Figure 40:
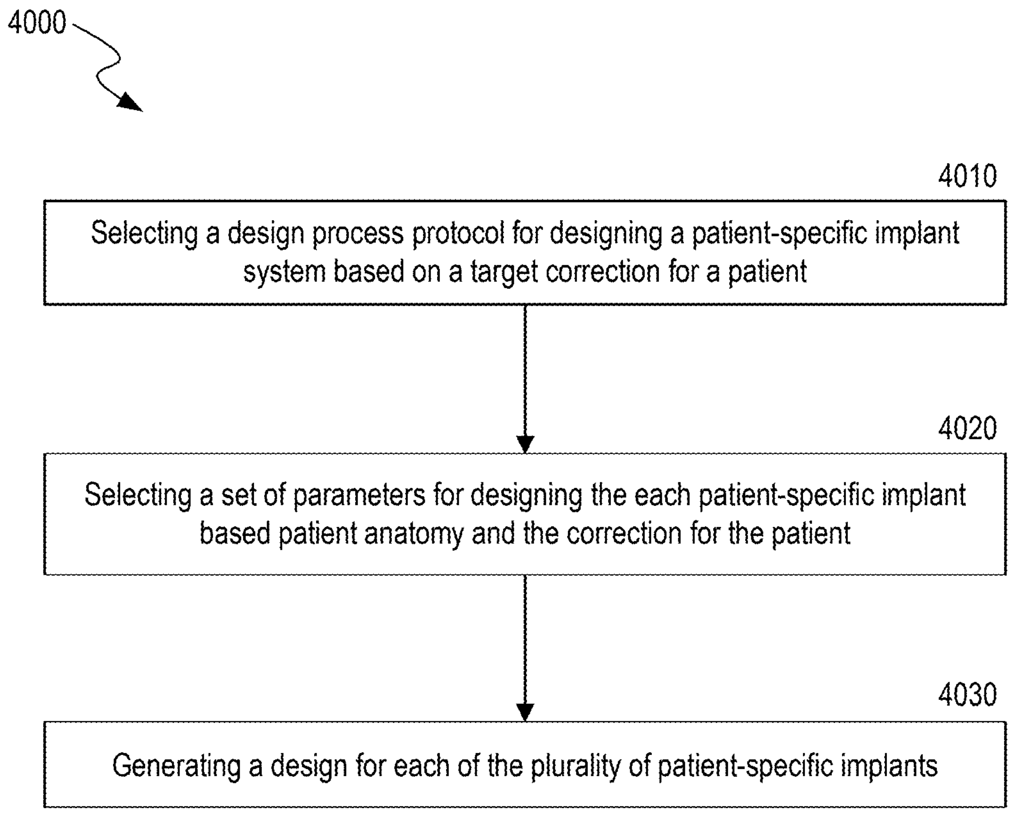
FIG. 40 is a flow diagram illustrating a method for designing a patient-specific implant system using a design process protocol, according to at least some embodiments.

FIG. 40 illustrates a flow diagram for a method 4000 of designing a patient-specific implant system, in accordance with at least some embodiments. At step 4010, a system may select a design process protocol for designing a patient-specific implant system based on a target correction for a patient. The design process protocol may be chosen from various options, such as a user-controlled design protocol or a machine learning process protocol, depending on the specific requirements of the case and the preferences of the medical team.

At step 4020, for each of a plurality of patient-specific implants of the patient-specific implant system, the system may select a set of parameters for designing the patient-specific implant based on patient anatomy and the correction for the patient. These parameters may include dimensions, shapes, materials, surface features, or other characteristics relevant to the implant's function and integration with the patient's anatomy.

The system may generate an implant designer graphical user interface (GUI) for displaying the set of parameters for the design process protocol, values for the respective parameters, and a planned anatomy of the patient. This GUI may provide a visual representation of the implant design process, allowing for interactive adjustments and real-time feedback.

At step 4030, the system may generate a design for each of the plurality of patient-specific implants such that the patient-specific implants cooperate to provide anatomical correction to the patient based on the target anatomical correction. This cooperative design approach may ensure that the implants work together as a system to achieve the desired outcome.

In some cases, the correction for the patient may include spinal realignment, and the planned anatomy of the patient may be represented by a virtual model of the anatomy of the patient with the correction. This virtual model may allow for visualization of the expected post-operative outcome and may guide the implant design process.

The design process protocol may include a virtual modeling protocol for generating a model of anatomy of the patient and a parametric modeling process for generating a parametric model of the patient-specific implant system. This combination of modeling techniques may allow for a comprehensive and flexible design approach.

In some embodiments, the system may obtain measurements using a model of the anatomy and generate a parametric model of the patient-specific implant system based on these measurements. This approach may ensure that the implant system is tailored to the specific dimensions and features of the patient's anatomy.

The system may virtually position the parametric model of the patient-specific implant system along the model of anatomy of the patient and generate viewable data illustrating the patient-specific implant system virtually positioned in the patient. This visualization may aid in assessing the fit and function of the implant system before manufacturing or implantation.

In some aspects, the system may generate a parametric model of the patient-specific implant system, modify the parametric model based on a modification to one or more of the values, and determine whether the modified parametric model meets at least one design criteria. This iterative process may allow for refinement of the implant design to optimize its performance and fit.

The at least one design criteria may be inputted by a user or may include a target correction to the patient. This flexibility in defining design criteria may allow for customization of the implant system to meet specific surgical goals or patient needs.

The system may generate a manufacturing design for each of the plurality of patient-specific implants for individually manufacturing each of the plurality of patient-specific implants. This may enable the production of customized implants that are precisely tailored to the patient's anatomy and the planned correction.

In some embodiments, the system may generate an implant designer graphical user interface (GUI) linked to a parametric model of the patient-specific implant system. The implant designer GUI may be configured to display the patient-specific implant system modified to accommodate a modification of one of the patient-specific implants. This feature may allow for real-time visualization of design changes and their impact on the overall implant system. U.S. patent application Ser. No. 18/408,452, filed Jan. 9, 2024, titled "SYSTEM FOR MODELING PATIENT SPINAL CHANGES" discloses example model techniques, parametric modeling modifications, and visualization technique. U.S. patent application Ser. No. 18/408,452 is incorporated by reference in its entirety.

The system may modify one of the patient-specific implants based on a modification to another one or more of the patient-specific implants. This interdependent design approach may ensure that changes to one component of the implant system are appropriately reflected in related components, maintaining the overall effectiveness of the system.

The system can intraoperatively modify one of the patient-specific implants based on an intraoperative modification (e.g., a physician modification) to another one or more of the patient-specific implants. U.S. patent application Ser. No. 18/415,577, filed Jan. 17, 2024, titled "PATIENT-SPECIFIC IMPLANT DESIGN AND MANUFACTURING SYSTEM WITH A SURGICAL IMPLANT POSITIONING MANAGER" discloses designing and positioning steps combinable with techniques and steps disclosed herein. U.S. patent application Ser. No. 18/415,577 is incorporated by reference in its entirety. U.S. application Ser. No. 18/384,762, filed Oct. 27, 2023, titled "SYSTEMS AND METHODS FOR SELECTING, REVIEWING, MODIFYING, AND/OR APPROVING SURGICAL PLANS" discloses systems and methods for reviewing and analyzing plans, designs, and procedures that can be incorporated into and/or used with technology disclosed herein. U.S. patent application Ser. No. 18/384,762 is incorporated by reference in its entirety. Example patient-specific implants are disclosed in the incorporated by reference applications and patents.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A surgical system comprising:
   one or more processors; and
   one or more memories storing instructions that, when executed by the one or more processors, cause the surgical system to perform a process comprising:
      generating a virtual model of at least a portion of a spine of a patient;
      determining, using a multi-component design platform, a target anatomical configuration for the spine;
      designing, using the multi-component design platform and the virtual model in the target anatomical configuration, a posterior fixation assembly including
         one or more patient-specific spinal rods configured to achieve the target anatomical configuration of the patient; and
         a plurality of anchor assemblies configured to anchor to vertebrae and to hold the one or more patient-specific spinal rods to achieve the target anatomical configuration when implanted in the patient; and
      generating a transmittable treatment plan including at least one of planned spinopelvic metrics or planned spinal metrics for the target anatomical configuration.
2. The surgical system of example 1, wherein one or more of the plurality of anchor assemblies has a rod-receiving portion that is geometrically congruent to a respective section of one of the one or more patient-specific spinal rods.
3. The surgical system of any of examples 1-2, wherein each of the plurality of anchor assemblies includes a bone screw.
4. A surgical system comprising:
   one or more processors; and
   one or more memories storing instructions that, when executed by the one or more processors, cause the surgical system to perform a process comprising obtaining one or more patient images of a patient;
      generating an anatomical model of the patient based on the one or more patient images;
      simulating, using a surgery manager system, a planned corrected anatomy of the patient based on the anatomical model;
      designing a first patient-specific implant for positioning anatomical elements of the patient to achieve the planned corrected anatomy;
      designing a second patient-specific implant to hold the first patient-specific implant and to contact one or more of the anatomical elements; and
      generating three-dimensional model data for the first patient-specific implant and for the second patient-specific implant, wherein the three-dimensional model data is configured to be transmitted to manufacture the first patient-specific implant and the second patient-specific implant.
5. The surgical system of example 4, wherein designing the first patient-specific implant includes:
   obtaining an implant type for the first patient-specific implant;
   selecting a plurality of design parameters for the first patient-specific implant based on the implant type;
   for each of the plurality of design parameters, selecting respective values based on the planned corrected anatomy; and
   generating a model of the first patient-specific implant with the respective values.
6. The surgical system of any of examples 4-5, wherein the plurality of design parameters include at least one a curvature, a number of curves, or a dimension.
7. The surgical system of any of examples 4-6, wherein
   the planned corrected anatomy includes a target spinal curvature, and
   the first patient-specific implant is a spinal rod with curvature matching the target spinal curvature.
8. The surgical system of any of examples 4-7, wherein
   designing the first patient-specific implant includes
      determining a first position for the first patient-specific implant, and
      determining a first configuration of the first patient-specific implant;
   designing the second patient-specific implant includes
      determining a second configuration of the second patient-specific implant to couple to the first patient-specific implant in the first configuration and to hold the first patient-specific implant at the first position.
9. A method comprising:
   obtaining a digital model of anatomy of a patient and anatomical correction information;
   selecting an implant system with a plurality of patient-specific implants that fit together for achieving an anatomical correction based on the anatomical correction information; and
   for each of the plurality of patient-specific implants,
      selecting a set of parameters for designing the patient-specific implant based on the digital model and the anatomical correction information; and
      generating an implant designer graphical user interface (GUI) for displaying the set of parameters, values for the respective parameters, a planned anatomy of the patient, and a model of the patient-specific implant positioned along the planned anatomy, wherein the model of the patient-specific implant represents the values.

10. The method of example 9, further comprising:

determining one or more fitting relationships between two or more of the patient-specific implants; and modifying at least one model of the two or more of the patient-specific implants based on the one or more fitting relationships.

11. The method of any of examples 9-10, further comprising generating a model of the implant system having the plurality of patient-specific implants fitting together to achieve the anatomical correction of the patient.

12. The method of any of examples 9-11, further comprising:

identifying an interface between two of the plurality of patient-specific implants;

selecting a fitting routine based on the interface; and modifying, using the fitting routine, the one or both of the two patient-specific implants to achieve a threshold fit.

13. The method of any of examples 9-12, further comprising modifying only portions of the one or both of the two patient-specific implants positioned outside of bony anatomy.

14. The method of any of examples 9-13, further comprising:

dynamically modifying a model of the implant system by modifying a first one of the plurality of patient-specific implants according to a modified value for the first one of the plurality of patient-specific implants;

modifying a second one of the plurality of patient-specific implants to fit with the first one of the plurality of patient-specific implants; and generating a viewable image of the modified model of the implant system with the modified first and second one of the plurality of patient-specific implants.

15. The method of any of examples 9-14, further comprising simulating, using a surgery manager system, a predicted corrected anatomy of the patient based on a simulated implantation of the implant system using a virtual model representing anatomy of the patient;

generating, using the surgery manager system, surgical feedback for assisting an individual with the modified implant system in a surgical procedure, wherein the surgical feedback is based on the simulated implantation; and sending, from the surgery manager system, a viewable surgical plan for viewing by the individual.

16. The method of any of examples 9-15, further comprising:

determining whether a threshold amount of patient data of the patient is available for intra-operatively simulating implantation of an intra-operatively modified implant to meet a confidence score, wherein intra-operative surgical feedback is sent after determining that the threshold amount of patient data of the patient is available.

17. The method of any of examples 9-16, wherein the plurality of patient-specific implants includes a rod, wherein the method further comprises:

modifying a curvature of the rod or a length of the rod.

18. The method of any of examples 9-17, further comprising:

determining whether the implant system meets a plan generation threshold; and in response to the implant system meeting the plan generation threshold, generating a surgical plan based on usage of the implant system.

19. The method of any of examples 9-18, further comprising:

linking surgery manager system to an interactive surgical plan displayable by a user device, wherein the surgery manager system stores parametric information of model; and synchronizing, using the surgery manager system, the interactive surgical plan and a simulator module that receives values to display new simulation data generated by the simulator module for concurrently evaluating the plurality of patient-specific implants.

20. The method of any of examples 9-19, further comprising:

generating a measurable virtual model of anatomy of the patient based on simulated implantation of the implant system;

selecting at least one measuring algorithm from a set of measuring algorithms based on a target outcome for a planned surgical procedure; and measuring one or more planned metrics for evaluating the planned surgical procedure using the at least one measuring algorithm and the measurable virtual model of anatomy of the patient, wherein the surgical feedback includes the one or more planned metrics.

21. A method comprising:

selecting a design process protocol for designing a patient-specific implant system based on a target correction for a patient; and for each of a plurality of patient-specific implants of the patient-specific implant system— selecting a set of parameters for designing each of the plurality of patient-specific implants based on patient anatomy and the target correction for the patient, generating an implant designer graphical user interface (GUI) for displaying the set of parameters for the design process protocol, values for the respective parameters, and a planned anatomy of the patient, and generating a design for each of the plurality of patient-specific implants such that the plurality of patient-specific implants cooperate to anatomical correction to the patient based on the target correction.

22. The method of example 21, wherein the target correction for the patient includes spinal realignment, and the planned anatomy of the patient is represented by a virtual model of the patient anatomy of the patient with the target correction.

23. The method of any of examples 21-22, wherein the design process protocol is a user-controlled design protocol in which a user inputs the values or a machine learning process protocol in which a machine learning module generates the values.

24. The method of any of examples 21-23, wherein the design process protocol includes a virtual modeling protocol for generating a model of anatomy of the patient and a parametric modeling process for generating a parametric model of the patient-specific implant system.

25. The method of any of examples 21-24, further comprising:

obtaining measurements using a model of the patient anatomy; and generating a parametric model of the patient-specific implant system based on the measurements.

26. The method of any of examples 21-25, further comprising:

virtually positioning the parametric model of the patient-specific implant system along the model of anatomy of the patient; and generating a viewable data illustrating the patient-specific implant system virtually positioned in the patient.

27. The method of any of examples 21-26, further comprising:

generating a parametric model of the patient-specific implant system;

modifying the parametric model based on a modification to one or more of the values; and determining whether the modified the parametric model meets at least one design criteria.

28. The method of any of examples 21-27, wherein the at least one design criteria is inputted by a user.

29. The method of any of examples 21-28, wherein the at least one design criteria includes a target correction to the patient.

30. The method of any of examples 21-29, further comprising generating a manufacturing design for each of the plurality of patient-specific implants for individually manufacturing each of the plurality of patient-specific implants.

31. The method of any of examples 21-30, further comprising generating an implant designer graphical user interface (GUI) linked to a parametric model of the patient-specific implant system, wherein the implant designer GUI is configured to display the patient-specific implant system modified to accommodate a modification of one of the plurality of patient-specific implants.

32. The method of any of examples 21-31, further comprising modifying one of the plurality of patient-specific implants based on a modification to another one of the plurality of patient-specific implants.

33. A surgical system, comprising:

a patient-specific implant system including one or more patient-specific spinal rods for a patient; and a plurality of fixation elements configured to anchor to vertebrae of the patient and to hold the one or more patient-specific spinal rods to achieve a target anatomical configuration when implanted in the patient.

34. The surgical system of example 33, wherein two or more of the plurality of fixation elements have different configurations and are configured to securely hold respective sections of one of the one or more patient-specific spinal rods.

35. The surgical system of any of examples 33-34, wherein one or more of the plurality of fixation elements are anchor assemblies each with a rod couple configured to receive and hold a section of one of the one or more patient-specific spinal rods.

36. The surgical system of any of examples 33-35, wherein the one or more patient-specific spinal rods includes a first rod and a second rod, wherein at least one of the plurality of fixation elements has a rod couple configured to hold the first rod more securely than the second rod.

37. The surgical system of any of examples 33-36, wherein the first rod and the second rod have different configurations.

38. The surgical system of any of examples 33-37, wherein the different configurations include different lengths, diameters, and/or curvatures.

39. The surgical system of any of examples 33-38, wherein the patient-specific implant system includes positioning indicia indicating at least one of positioning of the plurality of fixation elements along the one or more patient-specific spinal rods, or positioning of the patient-specific implant system relative to the patient.

40. The surgical system of any of examples 33-39, wherein the positioning indicia are on the one or more patient-specific spinal rods and the plurality of fixation elements.

41. The surgical system of any of examples 33-40, wherein each of the one or more patient-specific spinal rods is a multi-level spinal rod.

42. The surgical system of any of examples 33-41, further comprising a digital surgical plan including images of the target anatomical configuration and one or more metrics for the patient-specific implant system.

43. The surgical system of any of examples 33-42, wherein each of the plurality of fixation elements includes a bone anchor, and a rod couple couplable to the bone anchor and configured to hold one of the one or more patient-specific spinal rods.

44. The surgical system of any of examples 33-43, further comprising a virtual model of the patient in the target anatomical configuration.

45. The surgical system of any of examples 33-44, further comprising a surgical kit with the patient-specific implant system with additional fixation elements of different configurations.

46. A surgical kit substantially as shown and described.

47. A implant system substantially as shown and described.

48. A method comprising any process in examples 1-8.

49. A non-transitory computer-readable medium storing instructions that, when executed by a computing system, cause the computing system to perform operations of any process in examples 1-8.

50. A computing system comprising:

one or more processors; and one or more memories storing instructions that, when executed by the one or more processors, cause the computing system to perform a process of any one of methods in examples 9-32.

51. A non-transitory computer-readable medium storing instructions that, when executed by a computing system, cause the computing system to perform operations of any one of methods in examples 9-32.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically malleable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

- U.S. application Ser. No. 16/048,167, filed on Jul. 27, 2017, titled "SYSTEMS AND METHODS FOR ASSISTING AND AUGMENTING SURGICAL PROCEDURES";
- U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";
- U.S. application Ser. No. 16/207,116, filed on Dec. 1, 2018, titled "SYSTEMS AND METHODS FOR MULTI-PLANAR ORTHOPEDIC ALIGNMENT";
- U.S. application Ser. No. 16/352,699, filed on Mar. 13, 2019, titled "SYSTEMS AND METHODS FOR ORTHOPEDIC IMPLANT FIXATION";
- U.S. application Ser. No. 16/383,215, filed on Apr. 12, 2019, titled "SYSTEMS AND METHODS FOR ORTHOPEDIC IMPLANT FIXATION";
- U.S. application Ser. No. 16/569,494, filed on Sep. 12, 2019, titled "SYSTEMS AND METHODS FOR ORTHOPEDIC IMPLANTS";
- U.S. Application No. 62/773,127, filed on Nov. 29, 2018, titled "SYSTEMS AND METHODS FOR ORTHOPEDIC IMPLANTS";
- U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";
- U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS";
- U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS";
- U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";
- U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS";
- U.S. application Ser. No. 17/100,396, filed Nov. 20, 2020, titled "PATIENT-SPECIFIC VERTEBRAL IMPLANTS WITH POSITIONING FEATURES";
- U.S. application Ser. No. 17/124,822, filed Dec. 17, 2020, titled "PATIENT-SPECIFIC MEDICAL PROCEDURES AND DEVICES, AND ASSOCIATED SYSTEMS AND METHODS";
- U.S. application Ser. No. 17/868,729, filed Jul. 19, 2022, titled "SYSTEMS FOR PREDICTING INTRAOPERATIVE PATIENT MOBILITY AND IDENTIFYING MOBILITY-RELATED SURGICAL STEPS";
- U.S. application Ser. No. 17/978,746, filed Nov. 1, 2022, titled "PATIENT-SPECIFIC SPINAL INSTRUMENTS FOR IMPLANTING IMPLANTS AND DECOMPRESSION PROCEDURES";
- International Application No. PCT/US2021/012065, filed Jan. 4, 2021, titled "PATIENT-SPECIFIC MEDICAL PROCEDURES AND DEVICES, AND ASSOCIATED SYSTEMS AND METHODS";
- International Patent Application No. PCT/US22/48729, filed Nov. 2, 2022, titled "PATIENT-SPECIFIC ARTHROPLASTY DEVICES AND ASSOCIATED SYSTEMS AND METHODS";
- U.S. application Ser. No. 18/113,573, filed Feb. 23, 2023, titled "PATIENT-SPECIFIC IMPLANT DESIGN AND MANUFACTURING SYSTEM WITH A DIGITAL FILING CABINET MANAGER";
- U.S. application Ser. No. 17/878,633, filed Aug. 1, 2022, titled "NON-FUNGIBLE TOKEN SYSTEMS AND METHODS FOR STORING AND ACCESSING HEALTHCARE DATA";
- U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";
- U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME";
- U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS";
- U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA"
- International Patent Application No. PCT/US22/48729, filed Nov. 2, 2022, titled "PATIENT-SPECIFIC ARTHROPLASTY DEVICES AND ASSOCIATED SYSTEMS AND METHODS";
- U.S. application Ser. No. 18/113,573, filed Feb. 23, 2023, titled "PATIENT-SPECIFIC IMPLANT DESIGN AND

MANUFACTURING SYSTEM WITH A DIGITAL FILING CABINET MANAGER";

U.S. application Ser. No. 17/878,633, filed Aug. 1, 2022, titled "NON-FUNGIBLE TOKEN SYSTEMS AND METHODS FOR STORING AND ACCESSING HEALTHCARE DATA";

U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME";

U.S. application Ser. No. 18/384,762, filed Oct. 27, 2023, titled "SYSTEMS AND METHODS FOR SELECTING, REVIEWING, MODIFYING, AND/OR APPROVING SURGICAL PLANS;"

U.S. application Ser. No. 18/408,452, filed Jan. 9, 2024, titled "SYSTEM FOR MODELING PATIENT SPINAL CHANGES";

U.S. application Ser. No. 18/415,577, filed Jan. 17, 2024, titled "PATIENT-SPECIFIC IMPLANT DESIGN AND MANUFACTURING SYSTEM WITH A SURGICAL IMPLANT POSITIONING MANAGER";

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS";

U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA";

PCT Application No. PCT/US24/10202, filed Jan. 3, 2024, titled "PATIENT-SPECIFIC SPINAL FUSION DEVICES AND ASSOCIATED SYSTEMS AND METHODS";

U.S. application Ser. No. 18/892,151, filed: Sep. 20, 2024, titled "ROTATABLE AND SURGICAL APPROACH-SPECIFIC INTERVERTEBRAL IMPLANTS FOR FUSION TECHNIQUES;" and U.S. Application No. 63/717,251, filed Nov. 6, 2024, titled "INTRA-OPERATIVELY MODIFIED IMPLANTS FOR SURGICAL PROCEDURES."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method for treating a spinal deformity, the method comprising:

obtaining a digital model of anatomy of a patient and anatomical correction information;

selecting an implant system with a plurality of patient-specific anchor assemblies and a patient-specific rod configured to fit and connect together in a predetermined relative orientation for achieving an anatomical correction for a spine of the patient based on the anatomical correction information and one or more fitting relationships between two or more of the plurality of patient-specific anchor assemblies and the patient-specific rod, wherein each of the plurality of patient-specific anchor assemblies includes:

a rod holder, a rod retainer operable to couple the rod holder to the patient-specific rod, and a bone anchor including:

a seating member couplable to the rod holder in only one predetermined configuration based on the predetermined relative orientation, and a threaded shaft fixedly coupled to the seating member in only one configuration based on the predetermined relative orientation; and determining a target implant position of the patient-specific rod;

for each of the plurality of patient-specific anchor assemblies, selecting a set of parameters for designing the patient-specific anchor assembly based on the digital model and the anatomical correction information, wherein the set of parameters includes a patient-specific trajectory for each of the threaded shaft relative to a corresponding one of the seating members;

determining the trajectory of each of the threaded shaft relative to the patient-specific rod based on the target implant position of the patient-specific rod and the anatomy of the patient such that the rod holders and the seating members cooperate to lock the threaded shafts at different fixed trajectories relative to the patient-specific rod; and generating an implant designer graphical user interface (GUI) for displaying the set of parameters, a planned spinal anatomy of the patient, and a model of the patient-specific rod and the plurality of patient-specific anchor assemblies positioned along the planned spinal anatomy to achieve the anatomical correction information.

2. The method of claim 1, further comprising:

determining the one or more fitting relationships between the two or more of the plurality of patient-specific anchor assemblies; and modifying at least one model of the two or more of the plurality of patient-specific anchor assemblies based on the one or more fitting relationships.

3. The method of claim 1, further comprising generating a model of the implant system having the plurality of patient-specific anchor assemblies fitting together to achieve the anatomical correction of the patient.

4. The method of claim 1, further comprising:
identifying an interface between two of the plurality of patient-specific anchor assemblies;
selecting a fitting routine based on the interface; and
modifying, using the fitting routine, at least one of the two of the plurality of patient-specific anchor assemblies implants to achieve a threshold fit.

5. The method of claim 4, further comprising modifying only portions of at least one of the two of the plurality of patient-specific anchor assemblies positioned outside of bony anatomy.

6. The method of claim 1, further comprising:
dynamically modifying a model of the implant system by
modifying a first one of the plurality of patient-specific anchor assemblies according to a modified value for the first one of the plurality of patient-specific anchor assemblies;
modifying a second one of the plurality of patient-specific anchor assemblies to fit with the first one of the plurality of patient-specific anchor assemblies; and
generating a viewable image of the modified model of the implant system with the modified first one and modified second one of the plurality of patient-specific anchor assemblies.

7. The method of claim 6, further comprising
simulating, using a surgery manager system, a predicted corrected anatomy of the patient based on a simulated implantation of the implant system using a virtual model representing anatomy of the patient;
generating, using the surgery manager system, surgical feedback for assisting an individual with the modified model of the implant system in a surgical procedure, wherein the surgical feedback is based on the simulated implantation; and
sending, from the surgery manager system, a viewable surgical plan for viewing by the individual.

8. The method of claim 7, further comprising:
determining whether a threshold amount of patient data of the patient is available for intra-operatively simulating implantation of an intra-operatively modified implant to meet a confidence score, wherein intra-operative surgical feedback is sent after determining that the threshold amount of patient data of the patient is available.

9. The method of claim 7, further comprising:
generating a measurable virtual model of anatomy of the patient based on simulated implantation of the implant system;
selecting at least one measuring algorithm from a set of measuring algorithms based on a target outcome for a planned surgical procedure; and
measuring one or more planned metrics for evaluating the planned surgical procedure using the at least one measuring algorithm and the measurable virtual model of anatomy of the patient, wherein the surgical feedback includes the one or more planned metrics.

10. The method of claim 1, wherein the method further comprises:
modifying a curvature of the patient-specific rod or a length of the patient-specific rod.

11. The method of claim 1, further comprising:
determining whether the implant system meets a plan generation threshold; and
in response to the implant system meeting the plan generation threshold, generating a surgical plan based on usage of the implant system.

12. The method of claim 1, further comprising:
linking surgery manager system to an interactive surgical plan displayable by a user device, wherein the surgery manager system stores parametric information of the digital model; and
synchronizing, using the surgery manager system, the interactive surgical plan and a simulator module that receives values to display new simulation data generated by the simulator module for concurrently evaluating the plurality of patient-specific anchor assemblies.

13. A method for treating a spinal deformity, the method comprising:
selecting a design process protocol for designing a patient-specific implant system based on a target correction for a patient;
selecting an implant system with a plurality of patient-specific anchor assemblies and a patient-specific rod that are configured to fit and connect together in a predetermined relative orientation for achieving an anatomical correction for a spine of the patient based on one or more fitting relationships between two or more of the plurality of patient-specific anchor assemblies, wherein each of the patient-specific anchor assemblies includes:
a rod holder,
a rod retainer operable to couple the rod holder to the patient-specific rod, and
a bone anchor including:
a seating member couplable to the rod holder in only one predetermined configuration based on the predetermined relative orientation, and
a threaded shaft fixedly coupled to the seating member in only one configuration based on the predetermined relative orientation, and
determining a target implant position of the patient-specific rod;
for each of a plurality of patient-specific anchor assemblies of the patient-specific implant system;
selecting a set of parameters for designing each of the plurality of patient-specific anchor assemblies based on patient anatomy and the target correction for a region of the spine the patient, wherein the set of parameters includes a patient-specific trajectory for each of the threaded shaft relative to a corresponding one of the seating members,
determining a trajectory of each of the threaded shaft relative to the patient-specific rod based on the target implant position of the patient-specific rod and the anatomy of the patient such that the rod holder and the seating member in the only one predetermined configuration to lock threaded shafts at different fixed trajectories relative to the patient-specific rod,
generating an implant designer graphical user interface (GUI) for displaying the set of parameters for the design process protocol, values for the respective parameters, and a planned anatomy of the patient, and
generating a design for each of the plurality of patient-specific anchor assemblies such that the plurality of patient-specific anchor assemblies cooperate to anatomical correction to the patient based on the target correction.

14. The method of claim 13, wherein
the target correction for the patient includes spinal realignment, and
the planned anatomy of the patient is represented by a virtual model of the patient anatomy of the patient with the target correction.

15. The method of claim 13, wherein the design process protocol is a user-controlled design protocol in which a user inputs the values or a machine learning process protocol in which a machine learning module generates the values.

16. The method of claim 13, wherein the design process protocol includes a virtual modeling protocol for generating a model of anatomy of the patient and a parametric modeling process for generating a parametric model of the patient-specific implant system.

17. The method of claim 16, further comprising:
virtually positioning the parametric model of the patient-specific implant system along the model of anatomy of the patient; and
generating a viewable data illustrating the patient-specific implant system virtually positioned in the patient.

18. The method of claim 13, further comprising:
obtaining measurements using a model of the patient anatomy; and
generating a parametric model of the patient-specific implant system based on the measurements.

19. The method of claim 13, further comprising:
generating a parametric model of the patient-specific implant system;
modifying the parametric model based on a modification to one or more of the values; and
determining whether the modified parametric model meets at least one design criteria.

20. The method of claim 19, wherein the at least one design criteria is inputted by a user.

21. The method of claim 19, wherein the at least one design criteria includes a target correction to the patient.

22. The method of claim 13, further comprising generating a manufacturing design for each of the plurality of patient-specific anchor assemblies for individually manufacturing each of the plurality of patient-specific anchor assemblies.

23. A method for treating a spinal deformity, the method comprising:
obtaining a digital model of anatomy of a patient and an anatomical correction information;
selecting an implant system with a plurality of patient-specific anchor assemblies and a patient-specific rod that are configured to fit and couple together in a predetermined relative orientation to achieve a target anatomical correction for a spine of the patient when implanted based the anatomical correction information and fitting relationships between two or more of the plurality of patient-specific anchor assemblies and the patient-specific rod, wherein each of the anchor assemblies includes;
a rod holder,
a rod retainer operable to couple the rod holder to the patient-specific rod, and
a bone anchor including:
a seating member couplable to the rod holder in only one predetermined configuration based on the predetermined relative orientation, and
a threaded shaft fixedly coupled to the seating member in only one configuration based on the predetermined relative orientation; and
for each of the plurality of patient-specific anchor assemblies, selecting a set of parameters for designing each of the plurality of patient-specific anchor assemblies based on the digital model and the target anatomical correction, wherein the set of parameters includes a patient-specific trajectory for each of the threaded shaft relative to a corresponding one of the seating members; and
determining a trajectory of each the threaded shaft relative to the patient-specific rod based on a target implant position of the patient-specific rod and the anatomy of the patient such that the rod holders and the seating members couple together to lock the threaded shafts at different fixed trajectories relative to the patient-specific rod,
generating an implant designer graphical user interface (GUI) for displaying the set of parameters, values for the respective parameters, a planned spinal anatomy of the patient, and a model of each of the plurality of patient-specific anchor assemblies digitally positioned along the planned spinal anatomy, wherein the model of each of the plurality of patient-specific anchor assemblies represents the values.

24. The method of claim 23, further comprising virtually fitting the implant system to the patient by:
determining one or more fitting relationships between two or more of the plurality of patient-specific anchor assemblies; and
modifying at least one model of the two or more of the plurality of patient-specific anchor assemblies based on the one or more fitting relationships.

25. A method for treating a spinal deformity, the method comprising:
obtaining a digital model of anatomy of a patient and an anatomical correction information;
selecting a spinal implant system configured to extend across multiple levels of a spine of the patient, wherein the spinal implant system includes a plurality of patient-specific anchor assemblies and a patient-specific rod configured to be coupled together in a predetermined relative orientation to achieve a target anatomical correction in the patient based on the anatomical correction information and fitting relationships between plurality of the patient-specific anchor assemblies and the patient-specific rod; and
wherein each of the anchor assemblies includes:
a rod holder,
a rod retainer operable to couple the rod holder to the patient-specific rod, and
a bone anchor including:
a seating member couplable to the rod holder in only one predetermined configuration based on the predetermined relative orientation, and
a threaded shaft fixedly coupled to the seating member in only one configuration based on the predetermined relative orientation;
for each of patient-specific anchor assemblies, selecting a set of parameters for designing the respective each of patient-specific anchor assemblies based on the digital model and the target anatomical correction, wherein the set of parameters includes a patient-specific trajectory for each of the threaded shaft relative to a corresponding one of the seating members;
determining the trajectory of the threaded shaft relative to the patient-specific rod based on a target implant position of the patient-specific rod and the anatomy of the patient such that the rod holders and the seating members cooperate to lock the threaded shafts at different fixed trajectories relative to the patient-specific rod; and
generating an implant designer graphical user interface for displaying the set of parameters, values for the respective parameters, a planned spinal anatomy of the patient and a representation of each of the patient-specific anchor assemblies digitally positioned along the planned spinal anatomy to achieve the target anatomical correction.

26. The method of claim 25, wherein the spinal implant system is a posterior fixation system, and the plurality of patient-specific anchor assemblies includes two custom spinal rods configured to extend across the multiple levels, wherein the two custom spinal rods have different configurations.

* * * * *